US008317737B2

(12) United States Patent
Hyde et al.

(10) Patent No.: US 8,317,737 B2
(45) Date of Patent: Nov. 27, 2012

(54) DEVICE FOR ACTIVELY REMOVING A TARGET COMPONENT FROM BLOOD OR LYMPH OF A VERTEBRATE SUBJECT

(75) Inventors: Roderick A. Hyde, Redmond, WA (US); Muriel Y. Ishikawa, Livermore, CA (US); Edward K. Y. Jung, Bellevue, WA (US); Robert Langer, Newton, MA (US); Eric C. Leuthardt, St. Louis, MO (US); Nathan P. Myhrvold, Bellevue, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 316 days.

(21) Appl. No.: 12/803,449

(22) Filed: Jun. 25, 2010

(65) Prior Publication Data
US 2011/0034908 A1  Feb. 10, 2011

Related U.S. Application Data

(63) Continuation-in-part of application No. 12/380,399, filed on Feb. 25, 2009, and a continuation-in-part of application No. 12/380,400, filed on Feb. 25, 2009, and a continuation-in-part of application No. 12/660,926, filed on Mar. 5, 2010, and a continuation-in-part of application No. 12/660,928, filed on Mar. 5, 2010, now Pat. No. 8,167,871.

(51) Int. Cl.
*A61M 37/00* (2006.01)
*C02F 1/44* (2006.01)
*A61K 9/22* (2006.01)

(52) U.S. Cl. ............... 604/4.01; 604/5.01; 604/5.04; 604/891.1; 210/502.1; 210/645

(58) Field of Classification Search .......... 604/4.01, 604/5.01, 5.04, 6.09, 6.08, 6.11, 500, 507, 604/508; 210/645, 501, 502.1, 745, 739
See application file for complete search history.

(56) References Cited

U.S. PATENT DOCUMENTS
4,444,878 A  4/1984 Paulus
(Continued)

FOREIGN PATENT DOCUMENTS
EP  1 550 454 A1  7/2005
(Continued)

OTHER PUBLICATIONS

Alexander et al.; "Molecular imprinting science and technology: a survey of the literature for the years up to and including 2003"; Journal of Molecular Recognition; 2006; pp. 106-180, vol. 19; John Wiley & Sons, Ltd.
(Continued)

*Primary Examiner* — Leslie Deak

(57) ABSTRACT

Devices, systems, and methods are disclosed herein for modulating the levels of one or more target components in the blood and/or lymph of a vertebrate subject for treatment of a disease or condition in the vertebrate subject. An implantable device is provided which includes a body defining at least one lumen configured for fluid flow; at least one first reservoir in communication with at least one lumen; one or more energy sources configured to provide energy to elicit one or more signal responses associated with one or more labels that bind to one or more target components in one or more of blood fluid or lymph fluid of the vertebrate subject; one or more sensors configured to detect the one or more signal responses associated with one or more labeled target components; and one or more reactive components in communication with the at least one lumen for release responsive to the one or more sensors.

54 Claims, 5 Drawing Sheets

U.S. PATENT DOCUMENTS

| | | | |
|---|---|---|---|
| 4,955,857 A * | 9/1990 | Shettigar | 604/6.06 |
| 5,092,886 A | 3/1992 | Dobos-Hardy | |
| 5,107,422 A | 4/1992 | Kamentsky et al. | |
| 5,281,199 A | 1/1994 | Ensminger et al. | |
| 5,411,551 A | 5/1995 | Winston et al. | |
| 5,470,570 A | 11/1995 | Taylor et al. | |
| 5,474,772 A | 12/1995 | Maddock | |
| 5,604,531 A | 2/1997 | Iddan et al. | |
| 5,702,432 A | 12/1997 | Chen et al. | |
| 5,790,691 A | 8/1998 | Narayanswamy et al. | |
| 5,797,898 A | 8/1998 | Santini, Jr. et al. | |
| 5,804,563 A | 9/1998 | Still et al. | |
| 5,830,207 A | 11/1998 | Leeb et al. | |
| 5,831,012 A | 11/1998 | Nilsson et al. | |
| 5,928,195 A | 7/1999 | Malamud et al. | |
| 5,985,579 A | 11/1999 | Buechler et al. | |
| 6,030,653 A | 2/2000 | Rosenthal | |
| 6,039,946 A * | 3/2000 | Strahilevitz | 424/140.1 |
| 6,132,992 A | 10/2000 | Ledbetter et al. | |
| 6,190,691 B1 | 2/2001 | Mak | |
| 6,240,312 B1 | 5/2001 | Alfano et al. | |
| 6,255,461 B1 | 7/2001 | Mosbach et al. | |
| 6,287,516 B1 * | 9/2001 | Matson et al. | 422/44 |
| 6,387,674 B1 | 5/2002 | Trasciatti et al. | |
| 6,416,495 B1 | 7/2002 | Kriesel et al. | |
| 6,425,867 B1 | 7/2002 | Vaezy et al. | |
| 6,451,257 B1 | 9/2002 | Flamer | |
| 6,454,759 B2 | 9/2002 | Krulevitch et al. | |
| 6,471,872 B2 | 10/2002 | Kitaevich et al. | |
| 6,488,704 B1 | 12/2002 | Connelly et al. | |
| 6,551,235 B2 | 4/2003 | Forsell | |
| 6,554,822 B1 | 4/2003 | Holschneider et al. | |
| 6,571,125 B2 | 5/2003 | Thompson | |
| 6,612,535 B1 | 9/2003 | Tai et al. | |
| 6,669,683 B2 | 12/2003 | Santini, Jr. et al. | |
| 6,670,427 B1 | 12/2003 | Ulbricht et al. | |
| 6,673,596 B1 | 1/2004 | Sayler et al. | |
| 6,720,402 B2 | 4/2004 | Langer et al. | |
| 6,733,471 B1 | 5/2004 | Ericson et al. | |
| 6,743,190 B2 | 6/2004 | Connelly et al. | |
| 6,755,621 B2 | 6/2004 | Lopez et al. | |
| 6,793,642 B2 | 9/2004 | Connelly et al. | |
| 6,796,956 B2 | 9/2004 | Hartlaub et al. | |
| 6,797,522 B1 | 9/2004 | Still et al. | |
| 6,808,522 B2 | 10/2004 | Richards et al. | |
| 6,849,183 B2 | 2/2005 | Gorsuch et al. | |
| 6,946,127 B2 | 9/2005 | Bitensky et al. | |
| 6,956,961 B2 | 10/2005 | Cong et al. | |
| 7,033,571 B2 | 4/2006 | Gutowska et al. | |
| 7,097,662 B2 | 8/2006 | Evans, III et al. | |
| 7,124,773 B2 | 10/2006 | Midtgård et al. | |
| 7,151,847 B2 | 12/2006 | Vaisberg et al. | |
| 7,244,232 B2 | 7/2007 | Connelly et al. | |
| 7,264,794 B2 | 9/2007 | Georgakoudi et al. | |
| 7,303,875 B1 | 12/2007 | Bock et al. | |
| 7,309,786 B2 | 12/2007 | Zhang et al. | |
| 7,319,038 B2 | 1/2008 | Southard | |
| 7,326,240 B1 | 2/2008 | Caro et al. | |
| 7,355,334 B2 | 4/2008 | Anazawa et al. | |
| 7,413,846 B2 | 8/2008 | Maloney et al. | |
| 7,415,359 B2 | 8/2008 | Hill et al. | |
| 7,476,210 B2 | 1/2009 | Gorsuch et al. | |
| 7,553,625 B2 | 6/2009 | Hoon et al. | |
| 7,892,766 B2 | 2/2011 | King et al. | |
| 8,000,784 B2 | 8/2011 | Ferren et al. | |
| 2002/0009759 A1 | 1/2002 | Terstappen et al. | |
| 2002/0034757 A1 | 3/2002 | Cubicciotti | |
| 2002/0164825 A1 | 11/2002 | Chen | |
| 2003/0231981 A1 | 12/2003 | Johnson et al. | |
| 2004/0018508 A1 | 1/2004 | Friedman | |
| 2004/0033584 A1 | 2/2004 | Lederberg | |
| 2004/0034317 A1 | 2/2004 | Gorsuch et al. | |
| 2004/0191246 A1 | 9/2004 | Connelly et al. | |
| 2004/0218724 A1 | 11/2004 | Chornenky et al. | |
| 2005/0121411 A1 | 6/2005 | Cohen | |
| 2005/0126916 A1 | 6/2005 | Lockard et al. | |
| 2005/0221529 A1 | 10/2005 | Bang et al. | |
| 2005/0251347 A1 | 11/2005 | Perona et al. | |
| 2005/0272974 A1 | 12/2005 | Iddan | |
| 2006/0039593 A1 | 2/2006 | Sammak et al. | |
| 2006/0083716 A1 | 4/2006 | Kaufman et al. | |
| 2006/0172318 A1 | 8/2006 | Medinz et al. | |
| 2006/0183223 A1 | 8/2006 | King et al. | |
| 2006/0234369 A1 | 10/2006 | Sih | |
| 2007/0010868 A1 | 1/2007 | Ferren et al. | |
| 2007/0021927 A1 | 1/2007 | Ishikawa et al. | |
| 2007/0066929 A1 | 3/2007 | Ferren et al. | |
| 2007/0066939 A1 | 3/2007 | Krulevitch et al. | |
| 2007/0083333 A1 | 4/2007 | Vitiello et al. | |
| 2007/0093739 A1 | 4/2007 | Brady et al. | |
| 2007/0156211 A1 | 7/2007 | Ferren et al. | |
| 2007/0178084 A1 | 8/2007 | King et al. | |
| 2007/0225633 A1 | 9/2007 | Ferren et al. | |
| 2007/0225634 A1 | 9/2007 | Ferren et al. | |
| 2007/0244520 A1 | 10/2007 | Ferren et al. | |
| 2007/0276208 A1 | 11/2007 | Connelly et al. | |
| 2007/0294150 A1 | 12/2007 | Jung et al. | |
| 2008/0033569 A1 | 2/2008 | Ferren et al. | |
| 2008/0058785 A1 | 3/2008 | Boyden et al. | |
| 2008/0103440 A1 | 5/2008 | Ferren et al. | |
| 2008/0201122 A1 | 8/2008 | Kelly et al. | |
| 2008/0241847 A1 | 10/2008 | Hoon et al. | |
| 2008/0275376 A1 | 11/2008 | Howell et al. | |
| 2008/0281400 A1 | 11/2008 | Philipp et al. | |
| 2008/0286278 A1 | 11/2008 | Connelly et al. | |
| 2009/0022768 A1 | 1/2009 | King et al. | |
| 2009/0043183 A1 | 2/2009 | Kermani et al. | |
| 2009/0054908 A1 | 2/2009 | Zand et al. | |
| 2009/0093713 A1 | 4/2009 | Hyde et al. | |
| 2009/0093728 A1 | 4/2009 | Hyde et al. | |
| 2009/0093807 A1 | 4/2009 | Hyde et al. | |
| 2009/0182127 A1 | 7/2009 | Kjaergaard et al. | |
| 2009/0298704 A1 | 12/2009 | Anwar et al. | |
| 2010/0167372 A1 | 7/2010 | King et al. | |
| 2010/0185134 A1 | 7/2010 | Houwen et al. | |

FOREIGN PATENT DOCUMENTS

WO    WO 2007/130586 A2    11/2007

OTHER PUBLICATIONS

Ammor, Mohammed Salim; "Recent Advances in the Use of Intrinsic Fluorescence for Bacterial Identification and Characterization"; J Fluoresc; 2007; pp. 1-5; Springer-Science + Business Media LLC.

An, Gary; "Introduction of an agent-based multi-scale modular architecture for dynamic knowledge representation of acute inflammation"; Theoretical Biology and Medical Modelling; 2008; pp. 1-20, vol. 5, No. 11; BioMed Central Ltd.

Anderson et al.; "Inactivation of Food-Borne Enteropathogenic Bacteria and Spoilage Fungi Using Pulsed-Light"; IEEE Transactions on Plasma Science; Feb. 2000; pp. 83-88; vol. 28, No. 1.

Baker et al.; "An Electronic, Aptamer-Based Small-Molecule Sensor for the Rapid, Label-Free Detection of Cocaine in Adulterated Samples and Biological Fluids"; J. Am. Chem. Soc.; 2006; pp. 3138-3139; vol. 128, No. 10; American Chemical Society.

Becker et al.; "An antibody-interleukin 2 fusion protein overcomes tumor heterogeneity by induction of a cellular immune response"; Proc. Natl. Acad. Sci. USA; Jul. 1996; pp. 7826-7831; vol. 93.

Békássy, Zoltán; "Long-Term Follow-Up of Cervical Intraepithelial Neoplasia Treated With Minimal Conization by Carbon Dioxide Laser"; Lasers in Surgery and Medicine; 1997; pp. 461-466; vol. 20; Wiley-Liss, Inc.

Bellin et al.; "Polymeric triple-shape materials"; PNAS; Nov. 28, 2006; pp. 18043-18047; vol. 103, No. 48; The National Academy of Sciences of the USA.

Bezrouk et al.; "Temperature Characteristics of Nitinol Spiral Stents"; Scripta Medica (BRNO); Oct. 2005; pp. 219-226; vol. 78, No. 4.

Bins et al.; "Texture of White Blood Cells Expressed by the Counting Densitogram"; Cytometry; 1981; pp. 321-324; vol. 1, No. 5; Society for Analytical Cytology.

Bouchard et al.; "Optical characterization of *Pseudomonas fluorescens* on meat surfaces using time-resolved fluorescence"; Journal of Biomedical Optics; Jan./Feb. 2006; pp. 0140011-1-0140011-7; vol. 11, No. 1; Society of Photo-Optical Instrumentation Engineers.

Brennan, John D.; "Preparation and Entrapment of Fluorescently Labeled Proteins for the Development of Reagentless Optical Biosensors"; Journal of Fluorescence; 1999; pp. 295-312; vol. 9, No. 4; Plenum Publishing Corporation.

Bright et al.; "Regenerable Fiber-Optic-Based Immunosensor"; Anal. Chem.; 1990; pp. 1065-1069; vol. 62; American Chemical Society.

Byrne et al.; "Molecular imprinting within hydrogels"; Advanced Drug Delivery Reviews; 2002; pp. 149-161; vol. 54; Elsevier Science B.V.

Cady et al.; "Optimized linkage and quenching strategies for quantum dot molecular beacons"; Molecular and Cellular Probes; 2007; pp. 116-124; vol. 21; Elsevier Ltd.

Camara et al.; "Seeding of epithelial cells into circulation during surgery for breast cancer: the fate of malignant and benign mobilized cells"; World Journal of Surgical Oncology; 2006; pp. 1-7; vol. 4, No. 67, BioMed Central Ltd.

Cao et al.; "Establishment of a new model for culturing rabbit osteoblasts in vitro"; Biomedical Materials; 2006; pp. L16-L19; vol. 1; IOP Publishing Ltd.

Cao et al.; "Molecular Beacon Aptamers for Protein Monitoring in Real-Time and in Homogeneous Solutions"; Current Proteomics; 2005; pp. 31-40; vol. 2; Bentham Science Publishers Ltd.

Chakravarty et al.; "Thermal ablation of tumor cells with antibody-functionalized single-walled carbon nanotubes"; PNAS; Jun. 24, 2008; pp. 8697-8702; vol. 105, No. 25; The National Academy of Sciences of the USA.

Challita-Eid et al.; "A B7.1-Antibody Fusion Protein Retains Antibody Specificity and Ability to Activate Via the T Cell Costimulatory Pathway"; The Journal of Immunology; 1998; pp. 3419-3426; vol. 160; The American Association of Immunologists.

Chan et al.; "Bactericidal effects of different laser wavelengths on periodontopathic germs in photodynamic therapy"; Lasers Med Sci; 2003; pp. 51-55; vol. 18; Springer-Verlag London Limited.

Chen et al.; "Aptamer from whole-bacterium SELEX as new therapeutic reagent against virulent *Mycobacterium tuberculosis*"; Biochemical and Biophysical Research Communications; 2007; pp. 743-748; vol. 357; Elsevier Inc.

Chen et al.; "Ubiquitin-associated (UBA) domains in Rad23 bind ubiquitin and promote inhibition of multi-ubiquitin chain assembly"; EMBO reports; 2001; pp. 933-938; vol. 2, No. 10; European Molecular Biology Organization.

Chung et al.; "Size Comparisons among Integral Membrane Transport Protein Homologues in *Bacteria, Archaea*, and *Eucarya*"; Journal of Bacteriology; Feb. 2001; pp. 1012-1021; vol. 183, No. 3; American Society for Microbiology.

Colas et al.; "Targeted modification and transportation of cellular proteins"; PNAS; Dec. 5, 2000; pp. 13720-13725; vol. 97, No. 25.

Complete Blood Count (CBC); pp. 1-7; last accessed on Oct. 5, 2009; http://www.webmd.com/a-to-z-guides/complete-blood-count-cbc.

Crawford et al.; "Peptide aptamers: Tools for biology and drug discovery"; Briefings in Functional Genomics and Proteomics; Apr. 2003; pp. 72-79; vol. 2, No. 1; Henry Stewart Publications.

Cristofanilli et al.; "Circulating Tumor Cells, Disease Progression, and Survival in Metastatic Breast Cancer"; The New England Journal of Medicine; Aug. 19, 2004; pp. 781-791; vol. 351, No. 8; Massachusetts Medical Society.

Davies, Michael J.; "Singlet oxygen-mediated damage to proteins and its consequences"; Biochemical and Biophysical Research Communications; 2003; pp. 761-770; vol. 305; Elsevier Science (USA).

Dehio, Christoph; "Infection-associated type IV secretion systems of *Bartonella* and their diverse roles in host cell interaction"; Cellular Microbiology; 2008; pp. 1591-1598; vol. 10, No. 8; Blackwell Publishing Ltd.

Dempster et al.; "Using Granulometries in Processing Images of Malarial Blood"; IEEE; 2001; pp. V-291-V294.

Desimone et al.; "Bactericidal Effect of 0.95-mW Helium-Neon and 5-mW Indium-Gallium-Aluminum-Phosphate Laser Irradiation at Exposure Times of 30, 60, and 120 Seconds on Photosensitized *Staphylococcus aureus* and *Pseudomonas aeruginosa* In Vitro"; Physical Therapy; Sep. 1999; pp. 839-846; vol. 79, No. 9; American Physical Therapy Association.

Doornbos et al.; "White Blood Cell Differentiation Using a Solid State Flow Cytometry"; 1993; pp. 589-594; vol. 14; Wiley-Liss, Inc.

Durick et al.; "Cellular biosensors for drug discovery"; Biosensors & Bioelectronics; 2001; pp. 587-592; vol. 16; Elsevier Science B.V.

Eyre et al.; "MEMS Magnetic Sensor in Standard CMOS"; 1998; pp. 99-102.

Fan et al.; "Sensitive optical biosensors for unlabeled targets: A review"; Analytica Chimica Acta 620; 2008; pp. 8-26; Elsevier B.V.

Fan et al.; "Structures in *Bacillus subtilis* Are Recognized by CD14 in a Lipopolysaccharide Binding Protein-Dependent Reaction"; Infection and Immunity; Jun. 1999; pp. 2964-2968; vol. 67, No. 6; American Society for Microbiology.

Fei-Fei et al.; "One-Shot Learning of Object Categories"; IEEE Transactions on Pattern Analysis and Machine Intelligence; Apr. 2006; pp. 594-611; vol. 28, No. 4; IEEE Computer Society.

Fischer et al.; "Deep Tissue Penetration of Radiation: Modelling and Experiments"; 1 pg.; printed on Nov. 25, 2009.

Fizazi et al.; "High detection rate of circulating tumor cells in blood of patients with prostate cancer using telomerase activity"; Annals of Oncology; 2007; pp. 518-521; vol. 18, No. 3; European Society for Medical Oncology.

Flatmark et al.; "Immunomagnetic Detection of Micrometastatic Cells in Bone Marrow of Colorectal Cancer Patients"; Clinical Cancer Research; Feb. 2002; pp. 444-449; vol. 8.

Francisco et al.; "Production and fluorescence-activated cell sorting of *Escherichia coli* expressing a functional antibody fragment on the external surface"; Proc. Natl. Acad. Sci. USA; Nov. 1993; pp. 10444-10448; vol. 90.

Gao et al.; "A Micro Sensing Probe for Detecting Individual Biological Cells"; Proceedings of the 25th Annual International Conference of the IEEE EMBS, Cancun, Mexico, Sep. 17-21, 2003; pp. 3348-3351; IEEE.

Gao et al.; "Two-state selection of conformation-specific antibodies"; PNAS; Mar. 3, 2009; pp. 3071-3076; vol. 106, No. 9; The National Academy of Sciences of the USA.

Garlick et al.; "Avidin Binding of Radiolabeled Biotin Derivatives"; The Journal of Biological Chemistry; Jan. 5, 1988; pp. 210-215; vol. 263, No. 1; The American Society for Biochemistry and Molecular Biology, Inc.

Gibson et al.; "Ten-year experience of carbon dioxide laser ablation as treatment for cutaneous recurrence of malignant melanoma"; British Journal of Surgery; 2004; pp. 893-895; vol. 91; John Wiley & Sons, Inc.

Givrad et al.; "Implantable Minipump with MEMS Electrothermal Valve for Bolus Injection in Mice"; Proceedings of BIOMed2008; 3rd Frontiers in Biomedical Devices Conference; Jun. 18-20, 2008, Irvine, California, USA; pp. 1-2; ASME.

Grayson et al.; "A BioMEMS Review: MEMS Technology for Physiologically Integrated Devices"; Proceedings of the IEEE; Jan. 2004; pp. 6-21; vol. 92, No. 1; IEEE.

Green et al.; "Disinfection of selected *Aspergillus* spp. using ultraviolet germicidal irradiation"; Can. J. Microbiol.; 2004; pp. 221-224; vol. 50; NRC Canada.

Grönqvist et al.; "Bactericidal Effect of Pulsed 1,064 nm Nd:YAG Laser Light on *Staphylococcus epidermidis* Is of Photothermal Origin: An In Vitro Study"; Lasers in Surgery and Medicine; 2000; pp. 336-340; vol. 27; Wiley-Liss, Inc.

Guffey et al.; "Effects of Combined 405-nm and 880-nm Light on *Staphylococcus aureus* and *Pseudomonas aeruginosa in Vitro*"; Photomedicine and Laser Surgery; Nov. 6, 2006; pp. 680-683; vol. 24, No. 6; Mary Ann Liebert, Inc.

Guthrie et al.; "Assays for cytokines using aptamers"; Methods; 2006; pp. 324-330; vol. 38; Elsevier Inc.

Hama et al.; "A Target cell-Specific Activatable Fluorescence Probe for In vivo Molecular Imaging of Cancer Based on a Self-Quenched Avidin-Rhodamine Conjugate"; Cancer Res; Mar. 15, 2007; pp. 2791-2799; vol. 67, No. 6; American Association for Cancer Research.

Hamblin et al.; "Rapid Control of Wound Infections by Targeted Photodynamic Therapy Monitored by In Vivo Bioluminescence Imaging"; Photochemistry and Photobiology; Jan. 2002; pp. 51-57; vol. 75, No. 1; American Society for Photobiology.

Hancock et al.; "Megawatt, Pulsed Ultraviolet Photon Sources for Microbial Inactivation"; IEEE Transactions on Plasma Science; Oct. 2004; pp. 2026-2031; vol. 32, No. 5; IEEE.

Hanna et al.; "Using a System-on-a-Chip Implantable Device to Filter Circulating Infected Cells in Blood or Lymph"; IEEE Transactions on Nanobioscience; Mar. 2003; pp. 6-13; vol. 2, No. 1; IEEE.

Hansen et al.; "Transbronchial laser ablation of benign and malignant tumors"; Minimally Invasive Therapy; 2006; pp. 4-8; vol. 15, No. 1; Taylor & Francis.

Heath et al.; "Antibody-targeted liposomes: Increase in specific toxicity of methotrexate-γ-aspartate"; Proc. Natl. Acad. Sci. USA; Mar. 1983; pp. 1377-1381; vol. 80.

He et al.; "In vivo quantitation of rare circulating tumor cells by multiphoton intravital flow cytometry"; PNAS; Jul. 10, 2007; pp. 11760-11765; vol. 104, No. 28; The National Academy of Sciences.

Ho et al.; "Isolation of anti-CD22 Fv with high affinity by Fv display on human cells"; PNAS; Jun. 20, 2006; pp. 9637-9642; vol. 103, No. 25.

Horata et al.; "Sequence variation of PfEMPI-DBLα in association with rosette formation in *Plasmodium falciparum* isolates causing severe and uncomplicated malaria"; Malaria Journal; 2009; pp. 1-11; vol. 8, No. 184; BioMed Central Ltd.

Horne et al.; "Which White Blood Cell Subtypes Predict Increased Cardiovascular Risk?"; Journal of the Americal College of Cardiology; 2005; pp. 1638-1643; vol. 45, No. 10; Elsevier Inc.

Hornyak, Tim; "RFID Powder"; Scientific American; Feb. 2008; pp. 68-71; Scientific American, Inc.

Hou et al.; "Disintegration of Biomacromolecules by Dielectric Barrier Discharge Plasma in Helium at Atmospheric Pressure"; IEEE Transactions on Plasma Science, Aug. 2008; pp. 1633-1637; vol. 36, No. 4; IEEE.

Htay et al.; "Drug-eluting stent: a review and update"; Vascular Health and Risk Management; 2005; pp. 263-276; vol. 1, No. 4; Dove Medical Press Limited.

Hu et al.; "Preparation of a biochip on porous silicon and application for label-free detection of small molecule-protein interactions"; Rapid Communications in Mass Spectrometry; 2007; pp. 1277-1281; vol. 21; John Wiley & Sons, Ltd.

Hu et al.; "A Chimeric Lym-1/Interleukin 2 Fusion Protein for Increasing Tumor Vascular Permeability and Enhancing Antibody Uptake"; Cancer Research; Nov. 1, 1996; pp. 4998-5004; vol. 56.

Humphreys et al.; "Assessment of Cumulative Allergen-Activated Lymph Node Cell Proliferation Using Flow Cytometry"; Toxicological Sciences; 2003; pp. 80-89; vol. 73; Society of Toxicology.

Jaiswal et al.; "Long-term multiple color imaging of live cells using quantum dot bioconjugates"; Nature Biotechnology; Jan. 2003; pp. 47-51; vol. 21; Nature Publishing Group.

Janda et al.; "Induction of an Antibody That Catalyzes the Hydrolysis of an Amide Bond"; Science; Sep. 2, 1988; pp. 1188-1191; vol. 241.

Javier et al.; "Aptamer-Targeted Gold Nanoparticles As Molecular-Specific Contrast Agents for Reflectance Imaging"; Bioconjugate Chem.; 2008; pp. 1309-1312; vol. 19, No. 6; American Chemical Society.

Jawhara et al.; "Monitoring of bactericidal action of laser by in vivo imaging of bioluminescent *E. coli* in a cutaneous wound infection"; Lasers Med Sci; 2006; pp. 153-159; vol. 21; Springer-Verlag London Limited.

Jayasena, Sumedha D.; "Aptamers: An Emerging Class of Molecules That Rival Antibodies in Diagnostics"; Clinical Chemistry; 1999; pp. 1628-1650; vol. 45, No. 9; American Association for Clinical Chemistry.

Jhaveri et al.; "In vitro selection of signaling aptamers"; Nature Biotechnology; Dec. 2000; pp. 1293-1297; vol. 18; Nature America Inc.

Jin et al.; "Immobilization of plasmid DNA on an anti-DNA antibody modified coronary stent for intravascular site-specific gene therapy"; The Journal of Gene Medicine; 2008; pp. 421-429; vol. 10; John Wiley & Sons, Ltd.

Johnson et al.; "Design and Testing of an Impedance-Based Sensor for Monitoring Drug Delivery"; Journal of the Electrochemical Society; 2005; pp. H6-H11; vol. 152, No. 1; The Electrochemical Society, Inc.

Jori et al.; "Photodynamic Therapy in the Treatment of Microbial Infections: Basic Principles and Perspective Applications"; Lasers in Surgery and Medicine; 2006; pp. 468-481; vol. 38; Wiley-Liss, Inc.

Kam et al.; "Carbon nanotubes as multifunctional biological transporters and near-infrared agents for selective cancer cell destruction"; PNAS; Aug. 16, 2005; pp. 11600-11605; vol. 102, No. 33; The National Academy of Sciences of the USA.

Karrer et al.; "Photodynamic Inactivation of *Staphylococci* with 5-Aminolaevulinic Acid or Photofrin"; Lasers Med Sci; 1999; pp. 54-61; vol. 14; Springer-Verlag London Limited.

Katial et al.; "Deleterious effects of electron beam radiation on allergen extracts"; J Allergy Clin Immunol; Aug. 2002; pp. 215-219; vol. 110.

Katsumata et al.; "Detection and evaluation of epithelial cells in the blood of colon cancer patients using RT-PCR"; Int J Clin Oncol; 2006; pp. 385-389; vol. 11; Abstract; 1 pg.; The Japan Society of Clinical Oncology.

Keefe et al.; "Photodynamic Therapy of High-Grade Cervical Intraepithelial Neoplasia With 5-Aminolevulinic Acid"; Lasers in Surgery and Medicine; 2002; pp. 289-293; vol. 31; Wiley-Liss, Inc.

Kellum et al.; "Understanding the Inflammatory Cytokine Response in Pneumonia and Sepsis"; Arch Intern Med; Aug. 13-27, 2007; pp. 1655-1663; vol. 167, No. 15; American Medical Association.

Kennedy et al.; "High intensity focused ultrasound: surgery of the future?"; The British Journal of Radiology; Sep. 2003; pp. 590-599; vol. 76; The British Institute of Radiology.

Kim et al.; "Real-Time Detection of Microbial Contamination"; IEEE Engineering in Medicine and Biology Magazine; Jan./Feb. 2004; pp. 122-129; IEEE.

Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.

Koenig et al.; "Laser-Induced Autofluorescence for Medical Diagnosis"; Journal of Fluorescence; 1994; pp. 17-40; vol. 4, No. 1; Plenum Publishing Corporation.

Koo et al.; "Development of a Streptavidin-Conjugated Single-Chain Antibody That Binds *Bacillus cereus* Spores"; Applied and Environmental Microbiology; Jul. 1998; pp. 2497-2502; vol. 64, No. 7; American Society for Microbiology.

Krüger et al.; "Development of a microfluidic device for fluorescence activated cell sorting"; Journal of Micromechanics and Microengineering; 2002; pp. 486-494; vol. 12; IOP Publishing Ltd.

Kufer et al.; "A revival of bispecific antibodies"; Trends in Biotechnology; May 2004; pp. 238-244; vol. 22, No. 5; Elsevier Ltd.

Kupper et al.; "Generation of human antibody fragments against *Streptococcus mutans* using a phage display chain shuffling approach"; BMC Biotechnology; 2005; pp. 1-12; vol. 5, No. 4; BioMed Central Ltd.

Kurt et al.; "Serum IL-1β, IL-6, IL-8, and TNF-α Levels in Early Diagnosis and Management of Neonatal Sepsis"; Mediators of Inflammation; 2007; pp. 1-5; Article ID 31397; Hindawi Publishing Corporation.

Lacroix-Desmazes et al.; "Catalytic IgG from Patients with Hemophilia A Inactivate Therapeutic Factor VIII"; The Journal of Immunology; 2006; pp. 1355-1363; vol. 177; The American Association of Immunologists, Inc.

Lee et al.; "A micro-machined LC-resonator for high-frequency magnetic sensor applications"; Intermag; 2006; p. 201 (text missing from electronic version).

Lee et al.; "Laser-Generated Stress Waves and Their Effects on the Cell Membrane"; IEEE Journal of Selected Topics in Quantum Electronics; Jul./Aug. 1999; pp. 997-1003; vol. 5, No. 4; IEEE.

Lee et al.; "Performance of an Immobilized Trypsin System for Improving Oxidative Stability of Milk"; 1974; pp. 473-476.

Lee et al.; "A strategy for predicting the chemosensitivity of human cancers and its application to drug discovery"; PNAS; Aug. 7, 2007; pp. 13086-13091; vol. 104, No. 32; The National Academy of Sciences of the USA.

Lepock, James R.; "Cellular effects of hyperthermia: relevance to the minimum dose for thermal damage"; Int. J. Hyperthermia; May-Jun. 2003; pp. 252-266; vol. 19, No. 3; Taylor & Francis Ltd.

Li et al.; "A Patient-Specific in silico Model of Inflammation and Healing Tested in Acute Vocal Fold Injury"; PLoS ONE; Jul. 2008; pp. 1-11; vol. 3, No. 7.

Lill et al.; "Microwave-Assisted Proteomics"; Mass. Spectrometry Reviews; 2007; pp. 657-671; vol. 26; Wiley-Periodicals, Inc.

López-Ferrer et al.; "Rapid Simple Processing for LC-MS-Based Quantitative Proteomics Using High Intensity Focused Ultrasound"; Journal of Proteome Research; 2008; pp. 3860-3867; vol. 7, No. 9; American Chemical Society.

Luckevich, Mark; "MEMS microvalves: the new valve world"; ValveWorld; May 2007; pp. 79-83; located at www.valve-world.net.

Ma et al.; "Potent Antitumor Activity of an Auristatin-Conjugated, Fully Human Monoclonal Antibody to Prostate-Specific Membrane Antigen"; Clin Cancer Res; Apr. 15, 2006; pp. 2591-2596; vol. 12, No. 8; American Association for Cancer Research.

Mahmud et al.; "Directing cell motions on micropatterened ratchets"; Nature Physics; 2009; pp. 606-612; vol. 5; Article Abstract; 2 pgs.

Maisch, Tim; "Anti-microbial photodynamic therapy: useful in the future?"; Lasers Med Sci; 2007; pp. 83-91; vol. 22; Springer-Verlag London Limited.

Malek et al.; "Identification and initial characterization of a rat monoclonal antibody reactive with the murine interleukin 2 receptor-ligand complex"; Proc. Natl. Acad. Sci USA; Sep. 1983; pp. 5694-5698; vol. 80.

Maloney et al.; "Implantable Microchips for Controlled Drug Delivery"; Proceedings of the 26th Annual International Conference of the IEEE EMBS, San Francisco, CA, USA; Sep. 1-5, 2004; pp. 2668-2669.

Martin et al.; "Learning to Detect Natural Image Boundaries Using Local Brightness, Color, and Texture Cues"; IEEE Transactions on Pattern Analysis and Machine Intelligence; May 2004; pp. 530-549; vol. 26, No. 5; IEEE Computer Society.

Mateus et al.; "Adherence of *Candida albicans* to Silicone Induces Immediate Enhanced Tolerance to Fluconazole"; Antimicrobial Agents and Chemotherapy; Sep. 2004; pp. 3358-3366; vol. 48, No. 9; American Society for Microbiology.

May, Mike; "Detection of Circulating Epithelial Cells"; Bioscience Technology; Jul. 2008; 3 pgs.; located at www.BioscienceTechnology.com.

McDevitt et al.; "Tumor Targeting with Antibody-Functionalized, Radiolabeled Carbon Nanotubes" The Journal of Nuclear Medicine; Jul. 2007; pp. 1180-1189; vol. 48, No. 7; Society of Nuclear Medicine, Inc.

Mendelow et al.; "Automated malaria detection by depolarization of laser light"; British Journal of Haematology; 1999; pp. 499-503; vol. 104; Blackwell Science Ltd.

Miller et al.; "Cancer Cells Ablation with Irreversible Electroporation"; Technology in Cancer Research & Treatment; Dec. 2005; pp. 1-7; vol. 4, No. 6; Adenine Press.

Miller et al.; "Photodynamic Therapy with the Phthalocyanine Photosensitizer Pc 4: The Case Experience with Preclinical Mechanistic and Early Clinical-Translational Studies"; Toxicol Appl Pharmacol; Nov. 1, 2007; pp. 290-299; vol. 224, No. 3.

Mittal et al.; "IL—10 In Early Rheumatoid Arthritis"; J Indian Rheumatoid Assoc; 2002; pp. 59-60; vol. 10.

Miyata et al.; "Tumor marker-responsive behavior of gels prepared by biomolecular imprinting"; PNAS; Jan. 31, 2006; pp. 1190-1193; vol. 103, No. 5; The National Academy of Sciences of the USA.

MMWR Weekly; Adult Blood Lead Epidemiology and Surveillance—United States, 2005-2007; Apr. 17, 2009; pp. 365-369; vol. 58, No. 14.

Mohamed et al.; "Development of a Rare Cell Fractionation Device: Application for Cancer Detection"; IEEE Transactions on Nanobioscience; Dec. 2004; pp. 251-256; vol. 3, No. 4; IEEE.

Mohan et al.; "Bokode: Imperceptible Visual tags for Camera Based Interaction from a Distance"; 8 pgs.; located at http://cameraculture.media.mit.edu/bokode; printed on Nov. 24, 2009.

Moore et al.; "The Comparative Size and Structure of Tumor Cells and Clumps in the Blood, Bone Marrow, and Tumor Imprints"; Cancer; Jan.-Feb. 1960; pp. 111-117; vol. 13, No. 1.

Nakada et al.; "Blood purification for hypercytokinemia"; Transfusion and Apheresis Science; 2006; pp. 253-264; vol. 35, Elsevier Ltd.

Nakano et al.; "Formulation of Nanoparticle-Eluting Stents by a Cationic Electrodeposition Coating Technology: Efficient Nano-Drug Delivery via Bioabsorbable Polymeric Nanoparticle-Eluting Stents in Porcine Coronary Arteries"; J. Am. Coll. Cardiol. Intv.; 2009; pp. 277-283; vol. 2, No. 4; The American College of Cardiology Foundation.

Narasipura et al.; "Purification of CD45+ hemtopoietic cells directly from human bone marrow using a flow-based P-selectin-coated microtube"; Am. J. Hematol.; 2008; pp. 627-629; vol. 83; Wiley-Liss, Inc.

National Cancer Institute FactSheet; "Lasers in Cancer Treatment: Questions and Answers"; Aug. 10, 2004; pp. 1-4.

Nemazee et al.; "Enhancing antibody: A novel component of the immune response"; Proc. Natl Acad. Sci. USA; Jun. 1982; pp. 3828-3832; vol. 79.

Nitin et al.; "Peptide-linked molecular beacons for efficient delivery and rapid mRNA detection in living cells"; Nucleic Acids Research; 2004; pp. 1-8; vol. 32, No. 6 e58; Oxford University Press.

Nitzan et al.; "Endogenous Porphyrin Production in Bacteria by δ-Aminolaevulinic Acid and Subsequent Bacterial Photoeradication"; Lasers Med Sci; 1999; pp. 269-277; vol. 14; Springer-Verlag London Limited.

Norberto et al.; "Laser photoablation of colorectal adenomas"; Surg Endosc; 2005; pp. 1045-1048; vol. 19; Springer Science+Business Media, Inc.

Noronha et al.; "Hyperactivated B cells in human inflammatory bowel disease"; Journal of Leukocyte Biology; Oct. 2009; pp. 1-10; vol. 86; Society for Leukocyte Biology.

Nowlan et al.; "Systemic cytokine levels and the effects of etanercept in TNF receptor-associated periodic syndrome (TRAPS) involving a C33Y mutation in TNFRSF1A"; Rheumatology; 2006; pp. 31-37; vol. 45; Oxford University Press.

Nussbaum et al.; "Effects of 810 nm Laser Irradiation on In Vitro Growth of Bacteria: Comparison of Continuous Wave and Frequency Modulated Light"; Lasers in Surgery and Medicine; 2002; pp. 343-351; vol. 31; Wiley-Liss, Inc.

Nutku-Bilir et al.; "Interleukin-5 Priming of Human Eosinophils Alters Siglec-8-Mediated Apoptosis Pathways"; Am J Respir Cell Mol Biol; 2008; pp. 121-124; vol. 38.

Nyitrai et al.; "Preparing Stents with Masking & Etching Technology"; 26th International Spring Seminar on Electronics Technology; May 8-11, 2003, Stará Lesná, Slovak Republic; pp. 321-324; IEEE.

Oberreuter et al.; "Identification of coryneform bacteria and related taxa by Fourier-transform infrared (FT-IR) spectroscopy"; International Journal of Systematic and Evolutionary Microbiology; 2002; pp. 91-100; vol. 52; IUMS.

Olafsen et al.; "Covalent disulfide-linked anti-CEA diabody allows site-specific conjugation and radiolabeling for tumor targeting applications"; Protein Engineering, Design & Selection; 2004; pp. 21-27; vol. 17, No. 1; Oxford University Press.

Olson et al.; "Classification of cultured mammalian cells by shape analysis and pattern recognition"; Proc. Natl. Acad. Sci. USA; Mar. 1980; pp. 1516-1520; vol. 77, No. 3.

Ouellette, Jennifer; "Seeing with Sound, Acoustic microscopy advances beyond failure analysis"; The Industrial Physicist; Jun./Jul. 2004; pp. 14-17; American Institute of Physics.

Ozaki et al.; "Cytokine and Cytokine Receptor Pleiotropy and Redundancy"; The Journal of Biological Chemistry; Aug. 16, 2002; pp. 29355-29358; vol. 277, No. 33.

Pachmann et al.; "Quantification of the response of circulating epithelial cells to neodadjuvant treatment for breast cancer: a new tool for therapy monitoring"; Breast Cancer Research; 2005; pp. R975-R979; vol. 7, No. 6; BioMed Central Ltd.

Patel et al.; "Medical Toxicology and Public Health-Update on Research and Activities at the Centers for Disease Control and Prevention and the Agency for Toxic Substances and Disease Registry"; Journal of Medical Toxicology; Jun. 2006; pp. 83-84, vol. 2, No. 2.

Peppas et al.; "Polymers and Gels as Molecular Recognition Agents"; Pharmaceutical Research; May 2002; pp. 578-587; vol. 19, No. 5; Plenum Publishing Corporation.

Pervan et al.; "Proteasome Structures Affected by Ionizing Radiation"; Mol Cancer Res; Jul. 2005; pp. 381-390; vol. 3, No. 7; American Association for Cancer Research.

Pilch et al.; "Unique Ability of Integrin $\alpha_v\beta_3$ to Support Tumor Cell Arrest under Dynamic Flow Conditions"; The Journal of Biological Chemistry; Jun. 14, 2002; pp. 21930-21938; vol. 277, No. 24; The American Society for Biochemistry and Molecular Biology, Inc.

Ponomarenko et al.; "Autoantibodies to myelin basic protein catalyze site-specific degradation of their antigen"; PNAS; Jan. 10, 2006; pp. 281-286; vol. 103, No. 2; The National Academy of Sciences of the USA.

Prescott et al.; "Chronic, programmed polypeptide delivery from an implanted, multireservoir microchip device"; Nature Biotechnology; Apr. 2006; pp. 437-438; vol. 24, No. 4; Nature Publishing Group.

Presterl et al.; "Cytokine Profile and Correlation to the APACHE III and MPM II Scores in Patients with Sepsis"; Am J Respir Crit Care Med; 1997; pp. 825-832; vol. 156.

Price et al.; "Effect of Recombinant Granulocyte Colony-Stimulating Factor on Neutrophil Kinetics in Normal Young and Elderly Humans"; Blood; Jul. 1, 1996; pp. 335-340; vol. 88, No. 1; The American Society of Hematology.

Proske et al.; "Aptamers-basic research, drug development, and clinical applications"; Appl Microbiol Biotechnol; 2005; pp. 367-374; vol. 69; Springer-Verlag.

Raghavan et al.; "BIAcore: a microchip-based system for analyzing the formation of macromolecular complexes"; Structure; Apr. 15, 1995; pp. 331-333; vol. 3; No. 4; Current Biology Ltd.

Rana et al.; "Delivery of apoptotic signal to rolling cancer cells: a novel biomimetic technique using immobilized TRAIL and E-selectin"; Biotechnol Bioeng.; Apr. 15, 2009; pp. 1692-1702; vol. 102, No. 6; Abstract, 1 pg.

Rashid et al.; "Tissue Engineering of a hybrid bypass graft for coronary and lower limb bypass surgery"; The FASEB Journal; 2008; pp. 2084-2089; vol. 22.

Renneisen et al.; "Inhibition of Expression of Human Immunodeficiency Virus-1 in Vitro by Antibody-targeted Liposomes Containing Antisense RNA to the *env* Region"; The Journal of Biological Chemistry; Sep. 25, 1990; pp. 16337-16342; vol. 265, No. 27; The American Society for Biochemistry and Molecular Biology, Inc.

Ribaut et al.; "Concentration and purification by magnetic separation of the erythrocytic stages of all human *Plasmodium* species"; Malaria Journal; 2008; pp. 1-5; vol. 7, No. 45; BioMed Central Ltd.

Rolle et al.; "Increase in number of circulating disseminated epithelial cells after surgery for non-small cell lung cancer monitored by MAINTRAC® is a predictor for relapse: A preliminary report"; World Journal of Surgical Oncology; 2005; pp. 1-9; vol. 3; No. 18; BioMed Central Ltd.

Ross, Gillian; "Accelerated partial breast irradiation: technically feasible but who will benefit?"; Breast Cancer Research; May 2005; pp. 110-112; vol. 7, No. 3; BioMed Central Ltd.

Rossetti et al.; "Immobilization and Detection of Functionalized Nanocontainers on (Patterned) Surfaces"; European Cells and Materials; 2003; p. 83; vol. 6, Suppl. 1.

Roufosse, Florence; "Hypereosinophilic syndrome variants: diagnostic and therapeutic considerations"; Haematologica; 2009; pp. 1188-1193; vol. 94, No. 9.

Sage et al.; "A Rapid and Nondestructive Method for Microbiological Testing in Pharmaceutical Manufacturing"; American Biotechnology Laboratory; Nov./Dec. 2006; pp. 1-5.

Samia et al.; "Quantum Dot-based Energy Transfer: Perspectives and Potential for Applications in Photodynamic Therapy"; Photochemistry and Photobiology; 2006; pp. 617-625; vol. 82; American Society for Photobiology.

Schenk et al.; "Acoustic Microscopy of Red Blood Cells"; The Journal of Histochemistry and Cytochemistry; 1988; pp. 1341-1351; vol. 36, No. 10; The Histochemical Society, Inc.

Schuster et al.; "Circulating Tumor Cells as Prognostic Factor for Distant Metastases and Survival in Patients with Primary Uveal Melanoma"; Clin Cancer Res; Feb. 15, 2007; pp. 1171-1178; vol. 13, No. 4; American Association for Cancer Research.

Serebrovskaya et al.; "Targeting cancer cellS by using an antireceptor antibody-photosensitizer fusion protein"; PNAS; Jun. 9, 2009; pp. 9221-9225; vol. 106, No. 23.

Shangguan et al.; "Aptamers evolved from live cells as effective molecular probes for cancer study"; PNAS; Aug. 8, 2006; pp. 11838-11843; vol. 103, No. 32; The National Academy of Sciences of the USA.

Snow et al.; "Chemical Detection with a Single-Walled Carbon Nanotube Capacitor"; Science; Mar. 25, 2005; pp. 1942-1945; vol. 307.

Son et al.; "An Implantable Wireless Microdosimeter for Radiation Oncology"; MEMS 2008, Tucson, AZ, USA; Jan. 13-17, 2008; pp. 256-259; IEEE.

Soria et al.; "Molecular Detection of Telomerase-positive Circulating Epithelial Cells in Metastatic Breast Cancer Patients"; Clinical Cancer Research; May 1999; pp. 971-975; vol. 5.

Spear et al.; "Isolation, characterization, and recovery of small peptide phage display epitopes selected against viable malignant glioma cells"; Cancer Gene Therapy; 2001; pp. 506-511; vol. 8, No. 7; Nature Publishing Group.

Stojanovic et al.; "Aptamer-Based Folding Fluorescent Sensor for Cocaine"; J. Am. Chem. Soc.; 2001; pp. 4928-4931; vol. 123, No. 21; American Chemical Society.

Stork et al.; "A novel tri-functional antibody fusion protein with improved pharmacokinetic properties generated by fusing a bispecific single-chain diabody with an albumin-binding domain from streptococcal protein G"; Protein Engineering, Design & Selection; 2007; pp. 569-576; vol. 20, No. 11; Oxford University Press.

Stubbe et al.; "'Programmed Polymeric Devices' for Pulsed Drug Delivery"; Pharmaceutical Research; Oct. 2004; pp. 1732-1740; vol. 21, No. 10; Springer Science+Business Media, Inc.

Szodoray et al.; "Programmed Cell Death in Rheumatoid Arthritis Peripheral Blood T-Cell Subpopulations Determined by Laser Scanning Cytometry"; Laboratory Investigation; Dec. 2003; pp. 1839-1848; vol. 83, No. 12; The United States and Canadian Academy of Pathology, Inc.

Takemura et al.; "Construction of a diabody (small recombinant bispecific antibody) using a refolding system"; Protein Engineering; 2000; pp. 583-588; vol. 13, No. 8; Oxford University Press.

Tamura et al.; "One-chip sensing device (biomedical photonic LSI) enabled to assess hippocampal steep and gradual up-regulated proteolytic activities"; Journal of Neuroscience Methods; 2008; pp. 114-120; vol. 173; Elsevier B.V.

Terstappen et al.; "Four-Parameter White Blood Cell Differential Counting Based on Light Scattering Measurements"; Cytometry; 1988; pp. 39-43; vol. 9, Alan R. Liss, Inc.

Tsen et al.; "Inactivation of viruses by coherent excitations with a low power visible femtosecond laser"; Virology Journal; 2007; pp. 1-6 (the accurate page numbers are 1-5); vol. 4, No. 50; BioMed Central Ltd.

Tseng et al.; "Inactivation of Viruses on Surfaces by Ultraviolet Germicidal Irradiation"; Journal of Occupational and Environmental Hygiene; Jun. 2007; pp. 400-405; vol. 4; JOEH, LLC.

Ueda et al.; "Increased Plasma Levels of Adrenomedullin in Patients with Systemic Inflammatory Response Syndrome"; Am J Respir Crit Care Med; 1999; pp. 132-136; vol. 160.

Ulrich et al.; "In Vitro Selection of RNA Aptamers That Bind to Cell Adhesion Receptors of *Trypanosoma cruzi* and Inhibit Cell Invasion"; The Journal of Biological Chemistry; Jun. 7, 2002; pp. 20756-20762; vol. 277, No. 23; The American Society for Biochemistry and Molecular Biology, Inc.

Vashist, Sandeep Kumar; "A Review of Microcantilevers for Sensing Applications"; AZojono Journal of Nanotechnology Online; Jun. 2007; pp. 1-15; vol. 3.

Vodovotz et al.; "Mathematical models of the acute inflammatory response"; Current Opinion in Critical Care; 2004; pp. 383-390; vol. 10; Lippincott Williams & Wilkins.

Vodovotz et al.; "Translational Systems Biology of Inflammation"; PLoS Computational Biology; Apr. 2008; pp. 1-6; vol. 4, No. 4.

Vučković et al.; "Gamma-radiation induced damage of proteins in the thick fraction of egg white"; J. Serb. Chem. Soc.; 2005; pp. 1255-1262; vol. 70, No. 11.

Walsh et al.; "Atmospheric Dielectric-Barrier Discharges Scalable From 1 mm to 1 m"; IEEE Transactions on Plasma Science; Aug. 2008; pp. 1314-1315; vol. 36, No. 4; IEEE.

Wang et al.; "Time course of plasma gelsolin concentrations during severe sepsis in critically ill surgical patients"; Critical Care; 2008; pp. 1-6; vol. 12, No. 4; BioMed Central Ltd.

Weatherall et al.; "Malaria and the Red Cell"; Hematology; 2002; pp. 35-57.

Wentworth et al.; "Antibodies have the intrinsic capacity to destroy antigens"; PNAS; Sep. 26, 2000; pp. 10930-10935; vol. 97, No. 20.

Wentworth, Jr. et al.; "Antibody Catalysis of the Oxidation of Water"; Science; Sep. 7, 2001; pp. 1806-1811; vol. 293.

Wentworth, Jr., Paul; "Antibody Design by Man and Nature"; Science; Jun. 21, 2002; pp. 2247-2249; vol. 296.

Win et al.; "Codeine-binding RNA aptamers and rapid determination of their binding constants using a direct coupling surface plasmon resonance assay"; Nucleic Acids Research; 2006; pp. 5670-5682; vol. 34, No. 19.

Wissing et al.; "Illumination of the Malaria Parasite *Plasmodium falciparum* Alters Intracellular pH"; The Journal of Biological Chemistry; Oct. 4, 2002; pp. 37747-37755; vol. 277, No. 40; The American Society for Biochemistry and Molecular Biology, Inc.

Wojciechowski et al.; "Capture and enrichment of CD34-positive haematopoietic stem and progenitor cells from blood circulation using P-selectin in an implantable device"; British Journal of Haematology; 2008; pp. 673-681; vol. 140, No. 6; Blackwell Publishing Ltd.

Wygant et al.; "Photoacoustic Imaging Using a Two-Dimensional CMUT Array"; IEEE Ultrasonics Symposium; 2005; pp. 1921-1924.

Yang et al.; "On-Chip Electrochemical Impedance Spectroscopy for Biosensor Arrays"; IEEE Sensors 2006, EXCO, Daegu, Korea; Oct. 22-25, 2006; pp. 93-96.

Yang et al.; "Engineering Target-Responsive Hydrogels Based on Aptamer-Target Interactions"; J. Am. Chem. Soc.; 2008; pp. 6320-6321; vol. 130, No. 20; American Chemical Society.

Ye et al.; "Molecularly imprinted polymers as antibody and receptor mimics for assays, sensors and drug discovery"; Anal Bioanal Chem; 2004; pp. 1887-1897; vol. 378; Springer-Verlag.

Yeo et al.; "Bactericidal effects of high-power Nd:YAG laser radiation on *Staphylococcus aureus*"; Pure Appl. Opt.; 1998; pp. 643-655; vol. 7; IOP Publishing Ltd.

Yokota et al.; "Micro-Machined Stent-Type Flow Sensor for Evaluation of Nasal Respiration"; IEEE; 2009; pp. 495-498.

Yusa et al.; "Controlled multiple quantum coherences of nuclear spins in a nanometre-scale device"; Nature; Apr. 21, 2005; pp. 1001-1005; vol. 434; Nature Publishing Group.

Zenker et al.; "From Inverse Problems in Mathematical Physiology to Quantitative Differential Diagnoses"; PLoS Computational Biology; Nov. 2007; pp. 2072-2086; vol. 3, No. 11.

Zharov et al.; "In vivo high-speed imaging of individual cells in fast blood flow"; Journal of Biomedical Optics; Sep./Oct. 2006; pp. 054034-1-054034-4; vol. 11, No. 5; SPIE.

Zharov et al.; "In Vivo Photothermal Flow Cytometry: Imaging and Detection of Individual Cells in Blood and Lymph Flow"; Journal of Cellular Biochemistry; 2006; pp. 916-932; vol. 97; Wiley-Liss, Inc.

Zharov et al.; "Photoacoustic flow cytometry monitors cells circulating in vivo"; The International Society for Optical Engineering; 2006; pp. 1-3; SPIE.

Zheng et al.; "Design and Fabrication of a Micro Coulter Counter with Thin Film Electrodes"; Proceedings of 2006 International Conference on Microtechnologies in Medicine and Biology; May 9-12, 2006; pp. 16-19; IEEE.

Zhou et al.; "Predicting short-term disease progression among HIV-infected patients in Asia and the Pacific region: preliminary results from the TREAT Asia HIV Observational Database (TAHOD)"; HIV Medicine; 2005; pp. 216-223; vol. 6; British HIV Association.

Ng, David C. et al.; Real time in vivo imaging and measurement of serine protease activity in the mouse hippocampus using a dedicated complementary metal-oxide semiconductor imaging device; Journal of Neuroscience Methods; 2006; pp. 23-30; vol. 156; Elsevier B.V.

Arndt et al.; "Microwave Radiation-Therapeutic Application for Cure of Subcutaneous Bacterial Infections"; Space Life Science; 2005; 2 pgs.; NASA Biennial Research and Technology Report. National Aeronautics and Space Administration, Houston, TX.

Baddour et al.; "High Frequency Ultrasound Imaging of Changes in Cell Structure Including Apoptosis"; created on Oct. 7, 2002; 6 pgs.

Bartels et al.; "Use of diode laser energy (808 nm) for selective photothermolysis of contaminated wounds"; Proc. SPIE; 1995; pp. 602-606; vol. 2395; located at http://dx.doi.org/10.1117/12.209149.

Sapi et al.; "Detection of telomerase-positive circulating epithelial cells in ovarian cancer patients"; Cancer Detection and Prevention; May 2002; pp. 158-167; vol. 26, No. 2; Abstract; 1 pg.; Elsevier B.V.

Schneider et al.; "Automated Image Processing System for Shape Recognition of Single Red Blood Cells Based on Out-of-Focus Images"; Biorheology, Mar. 1995; pp. 237-238; vol. 32, No. 2; Elsevier.

\* cited by examiner $x_1, x_2, x_3, x_4 \ldots =$ concentrations of target cell $X$ $y_1, y_2, y_3, y_4 \ldots =$ concentrations of target cell $Y$ $\sigma_1, \sigma_2, \sigma_3 \ldots =$ standard deviation $$f = \frac{(x_1 - y_1)^2}{(\sigma_1)^2} + \frac{(x_2 - y_2)^2}{(\sigma_2)^2} + \frac{(x_3 - y_3)^2}{(\sigma_3)^2} + \cdots$$

FIGURE 5
FIG. 5A
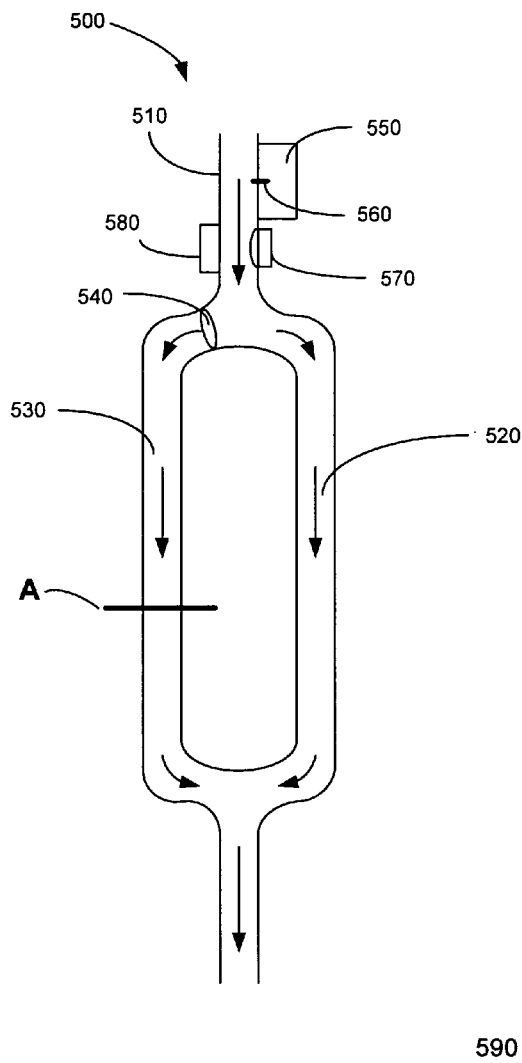
FIG. 5B
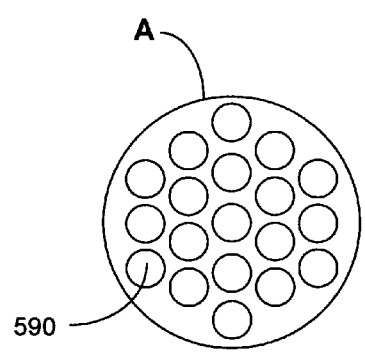

DEVICE FOR ACTIVELY REMOVING A TARGET COMPONENT FROM BLOOD OR LYMPH OF A VERTEBRATE SUBJECT

RELATED APPLICATIONS

For purposes of the USPTO extra-statutory requirements, the present application constitutes a continuation-in-part of U.S. patent application Ser. No. 12/380,399, entitled DEVICE, SYSTEM, AND METHOD FOR CONTROLLABLY REDUCING INFLAMMATORY MEDIATORS IN A SUBJECT, naming Roderick A. Hyde, Muriel Y. Ishikawa, Edward K. Y. Jung, Robert Langer, Eric C. Leuthardt, Nathan P. Myhrvold, Elizabeth A. Sweeney and Lowell L. Wood, Jr. as inventors, filed 25 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/380,400, entitled DEVICE, SYSTEM, AND METHOD FOR CONTROLLABLY REDUCING INFLAMMATORY MEDIATORS IN A SUBJECT, naming Roderick A. Hyde, Muriel Y. Ishikawa, Edward K. Y. Jung, Robert Langer, Eric C. Leuthardt, Nathan P. Myhrvold, Elizabeth A. Sweeney and Lowell L. Wood, Jr. as inventors, filed 25 Feb. 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/660,926, entitled DEVICE FOR PASSIVELY REMOVING A TARGET COMPONENT FROM BLOOD OR LYMPH OF A VERTEBRATE SUBJECT, naming Roderick A. Hyde, Muriel Y. Ishikawa, Edward K. Y. Jung, Robert Langer, Eric C. Leuthardt, Nathan P. Myhrvold, Elizabeth A. Sweeney and Lowell L. Wood, Jr. as inventors, filed 5 Mar. 2010, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/660,928, entitled DEVICE FOR ACTIVELY REMOVING A TARGET CELL FROM BLOOD OR LYMPH OF A VERTEBRATE SUBJECT, naming Roderick A. Hyde, Muriel Y. Ishikawa, Edward K. Y. Jung, Robert Langer, Eric C. Leuthardt, Nathan P. Myhrvold, Elizabeth A. Sweeney and Lowell L. Wood, Jr. as inventors, filed 5 Mar. 2010 now U.S. Pat. No. 8,167,871, which is currently co-pending, or is an application of which a currently co-pending application is entitled to the benefit of the filing date.

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

SUMMARY

Devices, systems, and methods are disclosed herein for controlling or modulating the levels of one or more target components in the blood and/or lymph of a vertebrate subject. The device or system is useful in a method for treating a disease and/or condition mediated by or indicated by the one or more target components. The one or more target components include, but are not limited to, cellular components (e.g., blood cells, cancer cells, pathogens), non-cellular components (e.g., proteins, lipids, sugars, carbohydrates, small molecules), or combinations thereof. An implantable device is provided which includes a body defining at least one lumen configured for fluid flow; at least one first reservoir in communication with the at least one lumen; one or more energy sources configured to provide energy to elicit one or more signal responses associated with one or more labels that bind to one or more target components in one or more of blood fluid or lymph fluid of the vertebrate subject; one or more sensors configured to detect the one or more signal responses associated with one or more labeled target components; and one or more reactive components in communication with the at least one lumen and for release responsive to the one or more sensors, wherein the one or more reactive components are configured to modulate a physiological effect of the one or more target components in the one or more of blood fluid or lymph fluid of the vertebrate subject. The one or more reactive components can be configured to alter, arrest, disrupt, destroy, inactivate, or ablate the one or more target components.

Examples of diseases or conditions include, but are not limited to, acute and chronic inflammatory diseases (e.g., sepsis, multiple organ dysfunction syndrome, autoimmune disease, asthma, rhinitis, rheumatoid arthritis), cardiovascular disease, gastrointestinal disease, cancer, metabolic disease, bacterial infection (e.g., *Staphylococcus* bacteremia), viral infection (e.g., acquired immunodeficiency syndrome, hepatitis), parasite infection (e.g., malaria), or chemical or biological agent exposure (e.g., drug overdose, environmental toxin).

In an aspect, the device including the at least one first reservoir can include the one or more labels. In an aspect, at least one of the at least one first reservoir can include a first gated mechanism responsive to the one or more sensors and configured to release the one or more labels into the one or more of blood fluid or lymph fluid of the vertebrate subject. At least one of the at least one first reservoir can include a first gated mechanism responsive to the one or more sensors and configured to expose the one or more labels to the one or more of blood fluid or lymph fluid of the vertebrate subject. At least one of the at least one first reservoir can be disposed within the at least one lumen. The one or more signal responses can include one or more of electromagnetic signal response, optical signal response, visible light signal response, infrared signal response, signal image response, fluorescent signal response, radiofrequency signal response, magnetic signal responses, or surface plamon resonance response. The one or more signal responses can further include one or more signal responses associated with an interior of the at least one lumen. The one or more signal responses can be associated with an interior of the one or more of a blood vessel or a lymph vessel of the vertebrate subject. The one or more labeled target components can include one or more of circulating cells or circulating emboli. The one or more labeled target components can include one or more of tumor cells, emboli, misfolded proteins, aggregated proteins, autoimmune antibodies, infectious agents, or infected cells. The one or more labeled target components can include one or more labeled target cells. The one or more labeled target components can include one or more of cancer cells, autoimmune-related cells, B cells, T cells, parasites, viruses, bacteria, fungi, or infected cells. In an aspect, the one or more labeled target components can include an intracellular target component. The intracellular target component can be modified by parasite infection, viral infection, or bacterial infection. The intracellular target component can be unmodified by an infectious agent.

The device including the one or more sensors can be configured to detect the labeled target cell prior to obtaining a high resolution image of the labeled target cell. The one or more sensors can be configured to correlate the target cell image and the detected label. The one or more sensor can be configured to function in, or proximal to, the one or more blood vessel or lymph vessel. The one or more sensor can be external to the at least one lumen. The one or more sensor can be internal to the at least one lumen. The one or more labels can include one or more of a fluorescent label, electromagnetic-emitting label, magnetic label, electromagnetic label, paramagnetic label, quantum dot label, aptamer label, gold label, radioactive label, radiometrically-discernible label, or prodrug.

In an aspect, the device can include a single unit. In an aspect, the device can include two or more separate units. In an aspect, the device can be configured to report to an outside source or to a computing device, and the device can be configured to report the detected one or more signal responses associated with the one or more labeled target components. In an aspect, the device can further include two or more parallel lumen configured to receive the one or more target components. In an aspect, a diameter of each of the two or more parallel lumen can be approximately less than two cell diameters. The diameter of each of the two or more parallel lumen can be approximately less than 10 μm. The two or more parallel lumen can further include 100 or more parallel lumen. The two or more parallel lumen can further include 1000 or more parallel lumen. The two or more parallel lumen can further include 10,000 or more parallel lumen. In an aspect, the device is configured to be placed relative to a tumor or an organ in the vertebrate subject.

The device including the at least one second reservoir can include a second gated mechanism responsive to the one or more sensors and configured to release the one or more reactive components. The at least one second reservoir can include a second gated mechanism responsive to the one or more sensors and configured to expose the one or more reactive components. The one or more reactive components can include one or more reactive chemical components. The one or more reactive chemical components can include one or more of a binding molecule, antibody, binding mimetic, synthetic polymer, lectin, integrin, or selectin. The one or more reactive chemical components can be configured to produce necrosis or apoptosis in the one or more labeled target components. The one or more reactive chemical components can include one or more of a denaturing agent, degradative agent, or binding agent. The one or more reactive chemical components can be configured to bind to the at least one lumen or are configured to be released into the at least one lumen. The one or more binding agents can include one or more of antibodies, receptors, or cognates configured to bind to one or more labeled target components. The one or more binding agents can include one or more of lectin, binding protein, catalytic antibody, catalytic aptamer, protease, or photoactivatable agent. The one or more denaturing agents can include at least of an acid, base, solvent, detergent, cross-linking agent, chaotropic agent, disulfide bond reducer, enzyme, drug, cell, or radical ion. The one or more degradative agents can include at least one of an enzyme, coenzyme, enzyme complex, catalytic antibody, protease, lipase, proteasomal component, strong acid, strong base, radical, photoactivatable agent, drug, cell, or radical ion. The catalytic antibody can generate a radical ion.

In an aspect, the device including the one or more reactive components can include one or more reactive components within at least one second reservoir disposed within the at least one lumen. In an aspect, the one or more reactive components can include, but are not limited to, one or more reactive chemical components, one or more reactive biologic components, or one or more reactive physical components. The one or more reactive components can include one or more reactive biologic components. The one or more reactive biologic components can include one or more phagocytic cell types. The one or more second reservoirs can include a source for producing the one or more reactive biologic components. The source can include at least one producer. The at least one producer can include at least one encapsulated cell. The at least one encapsulated cell can produce the one or more reactive biologic components. The at least one encapsulated cell can include at least one genetically engineered cell. The at least one encapsulated cell can include at least one of a mammalian cell, bacterial cell, yeast cell, plant cell, insect cell, artificial cell, or enucleated cell. The at least one encapsulated cell can include one or more of a myeloid cell; lymphocyte, or precursor thereof. The at least one encapsulated cell can include one or more of a T-lymphocyte, B-lymphocyte, macrophage, monocyte, neutrophil, or NK cell. The one or more reactive biologic components can include a protein, lipid micelle, liposome, polymer, a catalytic antibody, or a combination thereof. The catalytic antibody can include a radical ion generator. The one or more reactive components can include one or more reactive physical components. The one or more reactive physical components can include one or more of polymers, imprinted polymers, or charged polymers.

In an aspect, the device can further include at least one controllable flow barrier to the at least one lumen. In an aspect, the device can further include at least one controller in communication with the one or more sensors, and in communication with the at least one controllable flow barrier to the at least one lumen, wherein the controller is configured to control flow of the one or more of blood fluid or lymph fluid through the at least one lumen. The at least one controller can include a processor. The at least one first reservoir can be responsive to the at least one controller. The one or more energy sources can be responsive to the at least one controller. The one or more second reservoirs can be responsive to the at least one controller. The at least one controller can be configured to control flow of the one or more of blood fluid or lymph fluid based on the one or more signal responses associated with the one or more labeled target components. The at least one controller can be configured to control flow of the one or more of blood fluid or lymph fluid based on the label on the one or more target components. The at least one controller is configured to control flow of the one or more of blood fluid or lymph fluid and to control the presence of the one or more reactive chemical components in the one or more second reservoirs based on the label on the one or more target components.

In an aspect, the device can further include at least one controller in communication with the one or more sensors, and in communication with the one or more energy sources, wherein the at least one controller is configured to control the one or more energy sources configured to provide energy to elicit one or more signal responses. In an aspect, the device can further include at least one controller in communication with the one or more sensors, wherein the at least one controller is configured to control release of the one or more reactive components configured to modulate the physiological effect of the one or more target components. In an aspect, the device can further include at least one programmable controller in communication With the at least one first reservoir.

In an aspect, the device including the at least one controller and the one or more sensors can be configured to control levels of the one or more target components to substantially attain a target level of the one or more target components in the one or more of blood fluid or lymph fluid of the vertebrate subject. The one or more sensors and the at least one controller can be configured to control levels of the detected one or more target components to limit a deviation from the target level. The deviation can be determined by a weighted least squares fit. The target level can include a desired concentration of the one or more target components in the one or more of blood fluid or lymph fluid. The target level can include a desired range of concentrations of the one or more target components in the one or more of blood fluid or lymph fluid. The target level can include a desired ratio of concentrations of two or more target components in the one or more of blood fluid or lymph fluid. The target level can include a desired ratio of levels of two or more target components in the one or more of blood fluid or lymph fluid. The one or more sensors can include a biosensor, chemical sensor, physical sensor, or optical sensor. The one or more sensors can include one or more of an aptamer, antibody, or receptor. The one or more sensors can include one or more of a recognition-based substrate, an aptamer-based substrate, an antibody-based substrate, surface plasmon resonance, genetically modified cells, or genetically modified cells with receptor-linked signaling. The genetically modified cells can include receptor-linked signaling by fluorogen-activating proteins. The one or more sensors can be configured to target the device to a site having an elevated level of the target components. The one or more sensors can be configured to detect one or more of cytokines, T-lymphocytes, B-lymphocytes, antibodies, tumor cells, inflammatory cells, infected cells, bacteria, parasites, fungi, or viruses. The one or more sensors can be further configured to detect one or more of body temperature, vital signs, edema, oxygen level, pathogen level, or toxin level of the subject. The one or more sensors can be configured to detect one or more of anaphylatoxin, cytokine, chemokine, leukotriene, prostaglandin, complement, coagulation factor, or proinflammatory cytokine. The one or more sensors can be configured to detect one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin.

In an aspect, the device including the one or more binding agents are on a matrix adapted to the at least one second reservoirs, wherein the one or more binding agents are configured to sequester at least one of the one or more target components from the one or more of blood fluid or lymph fluid. The one or more binding agents can include one or more of antibodies, receptors, or cognates configured to bind to at least one of the one or more target components. The matrix can include one or more of a specific binding ligand or a hydrophobic surface. The specific binding ligand or the hydrophobic surface can include one or more of nucleic acid aptamers, peptide aptamers, molecular imprinting polymer, antibodies or fragments thereof, high affinity mimetics, synthetic binding molecules, or receptor binding molecules. The matrix can include one or more of beads, cells, vesicles, filters, hydrogel polymers, microparticles, nanoparticles, adsorbent, or synthetic polymers. The matrix can include one or more of a lectin, binding protein, receptor, antibody, catalytic antibody, catalytic aptamer, enzyme, protease conjugate, or photoactivatable agent conjugate.

In an aspect, the device is intracorporeal. The device can be configured to be implanted. The device can include a stent, bypass implant, nanostructure or microstructure. The device can be configured to be implanted relative to an organ or tissue in the subject.

In an aspect, the device can be at least partially extracorporeal. The extracorporeal device can include a dialysis device, hemoperfusion device, apheresis device, intravenous device, shunt device, or patch device. The device can be tethered to the blood vessel or the lymph vessel of the vertebrate subject. The device can be untethered to the blood vessel or the lymph vessel of the vertebrate subject.

A method for treating an inflammatory disease or condition in a vertebrate subject is provided which includes binding one or more target components with at least one label in one or more of blood fluid or lymph fluid of the vertebrate subject; providing energy to elicit one or more signal responses associated with one or more labeled target components; detecting the one or more signal responses associated with the one or more labeled target components; and providing one or more reactive components to modulate a physiological effect of the one or more target components in the one or more of blood fluid or lymph fluid of the vertebrate subject. A method for treating or modulating an infectious disease or condition in a vertebrate subject is provided. A method for treating or modulating a neoplastic disease or condition in a vertebrate subject is provided.

In an aspect, the method can further include controlling flow of the one or more of blood fluid or lymph fluid through the at least one lumen with at least one controllable flow barrier. The method can further include controlling flow of the one or more of blood fluid or lymph fluid through the at least one lumen with at least one controller in communication with one or more sensors and in communication with the at least one controllable flow barrier. The at least one controller can include a processor. The method can further include providing at least one first reservoir including the at least one label, wherein the at least one first reservoir is in communication with a body including at least one lumen configured for fluid flow, and the at least one first reservoir is responsive to at least one controller. The at least one controller can be configured to control flow of the one or more of blood fluid or lymph fluid based on the one or more signal responses associated with the one or more labeled target components. The at least one controller can be configured to control flow of the one or more of blood fluid or lymph fluid based on the label on the one or more target components. The at least one controller can be configured to control flow of the one or more of blood fluid or lymph fluid and to control the presence of the one or more reactive components based on the label on the one or more target components. The one or more reactive components can alter, arrest, disrupt, destroy, inactivate or ablate the one or more target components.

In an aspect, the method can further include controlling one or more energy sources with at least one controller in communication with one or more sensors, wherein the at least one controller is configured to control the one or more energy sources configured to provide the energy to elicit the one or more signal responses associated with the one or more labeled target components. In an aspect, the method can further include controlling release of one or more reactive components with at least one controller in communication with one or more sensors, wherein the at least one controller is configured to control release of the one or more reactive components configured to modulate the physiological effect of the one or more target components. The one or more sensors and at least one controller can be configured to control levels of the one or more target components to substantially attain a target level of the one or more target components in the one or more of blood fluid or lymph fluid of the vertebrate subject. The one or more sensors and the at least one controller can be configured to control levels of the detected one or more target components to limit a deviation from the target level. The deviation can be determined by a weighted least squares fit. The target level can include a desired concentration of the one or more target components in the one or more of blood fluid or lymph fluid. The target level can include a desired range of concentrations of the one or more target components in the one or more of blood fluid or lymph fluid. The target level can include a desired ratio of concentrations of two or more target components in the one or more of blood fluid or lymph fluid. The target level can include a desired ratio of levels of two or more target components in the one or more of blood fluid or lymph fluid.

In an aspect, the method including the at least one first reservoir can include the one or more labels. In an aspect, at least one of the at least one first reservoir can include a first gated mechanism responsive to the one or more sensors and configured to release the one or more labels into the one or more of blood fluid or lymph fluid of the vertebrate subject. In an aspect, at least one of the at least one first reservoir can include a first gated mechanism responsive to the one or more sensors and configured to expose the one or more labels to the one or more of blood fluid or lymph fluid of the vertebrate subject. In an aspect, at least one of the at least one first reservoir can be disposed within the at least one lumen. The one or more signal responses can further include one or more signal responses associated with an interior of the at least one lumen. The one or more signal responses can be associated with an interior of one or more of a blood vessel or a lymph vessel of the vertebrate subject. The one or more labeled target components can include one or more of circulating cells or circulating emboli. The one or more labeled target components can include one or more of tumor cells, emboli, misfolded proteins, aggregated proteins, autoimmune antibodies, infectious agents, or infected cells.

The method including the one or more labeled target components can include one or more labeled target cells. The one or more labeled target components can include cancer cells, autoimmune-related cells, B cells, T cells, parasites, viruses, bacteria, fungi, or infected cells. The one or more sensors can be configured to detect the labeled target cell prior to obtaining a high resolution image of the labeled target cell. The one or more sensors can be configured to correlate the target cell image and the detected label. The one or more sensors can be configured to function in, or proximal to, the one or more blood vessel or lymph vessel. The one or more sensors can be external to the at least one lumen. The one or more sensors can be internal to the at least one lumen. In an aspect, the one or more labels include a fluorescent label, electromagnetic-emitting label, magnetic label, electromagnetic label, paramagnetic label, quantum dot label, aptamer label, gold label, radioactive label, radiometrically-discernible label, or prodrug.

In an aspect, the method can further include two or more parallel lumen configured to receive the one or more target components. A diameter of each of the two or more parallel lumen can be approximately less than two cell diameters. A diameter of each of the two or more parallel lumen can be approximately less than 10 μm. The two or more parallel lumen can further include 100 or more parallel lumen. The two or more parallel lumen can further include 1000 or more parallel lumen. The two or more parallel lumen can further include 10,000 or more parallel lumen.

In an aspect, the method can further include placing a device including the one or more reactive components relative to a tumor or an organ in the vertebrate subject. In an aspect, the one or more reactive component can be configured within at least one second reservoir. At least one of the at least one second reservoir can be disposed within at least one lumen. The at least one second reservoir can include a second gated mechanism responsive to the one or more sensors and configured to release the one or more reactive components. The at least one second reservoir can include a second gated mechanism responsive to the one or more sensors and configured to expose the one or more reactive components. In an aspect, the one or more reactive components can include one or more reactive chemical components. The one or more reactive chemical components can include one or more of adhesion binding molecule, antibody, binding mimetic, polymer, lectin, integrin, or selectin. The one or more reactive chemical components can be configured to produce necrosis or apoptosis in the one or more labeled target components. The one or more reactive chemical components can be configured to bind to at least one lumen or are configured to be released into the at least one lumen. The one or more reactive chemical components can include one or more of a denaturing agent, degradative agent, or binding agent. The one or more binding agents can include one or more of antibodies, receptors, or cognates configured to bind to one or more labeled target components. The one or more binding agents can include one or more of lectin, binding protein, catalytic antibody, catalytic aptamer, protease, or photoactivatable agent. The one or more denaturing agents can include at least of an acid, base, solvent, detergent cross-linking agent, chaotropic agent, disulfide bond reducer, enzyme, drug, cell, or radical ion. The one or more degradative agents can include at least one of an enzyme, coenzyme, enzyme complex, catalytic antibody, protease, lipase, proteasomal component, strong acid, strong base, radical, photoactivatable agent, drug, cell, or radical ion. The catalytic antibody can generate a radical ion.

In an aspect, the method including the one or more reactive components can include one or more reactive biologic components. The one or more reactive biologic components can include one or more phagocytic cell types. The at least one second reservoirs can include a source for producing the one or more reactive biologic components. The source includes at least one producer. The at least one producer can include at least one encapsulated cell. The at least one encapsulated cell can produce the one or more reactive biologic components. The at least one encapsulated cell can include at least one genetically-engineered cell. The at least one encapsulated cell can include at least one of a mammalian cell, bacterial cell, yeast cell, plant cell, insect cell, artificial cell, or enucleated cell. The at least one encapsulated cell can include one or more of a myeloid cell, lymphocyte, or precursor thereof. The at least one encapsulated cell can include one or more of a T-lymphocyte, B-lymphocyte, macrophage, monocyte, neutrophil, or NK cell. The one or more reactive biologic components can include a protein, lipid micelle, liposome, polymer, catalytic antibody, or a combination thereof. The catalytic antibody can include a radical ion generator. In an aspect, the one or more reactive components can include one or more reactive physical components. The one or more reactive physical components can include one or more of polymers, imprinted polymers, or charged polymers.

In an aspect, the method including the one or more sensors can include a biosensor, chemical sensor, physical sensor, or optical sensor. The one or more sensors can include one or more of an aptamer, antibody, or receptor. The one or more sensors can include one or more of a recognition-based substrate, an aptamer-based substrate, an antibody-based substrate, surface plasmon resonance, genetically-modified cells, or genetically-modified cells with receptor-linked signaling. The genetically-modified cells can include receptor-linked signaling by fluorogen-activating proteins. The one or more sensors can be configured to target a device to a site having an elevated level of the target components. The one or more sensors can be configured to detect one or more of cytokines, T-lymphocytes, B-lymphocytes, antibodies, tumor cells, inflammatory cells, infected cells, bacteria, parasites, fungi, or viruses. The one or more sensors can be configured to detect one or more of body temperature, vital signs, edema, oxygen level, pathogen level, or toxin level of the subject. The one or more sensors can be configured to detect one or more of anaphylatoxin, cytokine, chemokine, leukotriene, prostaglandin, complement, coagulation factor, or proinflammatory cytokine. The one or more sensors can be configured to detect one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin.

In an aspect, the method including the one or more binding agents can be on a matrix adapted to the one or more second reservoirs, wherein the one or more binding agents can be configured to sequester at least one of the one or more target components from the one or more of blood fluid or lymph fluid. The one or more binding agents can include one or more of antibodies, receptors, or cognates configured to bind to at least one of the one or more target components. The matrix can include one or more of a specific binding ligand or a hydrophobic surface. The specific binding ligand or the hydrophobic surface can include one or more of nucleic acid aptamers, peptide aptamers, molecular imprinting polymer, antibodies or fragments thereof, high affinity mimetics, synthetic binding molecules, or receptor binding molecules. The matrix can include one or more of beads, cells, vesicles, filters, hydrogel polymers, microparticles, nanoparticles, adsorbent, or synthetic polymers. The matrix can include one or more of a lectin, binding protein, receptor, antibody, catalytic antibody, catalytic aptamer, protease conjugate, or photoactivatable agent conjugate.

A method for modulating an inflammatory disease or condition in a vertebrate subject is provided which includes binding one or more target components with at least one label in one or more of blood fluid or lymph fluid of the vertebrate subject; providing energy to elicit one or more signal responses associated with one or more labeled target components; detecting the one or more signal responses associated with the one or more labeled target components; and providing one or more reactive chemical components to modulate a physiological effect of the one or more labeled components in the one or more of blood fluid or lymph fluid of the vertebrate subject.

A method for treating an infectious disease or condition in a vertebrate subject is provided which includes binding one or more target components with at least one label in one or more of blood fluid or lymph fluid of the vertebrate subject; providing energy to elicit one or more signal responses associated with one or more labeled target components; detecting the one or more signal responses associated with the one or more labeled target components; and providing one or more reactive chemical components to modulate a physiological effect of the one or more labeled components in the one or more of blood fluid or lymph fluid of the vertebrate subject.

A method for treating a neoplastic disease or condition in a vertebrate subject is provided which includes binding one or more target components with at least one label in one or more of blood fluid or lymph fluid of the vertebrate subject; providing energy to elicit one or more signal responses associated with one or more labeled target components; detecting the one or more signal responses associated with the one or more labeled target components; and providing one or more reactive chemical components to modulate a physiological effect of the one or more labeled components in the one or more of blood fluid or lymph fluid of the vertebrate subject.

A system is provided which includes at least one computer program included on a computer-readable medium for use with at least one computer system wherein the computer program includes a plurality of instructions including one or more instructions for determining at least one treatment of a vertebrate subject through an implantable device including one or more instructions for receiving data including data for delivering a body defining at least one lumen configured for fluid flow; one or more instructions for receiving data including data from at least one first reservoir disposed within the at least one lumen; one or more instructions for receiving data including data from one or more energy sources configured to provide energy to elicit one or more signal responses associated with one or more labels that bind to one or more target components in one or more of blood fluid or lymph fluid of the vertebrate subject; one or more instructions for receiving data including data from one or more sensors configured to detect the one or more signal responses associated with one or more labeled target components; and one or more instructions for receiving data including data regarding one or more reactive components disposed within the at least one lumen for release responsive to the one or more sensors, wherein the one or more reactive components are configured to modulate a physiological effect of the one or more target components in the one or more of blood fluid or lymph fluid of the vertebrate subject. In an aspect, the system can further include one or more instructions for receiving data including data from at least one controllable flow barrier to the at least one lumen. In an aspect, the system can further include one or more instructions for receiving data including data from at least one controller in communication with the one or more sensors, and in communication with the at least one controllable flow barrier to the at least one lumen, wherein the controller is configured to control flow of the one or more of blood fluid or lymph fluid through the at least one lumen. The one or more reactive components can include one or more of the one or more reactive components within at least one second reservoir disposed within the at least one lumen. The one or more reactive components can include one or more of one or more reactive chemical components, one or more reactive biologic components, or one or more reactive physical components within at least one second reservoir disposed within the at least one lumen. A device is provided which includes a system including a signal-bearing medium including, one or more instructions for treatment of a vertebrate subject through an implantable device including one or more instructions for receiving data including data for delivering a body defining at least one lumen configured for fluid flow; one or more instructions for receiving data including data from at least one first reservoir disposed within the at least one lumen; one or more instructions for receiving data including data from one or more energy sources configured to provide energy to elicit one or more signal responses associated with one or more labels that bind to one or more target components in one or more of blood fluid or lymph fluid of the vertebrate subject; one or more instructions for receiving data including data from one or more sensors configured to detect the one or more signal responses associated with one or more labeled target components; and one or more instructions for receiving data including data regarding one or more reactive components disposed within the at least one lumen for release responsive to the one or more sensors, wherein the one or more reactive components are configured to modulate a physiological effect of the one or more target components in the one or more of blood fluid or lymph fluid of the vertebrate subject. In an aspect, the device can further include one or more instructions for receiving data including data from at least one controllable flow barrier to the at least one lumen. In an aspect, the device can further include one or more instructions for receiving data including data from at least one controller in communication with the one or more sensors, and in communication with the at least one controllable flow barrier to the at least one lumen, wherein the controller is configured to control flow of the one or more of blood fluid or lymph fluid through the at least one lumen. The one or more reactive components can include one or more of the one or more reactive components within at least one second reservoir disposed within the at least one lumen. The one or more reactive components can include one or more of one or more reactive chemical components, one or more reactive biologic components, or one or more reactive physical components within at least one second reservoir disposed within the at least one lumen.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 5 depicts a diagrammatic view of an aspect of an embodiment of a device.

DETAILED DESCRIPTION

Figure 1:
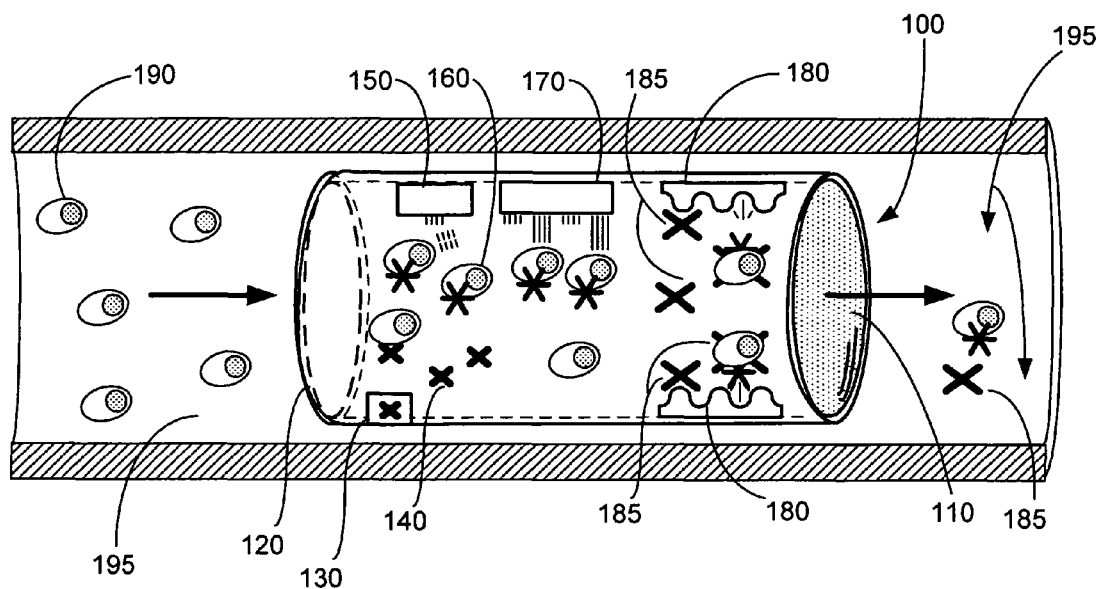
FIG. 1 depicts a diagrammatic view of an aspect of an embodiment of a device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Devices, systems, and methods are disclosed herein for controlling or modulating the levels of one or more target components in the blood fluid and/or lymph fluid of a vertebrate subject. The device or system is useful in a method for treating a disease and/or condition mediated by or indicated by the one or more target components. The one or more target components include, but are not limited to, cellular components (e.g., blood cells, cancer cells, pathogens), non-cellular components (e.g., proteins, lipids, sugars, carbohydrates, small molecules), or combinations thereof. Examples of diseases or conditions include, but are not limited to, acute and chronic inflammatory diseases (e.g., sepsis, multiple organ dysfunction syndrome, autoimmune disease, asthma, rhinitis, rheumatoid arthritis), cardiovascular disease, gastrointestinal disease, cancer, metabolic disease, bacterial infection (e.g., *Staphylococcus* bacteremia), viral infection (e.g., acquired immunodeficiency syndrome, hepatitis), parasite infection (e.g., malaria), chemical or biological agent exposure (e.g., drug overdose, environmental toxin).

An implantable device is provided which includes a body defining at least one lumen configured for fluid flow; at least one first reservoir in communication with the at least one lumen; one or more energy sources configured to provide energy to elicit one or more signal responses associated with one or more labels that bind to one or more target components in one or more of blood fluid or lymph fluid of the vertebrate subject; one or more sensors configured to detect the one or more signal responses associated with one or more labeled target components; and one or more reactive components in communication with the at least one lumen and for release responsive to the one or more sensors, wherein the one or more reactive components are configured to modulate a physiological effect of the one or more target components in the one or more of blood fluid or lymph fluid of the vertebrate subject. The one or more reactive components can be configured to alter, arrest, disrupt, destroy, inactivate, or ablate the one or more target components. In an aspect, the one or more reactive components can be within at least one second reservoir disposed within the at least one lumen. In an aspect, the one or more reactive components can include, but are not limited to, one or more reactive chemical components, one or more reactive biologic components, or one or more reactive physical components. The device can include at least one controllable flow barrier to the at least one lumen, and at least one controller in communication with the one or more sensors, and in communication with the at least one controllable flow barrier to the at least one lumen, wherein the controller is configured to control flow of the one or more of blood or lymph through the at least one lumen.

The device disclosed herein can include a body defining at least one lumen configured for fluid flow and configured to function in, or proximal to, one or more of a blood vessel or a lymph vessel of the vertebrate subject. The device can include one or more lumen configured to receive the one or more labeled target components. Alternatively, the device can include two or more parallel lumen configured to receive the one or more labeled target components. The phrase "two or more parallel lumen" includes two or more lumen that are parallel to each other or at least substantially parallel to each other. In an aspect, a diameter of each of the two or more parallel lumen is approximately less than two cell diameters. In an aspect, a diameter of each of the two or more parallel lumen is approximately less than 10 µm. The one or more lumens can include a plurality of parallel lumens, e.g., 10 or more lumens, 100 or more lumens, 1000 or more lumens, or 10,000 or more lumens, wherein each of the parallel lumens is less than two cell diameters in cross sectional width. In an aspect, the device can be a single unit. In an aspect, the device can include two or more separate units.

The device can include at least one first reservoir configured to include one or more labels that bind to one or more target components in one or more of blood fluid or lymph fluid of the vertebrate subject. The one or more labels can include one or more of a fluorescent label, electromagnetic-emitting label, magnetic label, electromagnetic label, paramagnetic label, quantum dot label, aptamer label, gold label, radioactive label, radiometrically-discernible label, or pro-drug, or a combination thereof. The electromagnetic-emitting label can include one or more labels emitting a specific EM energy frequency or a range of energy frequencies across the EM spectrum. The one or more labels can include a contrast agent label, a visible dye, a radiofrequency label, or a combination thereof. In an aspect, the one or more labels bind directly to the one or more target components from the blood or lymph of a vertebrate subject. In an aspect, the one or more labels include a binding component configured to bind selectively to one or more target components. The binding component of the label can include, but is not limited to, antibodies, antibody fragments, peptides, oligonucleotides, aptamers, protein nucleic acids, proteins, viruses, viral particles, enzymes, receptors, bacteria, cells, cell fragments, inorganic molecules, organic molecules, artificial binding substrates, e.g., formed by molecular imprinting, or combinations thereof.

The device can include one or more energy sources configured to provide energy to elicit one or more signal responses associated with the one or more labeled target components. The one or more energy sources include, but are not limited to, electromagnetic energy, acoustic energy, magnetic energy, electrical energy, or combinations thereof.

The device can include one or more sensors configured to detect one or more signal responses associated with the one or more labeled target components. The one or more sensors can include, but are not limited to, one or more of a biosensor, chemical sensor, physical sensor, or optical sensor. The sensor type depends on the nature and/or type of label bound to the one or more target compounds and the nature or type of signal response information required. Signal response can measure one or more properties of the one or more labeled target components. Signal response can include a photograph, size, concentration, granularity, chemical profile, magnetic property, electrical property, or a characteristic of the one or more labeled target components. In an aspect, the one or more signal responses can include one or more signal responses associated with an interior of the at least one lumen. In an aspect, the one or more signal responses can include one or more signal responses associated with the one or more blood vessel or lymph vessel of the vertebrate subject. The device can be configured to report to an outside source or to a computing device, wherein the device can be configured to report the detected one or more signal responses associated with the one or more labeled target components.

The device can include at least one second reservoir configured to include one or more reactive components responsive to the one or more sensors, wherein the one or more reactive components, e.g., one or more reactive chemical components, one or more reactive biologic components, or one or more reactive physical components, are configured to modulate a physiological effect of the one or more target components in the one or more of blood fluid or lymph fluid of the vertebrate subject. The at least one second reservoirs can be located within the at least one lumen. The one or more reactive components can be configured to alter, arrest, disrupt, destroy, inactivate, or ablate the one or more target components. For example, when the target component is one or more labeled target cells, the one or more reactive components can be configured to produce necrosis or apoptosis in the one or more labeled target cells. The one or more reactive components can be configured to bind to the at least one lumen. In an aspect, the one or more reactive components can include a bifunctional tag. The one or more reactive components can be configured to be released into the at least one lumen. The one or more reactive components can include, but are not limited to, one or more of a binding agent, a denaturing agent, a degradative agent, a cytotoxic agent, a cytostatic agent, an apoptotic agent, a chemotherapeutic agent, an antibody-toxin agent, or a combination thereof. The one or more binding agents on a matrix adapted to the at least one lumen can be configured to sequester at least one of the one or more labeled target components, e.g., one or more target cells, from the blood or lymph of the vertebrate subject. The one or more binding agents can include one or more of antibodies, receptors, or cognates configured to bind to at least one labeled target component. The at least one labeled target component can be sequestered by the binding agent prior to treatment with one or more of a second binding agent, a denaturing agent, a degradative agent, a cytotoxic agent, a cytostatic agent, an apoptotic agent, a chemotherapeutic, an antibody-toxin agent, or a combination thereof.

The device can include a controller in communication with the one or more sensors, and in communication with the at least one controllable flow barrier to the at least one lumen, wherein the controller is configured to control flow of the one or more of blood or lymph through the at least one lumen. The controller is in communication with the at least one first reservoir and the at least one second reservoir wherein the first reservoir including the one or more labels and the one or more reactive components are responsive to the controller. The controller is also in communication with one or more energy sources configured to provide energy to elicit a signal response, wherein the energy source is responsive to the controller. The controller is configured to control flow of the one or more blood or lymph based on the one or more signal responses associated with the one or more labeled target components. The controller is configured to control flow of the one or more of blood or lymph based on the label on the one or more target components. The controller is configured to control flow of the one or more of blood or lymph and to control the presence of the one or more reactive components delivered from the one or more second reservoirs, wherein controlling reactive components is based on the presence of the one or more labeled target components.

The device can include the controller and the one or more sensors which can be configured to attain a target level of the one or more target components in blood or lymph of the vertebrate subject. In an aspect, the one or more sensors and the controller can be configured to control levels of the one or more target components to substantially attain the target level of the one or more target components in the one or more of blood or lymph of the vertebrate subject. The target level of one or more target components can include a desired concentration of the one or more target components in the blood or lymph. The target level can include a desired range of concentrations of the one or more target components in the blood or lymph. The target level can include a desired ratio of concentrations of two or more target components in the blood or lymph. The one or more sensors and the controller can be configured to control levels of the one or more target components to limit a deviation from the target level. The deviation can be determined by a weighted least squares fit.

A method is disclosed herein for treating a disease or condition in a vertebrate subject. A method is disclosed herein for modulating a disease or condition in a vertebrate subject. The disease or condition can include, but is not limited to, an inflammatory disease or condition, an infectious disease or condition, or a neoplastic disease or condition. The method can include binding one or more target components with at least one label in one or more of blood fluid or lymph fluid of the vertebrate subject; providing energy to elicit one or more signal responses associated with one or more labeled target components; detecting the one or more signal responses associated with the one or more labeled target components; and providing one or more reactive components to modulate a physiological effect of the one or more target components in the one or more of blood fluid or lymph fluid of the vertebrate subject. The one or more reactive components can include one or more reactive components within at least one second reservoir disposed within the at least one lumen. The one or more reactive components include, but are not limited to, one or more reactive chemical components, one or more reactive biologic components, or one or more reactive physical components. The method can further include controlling flow of the one or more of blood fluid or lymph fluid through the at least one lumen with at least one controllable flow barrier. The method can further include controlling flow of the one or more of blood fluid or lymph fluid through the at least one lumen with at least one controller in communication with the one or more sensors and in communication with the at least one controllable flow barrier to the at least one lumen.

Methods are disclosed herein for treating or modulating diseases or conditions wherein the disease or condition can be alleviated, modulated, treated, prevented, reduced or eliminated by one or more reactive component configured to modulate a physiological effect of the one or more labeled target components in the blood or lymph of the vertebrate subject. The disease or condition can include, but are not limited to, cardiovascular diseases (e.g., ischemic heart disease, inflammatory heart disease), metabolic diseases (e.g., diabetes), gastrointestinal diseases (e.g., colitis, Crohn's disease), bacterial infections (e.g., *Staphylococcus* bacteremia, anthrax), viral infections (e.g., AIDS, hepatitis, hemorrhagic fever), parasitic infections (e.g., malaria, sleeping sickness, Chagas disease), metastatic cancer (e.g., lung, breast, skin, colon, kidney, prostate, pancreas, and cervix); blood cancers (e.g., leukemia, lymphoma, Hodgkin's disease, myeloma); chemical or biological agent exposure (e.g., drug overdose, poisoning, exposure to environmental toxin). Additional examples include a number of inflammatory diseases including, but not limited to, systemic inflammatory response syndrome, sepsis, septic shock, multiple organ dysfunction syndrome, ischemia reperfusion, hyperreactive airway disease, (e.g., asthma, chronic obstructive pulmonary disease, rhinitis, sinusitis), allergic reaction, anaphylaxis, autoimmune disease, infectious disease, pulmonary failure, allograft rejection, graft versus host disease (GVHD), chronic inflammatory disease, psoriatic arthritis, rheumatoid arthritis.

A system is disclosed herein which includes at least one computer program included on a computer-readable medium for use with at least one computer system wherein the computer program includes a plurality of instructions including, one or more instructions for determining at least one treatment of a vertebrate subject through an implantable device including one or more instructions for receiving data including data for delivering a body defining at least one lumen configured for fluid flow; one or more instructions for receiving data including data from at least one first reservoir in communication with the at least one lumen; one or more instructions for receiving data including data from one or more energy sources configured to provide energy to elicit one or more signal responses associated with one or more labels that bind to one or more target components in one or more of blood fluid or lymph fluid of the vertebrate subject; one or more instructions for receiving data including data from one or more sensors configured to detect the one or more signal responses associated with one or more labeled target components; and one or more instructions for receiving data including data from one or more reactive components in communication with the at least one lumen for release responsive to the one or more sensors, wherein the one or more reactive components are configured to modulate a physiological effect of the one or more target, components in the one or more of blood fluid or lymph fluid of the vertebrate subject.

A device is disclosed herein which includes a system including a signal-bearing medium including, one or more instructions for treatment of a vertebrate subject through an implantable device including one or more instructions for receiving data including data for delivering a body defining at least one lumen configured for fluid flow; one or more instructions for receiving data including data from at least one first reservoir in communication with the at least one lumen; and one or more instructions for receiving data including data from one or more energy sources configured to provide energy to elicit one or more signal responses associated with one or more labels that bind to one or more target components in one or more of blood fluid or lymph fluid of the vertebrate subject; one or more instructions for receiving data including data from one or more sensors configured to detect the one or more signal responses associated with one or more labeled target components; and one or more instructions for receiving data including data regarding one or more reactive components in communication with the at least one lumen for release responsive to the one or more sensors, wherein the one or more reactive components are configured to modulate a physiological effect of the one or more target components in the one or more of blood fluid or lymph fluid of the vertebrate subject.

Figure 2:
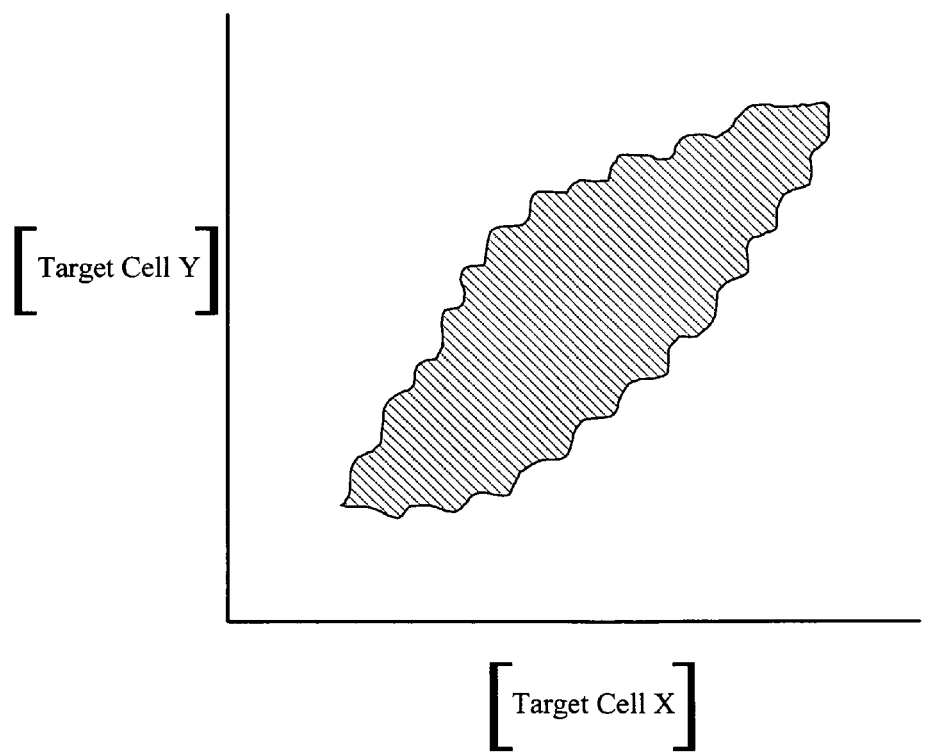
FIG. 2 depicts a diagrammatic view of an aspect of an embodiment of a device.
Figure 3:
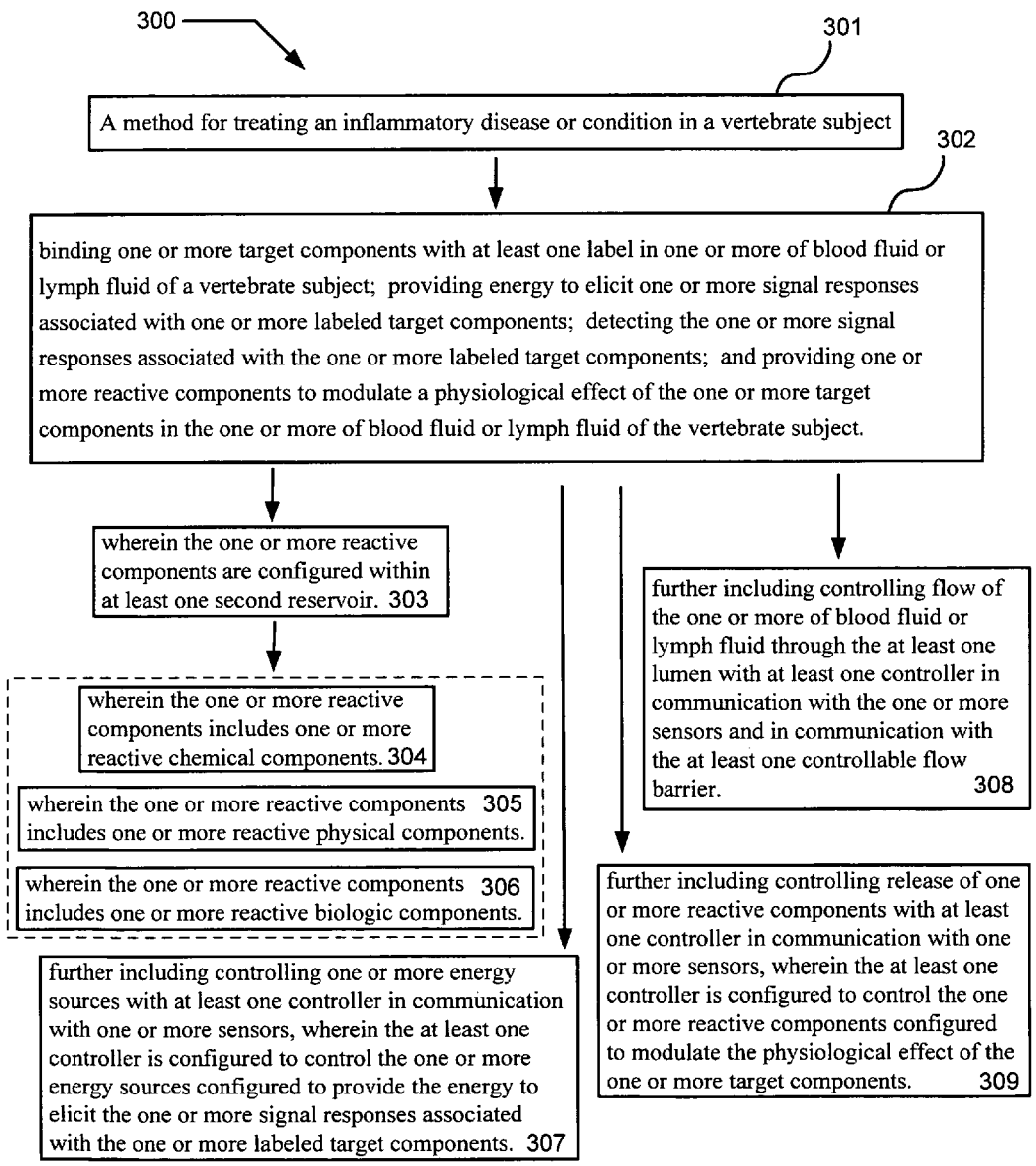
FIG. 3 depict a logic flowchart of a method for treating a disease or condition in a vertebrate subject.

With reference to the figures, and with reference now to FIGS. 1, 2, and 3, depicted is an aspect of a device, system, or method that can serve as an illustrative environment of and/or for subject matter technologies. The specific devices and methods described herein are intended as merely illustrative of their more general counterparts.

Referring to FIG. 1, depicted is a partial diagrammatic view of an illustrative embodiment of an implantable device 100 including a body defining at least one lumen 110 configured for fluid flow; at least one controllable flow barrier 120 to at least one lumen; at least one first reservoir 130 in communication with the at least one lumen and configured to include one or more labels 140 that bind to one or more target components 190 from one or more of blood fluid or lymph fluid 195 of a vertebrate subject; one or more energy sources 150 configured to provide energy to elicit one or more signal responses associated with one or more labeled target components 160; one or more sensors 170 configured to detect the one or more signal responses associated with the one or more labeled target components 160; and at least one second reservoir 180 configured to include one or more reactive chemical components 185 responsive to the labeled target components 160 following detection by the one or more sensors 170, wherein the one or more reactive chemical components 185 is configured to modulate a physiological effect of the one or more target components 160 in the one or more of blood fluid or lymph fluid 195 of the vertebrate subject. In an aspect, the one or more reactive chemical components 185 can be incorporated onto a surface of the second reservoir 180 or a surface of the lumen 110 of the device. In an aspect, the one or more reactive chemical components 185 can be released from the second reservoir 180 as one or more diffusible agents within the lumen or second reservoir or into the blood or lymph of the vertebrate subject.

Referring to FIG. 2, depicted is a partial diagrammatic view of an illustrative embodiment of calculations of a target value of one or more target components in an implantable device including a body defining at least one lumen configured for fluid flow; at least one first reservoir in communication with at least one lumen; one or more energy sources configured to provide energy to elicit one or more signal responses associated with one or more labels that bind to one or more target components in one or more of blood fluid or lymph fluid of a vertebrate subject; one or more sensors configured to detect the one or more signal responses associated with one or more labeled target components; and one or more reactive components in communication with at least one lumen for release responsive to the one or more sensors, wherein the one or more reactive components are configured to modulate a physiological effect of the one or more target components in the one or more of blood fluid or lymph fluid of the vertebrate subject. In an aspect, the target value can include a desired concentration of the one or more target components in the peripheral blood, or the target value can include a desired range of concentrations of the one or more target components in the peripheral blood. In an aspect, the target value can include a desired ratio of concentrations of two or more target components in the peripheral blood. In an aspect, the target value can be used to determine relative levels of the target components. The desired ratio of concentrations can be determined by any method or means, including for example, by a least squares fit of the concentrations of the two or more target components. For example, the desired ratio of concentrations can be determined by a least squares fit of the concentrations of the two or more target cells at concentrations $x_1, x_2, x_3$, and $x_4$ for a first inflammatory mediator, X, and at concentrations $y_1, y_2, y_3$, and $y_4$ for a second inflammatory mediator, Y. The least squares can fit to a line or to a two or three dimensional space indicating the preferred ratio of the two or more target cells.

Referring to FIG. 3, depicted is a logic flowchart of a method 300 for treating an inflammatory disease or inflammatory condition in a subject. The method 301 includes binding 302 one or more target components with at least one label in one or more of blood fluid or lymph fluid of a vertebrate subject; providing energy to elicit one or more signal responses associated with one or more labeled target components; detecting the one or more signal responses associated with the one or more labeled target components; and providing one or more reactive components to modulate a physiological effect of the one or more target components in the one or more of blood fluid or lymph fluid of the vertebrate subject. The method can include the one or more reactive components 303 configured within at least one second reservoir. The one or more reactive components can include one or more reactive chemical components 304, reactive biologic components 305, or reactive physical components 306. The method can further include controlling one or more energy sources 307 with at least one controller in communication with one or more sensors, wherein the at least one controller is configured to control the one or more energy sources configured to provide the energy to elicit the one or more signal responses associated with the one or more labeled target components. The method can further include controlling flow 308 of the one or more of blood fluid or lymph fluid through the at least one lumen with at least one controller in communication with the one or more sensors and in communication with the at least one controllable flow barrier. The method can further include controlling release 309 of one or more reactive components with at least one controller in communication with one or more sensors, wherein the at least one controller is configured to control release of the one or more reactive components configured to modulate the physiological effect of the one or more target components.

Device Functioning in or Proximal to Blood and/or Lymph Vessel

A device is disclosed herein for controlling or modulating the levels of one or more target components in the blood and/or lymph of a vertebrate subject and for treating a disease, condition or infection in the vertebrate subject. The device can include a body defining at least one lumen configured for fluid flow. The device can further include at least one controllable flow barrier to the at least one lumen, and at least one controller in communication with the one or more sensors, and in communication with the at least one controllable flow barrier to the at least one lumen, wherein the controller is configured to control flow of the one or more of blood or lymph through the at least one lumen.

The device for controlling or modulating a physiological effect of the one or more target components associated with a disease or condition is configured for use in, or proximal to, one or more blood vessels and/or lymph vessels of a vertebrate subject. In an aspect, the device can be an intra-vessel sized device, e.g., sufficiently small enough in size to be placed in a blood vessel and/or a lymph vessel while not necessarily obstructing flow through the vessel. The device can be inserted into a blood vessel or lymph vessel. The device can be within the vessel in whole or in part. Configurations for the device include, but are not limited to, a substantially tubular structure, with one or more lumens in fluid communication with the blood or lymph vessel of a vertebrate subject. In an aspect, the device can take the form of a short cylinder, an annulus, a cylinder, and/or a spiral. See, e.g., U.S. Patent Applications 2007/0066929 and 2008/0058785; Bezrouk et al, Scripta Medica (BRNO) 78(4):219-226, 2005, each of which is incorporated herein by reference. In an aspect, the device has a cylindrical and hollow configuration, with a single central opening, optionally allowing the exterior of the cylindrical structure to contact and engage the wall of the vessel, and the interior of the structure (within the single central opening) to form a fluid-contacting portion of the device. For example, the device can be configured as a specialized stent fixed within a specific artery or vein. See, e.g., U.S. Pat. Nos. 5,411,551; 7,326,240; 6,743,190; 6,793,642; 6,488,704; 7,244,232; U.S. Patent Applications 2007/0294150; 2008/0281400; 2006/01832223; 2008/0286278; Yokota, et al., 22nd IEEE International Conference Micro-Electro Mechanical Systems, Sorrento, Italy, January 25-29. IEEE pp. 495-499, 2009, each of which are incorporated herein by reference. For example, in a process for identifying and treating diseased cells, cells within a living organism can be labeled with a fluorescent marker in an implanted reservoir. Thereafter, the labeled cells are allowed to circulate within the organism and thereafter can be detected with the use of an implanted detector and either isolated or ablated. See, e.g., U.S. Patent Application 2007/0276208, each of which are incorporated herein by reference.

In an aspect, the device can include two or more parallel lumens configured to receive the one or more target components. The two or more parallel lumens can be parallel to each other. The two or more parallel lumens can be parallel to the blood vessel or lymph vessel of the subject. In an aspect, a diameter of each of the two or more parallel lumens is approximately less than ten cells diameters, less than eight cell diameter, less than six cell diameters, less than four cell diameters, less than two cell diameters. In an aspect, the diameter of each of the two or more parallel lumens can be the same diameter. In an aspect, the diameter of each of the two or more parallel lumens can vary from lumen to lumen. In an aspect, the diameter of each of the two or more parallel lumens can vary within a single lumen, e.g., tapering from wider to narrower. Tapering of the lumen diameter can function to slow the flow of the one or more target components through the lumen and increase contact with the one or more sensors and one or more reactive components. In an aspect, a diameter of each of the two or more parallel lumen is approximately less than 10 µm. The at least one lumens can include a plurality of parallel lumens, e.g., 10 or more lumens, 100 or more lumens, 1000 or more lumens, or 10,000 or more lumens, wherein each of the parallel lumens is approximately less than ten cells diameters, less than eight cell diameter, less than six cell diameters, less than four cell diameters, or less than two cell diameters in cross sectional width.

In an aspect, the device can be configured to be approximately hemi-spherical or hemi-elliptoid, in whole or in part, allowing a portion of a cross-section of at least a portion of the device to contact and/or engage the internal wall of a blood or lymph vessel without significantly and/or substantially obstructing the movement of fluid within the vessel. The device can include one or more wall engaging components including, but not limited to, rotating wheels, projections (e.g. arms), springs, hooks (e.g. claws), suction cups, and/or tissue adhesives that are configured to engage wall portions.

In an aspect, the device can be configured in a pill- or capsule-shape, and configured to move through a central portion of a vessel. The device can engage a wall of the vessel using one or more engaging components and/or freely travel through the blood and/or lymph systems. See, e.g., U.S. Patent Application 2007/0156211 A1, which is incorporated herein by reference. The device can be targeted to a site of disease, e.g., inflammation, infection, or cancer, in the vertebrate subject. In an aspect, the device can sense elevated levels of one or more target cells in the blood or lymphatic system of the vertebrate subject and can target and form a stationary location at, or near, a site of disease or condition in the circulation of the vertebrate subject. In an aspect, the implantable device can be incorporated into a shunt, e.g., an arteriovenous shunt inserted between an artery and a vein.

In an aspect, the device can be positioned, in whole or in part, proximal to a blood vessel or lymph vessel. "Proximal to" can refer to a space or area near to a blood vessel or lymph vessel. Locations that are proximal to a vessel can include, for example, locations external to the vessel wall where there is space for implanting one or more devices in whole or in part, and optionally to facilitate external access to the devices in whole or in part. In an aspect, "proximal to" can include distances including, but not limited to, approximately 0.1, 1.0, 10, and/or 100 µm and/or approximately 0.1, 1.0, 10, and/or 100 mm, and can optionally include larger and/or smaller distances depending on, for example, the availability of space and the size of the device and/or the vessel.

In an aspect, the device can be configured as a self-contained unit that includes all functionalities necessary for operation of the device. In another aspect, the system can be configured as two or more components in two or more locations separate from one another, wherein one or more of the components include one or more essential and/or non-essential functionalities. As an example, one component of the system can be placed within a blood vessel, and another component of the system placed proximal to the blood vessel optionally in a location more accessible from the exterior of the vertebrate subject, or where there is additional space. A remote portion can be configured to provide for monitoring of the vessel portion of the system, data collection, or data analysis, and/or remote-control of one or more other functions of the system such as sensing target cells, controlling flow through a flow route, and releasing a reactive component. The remote portion can be at a separate location within the body of the vertebrate subject, or outside the body of the vertebrate subject. Data and/or power signals can be transmitted between the one or more components of the device using electromagnetic signals, or electrical or optical links.

The dimensions and mechanical properties, e.g., rigidity, of the device, in whole or in part, can be configured for compatibility with the location of use in order to provide for reliable positioning and/or to provide for movement of the device while preventing damage to the vessel, the vessel lumen, and/or internal location and its surrounding structure. The choice of structural component size and configuration appropriate for a particular blood or lymph vessel location can be selected by a person of skill in the art. Structural components of the device can be constructed using a variety of manufacturing methods, from a variety of biocompatible materials. Appropriate materials include metals, ceramics, polymers, and composite materials having suitable biocompatibility, sterilizability, mechanical, and physical properties. Examples of materials and selection criteria are described, for example, in *The Biomedical Engineering Handbook* (Second Edition, Volume I, J. D. Bronzino, Ed., Copyright 2000, CRC Press LLC, pp. IV-1-43-22), which is incorporated herein by reference. Manufacturing techniques can include, but are not limited to, injection molding, extrusion, die-cutting, rapid-prototyping, and will depend on the choice of material and device size and configuration. Sensing and energy-emitting portions of the devices as well as associated control circuitry can be fabricated on the structural elements using various microfabrication and/or MEMS techniques or can be constructed separately and subsequently assembled to the structural elements, as one or more distinct components. See, e.g., U.S. Patent Applications 2005/0221529, 2005/0121411, 2005/0126916, 2007/0066939, 2007/0225633 and Nyitrai, et al. "Preparing Stents with Masking & Etching Technology"

26th International Spring Seminar on Electronics Technology pp. 321-324, IEEE, 2003, each of which is incorporated herein by reference.

In additional to biocompatible materials described and incorporated herein, flexible material having adjustable diameter, taper, and length properties can be used as part of the structural material. For example, some materials can change from a longer, narrower configuration, to a shorter, wider configuration, or can taper over their length, e.g., shape-memory polymers that can move from one shape to another in response to a stimulus such as heat. Structural elements that can exhibit this type of expansion/contraction property can include self-expanding material, resilient material, and/or mesh structures formed of various metals, e.g., ionic polymer-metal composites (IPMC) or plastics, and some polymeric materials, e.g., hydrogels, nitinol, or polyester. See, e.g. Bellin et al., *Proc. Natl. Acad. Sci. USA.* 103: 18043-18047, 2006; and Shanpoor et al., *Smart Mater. Struct.* 14:197-214, 2005, each of which is incorporated herein by reference.

Device for Controlling or Modulating Levels of One or More Target Components

Devices, systems, and methods are disclosed herein for controlling or modulating the levels of one or more target components in the blood and/or lymph of a vertebrate subject, and methods are disclosed for treating a disease, condition or infection in the vertebrate subject. The target component can be a normal component or an abnormal component of the blood or lymph of the vertebrate subject. The target component can be associated with a normal physiological state or with a pathological state of the vertebrate subject. The target component can be a non-cellular component or a cellular component of the blood or lymph of the vertebrate subject. Examples of non-cellular target components include, but are not limited to, proteins, lipids, sugars, minerals, vitamins or combinations thereof. Examples of cellular target components include one or more circulating cells, e.g., red blood cells, white blood cells, pathogens, pathogen-infected blood cells, cancer cells. In an aspect, the one or more target components can be one or more of a circulating emboli, a misfolded protein, an aggregated protein, an autoimmune antibody, an infectious agent, an infected cell, a thrombus, a plaque, a lipid, an aggregate, a cell, a specific cell type, a cell fragment, a cellular component, an intracellular component, an organelle, a collection or aggregation of cells, a cell membrane, a prion, a therapeutic agent, an illicit drug, a drug of abuse, or a toxin. See, e.g., He, et al., *Proc. Natl. Acad. Sci. USA* 104: 11760-11765, 2007, which is incorporated herein by reference. When the target component is an autoimmune antibody, the reactive component can include a component of cellular tissue bound by the autoimmune antibody configured to target the autoimmune antibody.

In an aspect, the one or more target components are cells circulating in the blood and/or lymph of a vertebrate subject. Cellular target components can include, but are not limited to, blood cells, e.g., platelets, red blood cells, neutrophils, lymphocytes, monocytes, eosinophils, basophils; or pathogens, e.g., viral-infected cells, bacteria, fungus, parasite; or cancer cells, e.g., metastatic cancer cells, blood cancer cells.

The one or more cellular target components can include, but are not limited to, one or more blood cells associated with a pathological state in which the normal circulating levels of one or more class of blood cells is elevated in the blood and/or the lymph of the vertebrate subject. For example, elevated levels of red blood cells can be associated with exposure to carbon monoxide, long-term lung disease, kidney disease, cancer, certain forms of heart disease, or liver disease. Elevated levels of platelets can be associated with bleeding, iron deficiency, cancer, or bone marrow pathologies. Elevated levels of neutrophils and eosinophils can be associated with infection, malignancy or autoimmune diseases. In an aspect, the cellular target components include blood cells that are modified or altered as a result of a disease and/or condition. For example, hyperactivated B-lymphocytes in patients with inflammatory bowel disease exhibit increased surface expression of toll-like receptor 2 (TLR2) relative to B-lymphocytes from normal individuals. See, e.g., Noronha, et al., *J. Leukoc. Biol.* 86: Epub ahead of print; Rea, WebMD. Complete Blood Count (CBC). at www.webmd.com/a-to-z-guides/complete-blood-count-cbc. Last updated Sep. 12, 2008; Accessed Oct. 5, 2009; each of which is incorporated herein by reference.

The one or more cellular target components can include one or more pathogens circulating in the blood and/or the lymph of the vertebrate subject. Examples of blood borne pathogens include, but are not limited to, pathogen-infected cells, e.g., human immunodeficiency virus (HIV), and the hepatitis B, hepatitis C, and hepatitis D viruses; bacteria, e.g., *Staphylococcus, Streptococcus, Pseudomonas, Haemophilus, Escherichia coli*; fungi, e.g., *Aspergillus, Candida albicans, Candida glabrata, Torulopsis glabrata, Candida tropicalis, Candida krusei*, and *Candida parapsilosis*; and parasites, e.g., *Trypanosoma cruzi, Trypanosoma brucei, Leishmania, Plasmodium, Babesia microti, Toxoplasma gondii*. Other bacterial pathogens that might be found in the blood and/or lymph at some point during a bacterial infection include, but are not limited to, *Bartonella, Coxiella burnetii, Chlamydia, Salmonella, Shigella, Yersinia, Legionella, Neisseria, Mycobacterium tuberculosis, Listeria, Corynebacterium diphtheriae, Campylobacter, Enterobacter*. Other viral-infected cells that can be found in the blood and/or lymph at some point during a viral infection include, but are not limited to, cytomegalovirus, influenza virus, human T-lymphotrophic virus, Epstein-Barr virus, roseolovirus, herpes lymphotropic virus, Karposi's sarcoma-associated herpes virus, herpes simplex virus, Ebola virus, or Marburg virus.

In another aspect, the one or more cellular target components can be one or more pathogens or pathogen-infected cells circulating in the blood and/or the lymph of a vertebrate subject. The one or more cellular target components can include one or more circulating blood cells infected with a pathogen including, but not limited to, bacteria, virus, or parasite. In an aspect, the one or more cellular target components include circulating blood cells infected with bacteria, e.g., red blood cells infected with *B. bacilliformis* or *Bartonella* spp. See, e.g., Dehio *Cell. Microbiol.* 10:1591-1598, 2008; Chomel et al., *Vet. Res.* 40: 29, 2009, each of which is incorporated herein by reference. In another aspect, the one or more cellular target components include one or more cells infected with HIV, primarily $CD4^+$ T lymphocytes but also including macrophages and dendritic cells. In an aspect, the one or more cellular target components include red blood cells infected with the malaria parasite *Plasmodium falciparum*. Red blood cells infected with *P. falciparum* can be distinguished from normal red blood cells by visual inspection, changes in granularities and changes in surface protein expression including expression on the red blood cell surface of the parasite derived protein *P. falciparum* erythrocyte membrane protein (PfEMP1). See, e.g., Dempster & Di Ruperto, *Circuits and Systems*, 2001. ISCAS 2001. The 2001 IEEE International Symposium, 5:291-294, 2001; Weatherall, et al., *Hematology Am. Soc. Hematol. Educ. Program* 35-57, 2002; Horata, et al., *Malaria J.* 8:184, 2009, each of which is incorporated herein by reference.

The one or more cellular target components can include one or more cancer cells circulating in the blood and/or lymph of a vertebrate subject. In an aspect, the cancer cells can include circulating tumor cells that have metastasized from solid tumors located elsewhere in the body. Examples of solid tumors from which metastatic cells can arise include, but are not limited to, carcinomas (e.g., adrenal, breast, cervical, colon, endometrial, lung, ovarian, pancreatic, prostate, stomach, testicular, thyroid, melanoma, head & neck) and sarcomas (e.g., brain, Ewing's sarcoma, Karposi's sarcoma, osteosarcoma, spinal cord). Circulating tumor cells are indicative of metastasis and can suggest a need for changes in the treatment regime. For example, the detection of circulating tumor cells in melanoma patients who are clinically "disease-free" indicates disease recurrence, tumor cell spreading, and a high potential for distant metastasis, and enables identification of high-risk melanoma patients. See, e.g., Schuster et al., *Clin. Cancer Res.* 13:1171-1178, 2007, which is incorporated herein by reference. The appearance of circulating tumor cells can also provide an indication of the long term prognosis for the patient. For example, breast cancer patients with levels of circulating tumor cells equal to or higher than five cells per 7.5 milliliters of blood have a shorter median progression-free survival (2.7 months vs. 7.0 months) and shorter overall survival (10.1 months versus greater than 18.0 months) as compared with breast cancer patients with less than five cells per 7.5 milliliters of blood. See, Cristofanilli et al. *N. Engl. J. Med.* 351:781-791, 2004, which is incorporated herein by reference.

In another aspect, the cancer cells can be associated with blood cancers. Examples of blood cancers include, but are not limited to, lymphoma, various types of leukemia, and multiple myeloma. Lymphoma is a cancer of lymphocytes which usually begins in a lymph node but can originate from the stomach, intestines, skin or any other organ. The two main types of lymphoma are Hodgkin's disease and non-Hodgkin's lymphoma. In Hodgkin's disease, the abnormal cells are called the Reed-Sternberg cells, giant binucleated or multinucleated macrophages. This type of cancer can spread throughout the lymphatic system, affecting any organ or lymph tissue in the body. Non-Hodgkin's lymphoma is classified by the size, type and distribution of cancer cells in the lymph nodes. Low-grade lymphomas include small-lymphocytic lymphoma, follicular small-cleaved-cell lymphoma, and follicular mixed-cell lymphoma. Intermediate-grade lymphomas include follicular large-cell lymphoma, diffuse small-cleaved-cell lymphoma, diffuse mixed lymphoma, and diffuse large-cell lymphoma. High-grade lymphomas include immunoblastic lymphoma, lymphoblastic lymphoma, and small noncleaved (Burkitt's and non-Burkitt's) lymphoma. Multiple myeloma is cancer of the bone marrow caused by the uncontrolled growth of effector B cells. Effector B cells normally make antibodies (e.g., immunoglobulins) to fight infections. In multiple myeloma effector B cells multiply uncontrollably, generating too much of a single type of immunoglobulin. The level of other immunoglobulins drops, leaving the patient vulnerable to infection. The cancerous plasma cells collect in the bones and bone marrow and can form tumors that destroy the bone tissue, causing the bones to become fragile and prone to fracture.

In an aspect, the one or more target components include non-cellular components present in the blood and/or lymph of a vertebrate subject. Non-cellular components can include, but are not limited to, sugars (e.g., glucose), lipids (e.g., triacylglycerols, cholesterol, phospholipids), vitamins, minerals, non-protein hormones (e.g., estrogen, testosterone), proteins (e.g., enzymes, hormones, antibodies, blood clotting factors, lipoproteins). Additional examples of proteins found in the blood and/or lymph include, but are not limited to, serum proteins (e.g., subclasses of immunoglobulins, complement factors, Cl esterase, circulating immune complexes, albumin, anti-trypsin, fetoprotein, acid glycoprotein, alpha-macroglobulin, beta-microglobulin, ceruloplasmin, transferrin), acute phase proteins associated with disease (e.g., C-reactive protein, SPLA2, ferritin), coagulation or complement related proteins (e.g., tissue-factor pathway inhibitor, soluble tissue factor, kallikrein, factor XIIa, thrombin, lupus anticoagulant, soluble CD46, soluble CD55), and markers of cellular activation (e.g., elastase, elastase/antitrypsin complexes, lactoferrin, granzym, nucleosomes, soluble CD16, soluble CD27).

The one or more target components can include one or more inflammatory mediators. Examples of inflammatory mediators include, but are not limited to, interferons (IFN) IFN-$\alpha$, IFN-$\beta$, and IFN-$\gamma$; interleukins (IL) IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-27, IL-28, IL-29, IL-30, IL-31, and IL-32; tumor necrosis factor (TNF) TNF-$\alpha$ and TNF-$\beta$; granulocyte colony stimulating factor (G-CSF); granulocyte-macrophage colony stimulating factor (GM-CSF); macrophage colony-stimulating factor (M-CSF); gelsolin, erythropoietin (EPO); and thrombopoietin (TPO). The one or more inflammatory mediators can be any of a number of chemotactic cytokines (chemokines) including, but not limited to, CC chemokines CCL1 through CCL28 exemplified by RANTES (CCL5), MCP-1 (CCL2), LARC (CCL20), MIP-1$\alpha$ (CCL3), and MDC (CCL22); CXC chemokines CXCL1 through CXCL17 exemplified by LIX (CXCL5), GCP-2 (CXCL6) and BCA-1 (CXCL13); C chemokines XCL1 and XCL2; CX3C chemokine C3CL1 (fractalkine); and chemokine like molecules exemplified by MIF. Other inflammatory mediators include, but are not limited to, anaphylatoxin fragments C3a, C4a, and C5a from the complement pathway; leukotrienes LTA4, LTB4, LTC4, LTD4, LTE4, and LTF4; prostaglandins; growth factors EGF, FGF-9, FGF-basic, growth hormone, stem cell factor (SCF), TGF-$\beta$ and VEGF; soluble receptors to tumor necrosis factor receptor (sTNFr); soluble interleukin receptors sIL-1r and sIL-2r; C-reactive protein; CD11b; histamine; serotonin; apolipoprotein A1; $\beta$2-microglobulin; bradykinin; D-dimer; endothelin-1; eotaxin; factor VII; fibrinogen; GST; haptoglobin; IgA; insulin; IP-10; leptin; LIF; lymphotactin; myoglobin; OSM; SGOT; TIMP-1; tissue factor; VCAM-1; VWF; thromboxane; platelet activating factor (PAF); immunoglobulins; and endotoxins such as lipopolysaccharide (LPS); and various exotoxins such as superantigens, e.g., from, *Staphylococcus aureus* and *Streptococcus pyogenes.*

In an aspect, the one or more target components are exogenous chemical or biological agents that have been introduced into the blood and/or lymph of a vertebrate subject. Examples of exogenous target components include, but are not limited to, drugs, both legal and illegal, poisons, and environmental toxins. Examples of drugs commonly used to treat disease include, but are not limited to, anti-depressants, anti-psychotics, anti-virals, anti-fungals, anti-parasitics, anti-protozoal drugs, anti-inflammatory, antibiotics, analgesics, anti-hypertensives, statins, other cardiovascular drugs, anti-seizure drugs, muscle relaxants, hormones, steroids, chemotherapeutic agents. Examples of common illicit drugs or drugs of abuse include, but are not limited to, cannabinoids such as hashish and marijuana; depressants such as barbiturates, benzodiazepines (e.g., Valium, Halcion), gamma hydroxy butyrate (GHB), and methaqualone; dissociative anesthetics such as ketamine and phencyclidine (PCP); hallucinogens such as LSD, mescaline, ibogaine, and psilocybin; opioids and morphine derivatives such as codeine, fentanyl, heroin, morphine, opium, oxycodone (OxyContin) and hydrocodone bitartate/acetaminophen (Vicodin); stimulants such as amphetamines, methamphetamine, cocaine, methylphenidate (Ritalin), MDMA (ecstasy), and nicotine; and anabolic steroids (see "Commonly Abused Drugs", National Institute on Drug Abuse, www.drugabuse.gov). Examples of environmental toxins include, but are not limited to, lead, arsenic, mercury, phthalates. Examples of additional environmental toxins can be found in *ATSDR: Safeguarding Communities from Chemical Exposures*, Centers for Disease Control, and in the Agency for Toxic Substances & Disease Registry as part of the Centers for Disease Control (www.atsdr.cdc.gov; Patel et al., *J. Med. Toxicol.* 2:83-84, 2006, each of which is incorporated herein by reference).

Device Including Labels for Labeling Target Components

The device disclosed herein includes one or more detectable labels that can target and bind to one or more target components in the blood or lymph of a vertebrate subject. The one or more detectable labels include, but are not limited to, at least one of a fluorescent label, an electromagnetic-emitting label, a quantum dot label, a gold label, dye, chemiluminescent dye, a prodrug, or a combination thereof. The one or more detectable labels can include at least one of a radioactive label; a radiopaque dye; a radiofrequency identification tag; fluorescent label; chromogenic label; a contrast agent label, a visible dye, volatile label; mass label; luminescent label, e.g., bioluminescent or chemiluminescent; metallic label, e.g., gold particles, magnetic beads, or paramagnetic beads; dyes, e.g., direct, indirect, or releasable; or a combination thereof.

The device including one or more labels configured to bind to one or more target components can be detected as a light-emitting label that either naturally emits light or emits light in response to an excitation energy. An example of a light-emitting label includes a variety of quantum dots or semiconductor nanocrystals that fluoresce at various wavelengths in response to an excitation energy (see, e.g., Jaiswal et al., *Nature Biotech*. 21:47-51, 2003, which is incorporated herein by reference). Examples of other fluorescing dyes for use with biological samples include, but are not limited to, fluorescein (FITC), indocyanine green (ICG) and rhodamine B, red and near infrared emitting fluorophores (600-1200 nm) including cyanine dyes such as Cy5, Cy5.5, and Cy7 (Amersham Biosciences, Piscataway, N.J., USA) and/or a variety of Alexa Fluor dyes such as Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA; see, e.g., U.S. Pat. App. No. 2005/0171434 A1, which is incorporated herein by reference). Additional fluorophores include IRDye800, IRDye700, and IRDye680 (LI-COR, Lincoln, Nebr., USA), NIR-1 and 105-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.), NIAD-4 (ICx Technologies, Arlington, Va.). Other fluorescing agents include BODIPY-FL, europium, green, yellow and red fluorescent proteins, luciferase. Alternatively, the light emitting marker can be a fluorescently labeled microsphere. Examples of fluorescently labeled microspheres ranging in diameter from 20 nanometers to 10 micrometers are available from commercial sources (e.g., Fluor Spheres® Fluorescent Microspheres, Invitrogen, Carlsbad, Calif.).

The device including one or more labels configured to bind to one or more target components can be one or more detectable labels including a radioactive marker. Radioactive labels can include one or more radioisotope commonly used in nuclear medicine, including, but are not limited to, iodine-131, cobalt-60, cesium-137, technetium-99m, carbon-11, nitrogen-13, oxygen-15, and fluorine-18. Other medical radioisotopes include, but are not limited to, americium-241, arsenic-74, gold-198, boron-11, carbon-14, calcium-48, cerium-141, cobalt-55, cobalt-57, chromium-51, cesium-130, cesium-131, copper-61, copper-62, copper-64, copper-67, dysprosium-165, europium-155, gallium-67, gallium-68, gadolinium-153, germanium-68, hydrogen-3, iodine-122, iodine-123, iodine-124, iodine-125, iodine-132, indium-111, indium-115m, Iridium-191m, krypton-81m, manganese-51, manganese-52, Nb-95, osmium-194, phosphorous-32, phosphorous-33, lead-203, lead-82, ruthenium-97, ruthenium-103, sulfur-35, scandium-46, selenium-72, selenium-75, strontium-85, tantalum-178, tantalum-182, terbium-149, thallium-201, xenon-127, xenon-133.

In an aspect, the device including one or more labels configured to bind to one or more target components can include a radioactive marker such as one used for diagnostic positron emission tomography (PET), single photon emission computed tomography (SPECT), and gamma camera imaging. Radioisotopes commonly used for PET, SPECT and gamma camera imaging include, but are not limited to, fluorine-18, carbon-11, nitrogen-13, oxygen-15, and fluorine-18; salts of radioisotopes such as I-131 sodium iodide, Tl-201 thallous chloride, Sr-89 strontium chloride; technetium Tc-99m; compounds containing iodine-123, iodine-124, iodine-125, and iodine-131; compounds containing indium-111 such as $^{111}$In-1,4,7,10-Tetraazacyclododecane-N,N',N'',N'''-tetraacetic acid and $^{111}$In-Diethylenetriamine pentaacetic acid; $^{177}$Lu-[(R)-2-amino-3-(4-isothiocyanatophenyl)propyl]-trans-(S,S)-cyclohexane-1,2-diamine-pentaacetic acid) ($^{177}$Lu-CHX-A"-DTPA), $^{64}$Cu-DOTA, $^{89}$Zr, $^{86}$Y-DOTA. For example, tritiated diisopropylfluorophosphate ($^{3}$H-DFP) can be used to selectively label granulocytes of neutrophils. See, e.g., Price et al. Blood 88:335-340, 1996, which is incorporated herein by reference.

In an aspect, the device including one or more labels configured to bind to one or more target components can include a magnetic marker, e.g., magnetic beads, magnetic particles or carbon nanotubes. Magnetic beads and magnetic particles of various sub-millimeter size are available from commercial sources (e.g., from Seradyn-Thermo Scientific, Indianapolis, Ind.; Dynal-Invitrogen, Carlsbad, Calif.). Carbon nanotubes with various functionalities can be synthesized de novo (see, e.g. Bianco et al. in *Nanomaterials for Medical Diagnosis and Therapy*. pp. 85-142. *Nanotechnologies for the Live Sciences* Vol. 10 Edited by Challa S. S. R. Kumar, WILEY-VCH Verlag GmbH & Co. KGaA, Weinheim, 2007, which is incorporated herein by reference) or may be available from commercial sources (e.g., from Nanolab, Newton, Mass.; Swan Chemical Inc., Lyndhurst, N.J.).

In an aspect, the device including one or more labels for labeling target components can include an ink or dye visible with ultraviolet, visible, near infrared, or infrared electromagnetic energy emitted by the device. Examples of vital dyes used to stain cells include, but are not limited to, acridin orange (stains DNA and RNA), DiOC (3,3'-dihexyloxacarbocyanine iodide; stains endoplasmic reticulum), rhodamine 123 (stains mitochondria), Nile red (stains lipid vesicles), DAPI (4',6-diamidino-2-phenylindole; stains DNA), Hoechst 33342 (stains DNA). Calcein AM and carboxyfluorescein diacetate are examples of membrane permeable dyes that are converted into membrane-impermeable dyes by cellular esterases, thereby trapping them inside live cells.

The device including one or more labels configured to bind to one or more target components can be one or more radiofrequency identification (RFID) tags, sub-millimeter versions of which have been described. See, e.g., Hornyak, *Scientific American Magazine*, pp 68-71, February 2008, which is incorporated herein by reference. Alternatively, the one or more label can include one or more bokodes, millimeter sized visual tags that can be captured with a camera. See, e.g., Mohan et al. *ACM Transactions on Graphics* Proceedings of SIGGRAPH 2009, Aug. 3-7, 2009, New Orleans, which is incorporated herein by reference.

The device including one or more labels configured to bind one or more target components can be one or more of a radiopaque dye or a contrast medium. Contrast agents, radiopaques, or roentgenographic drugs used for x-ray imaging and computed tomography (CT) include, but are not limited to, barium sulfate and various iodine derivatives including diatrizoate meglumine, diatrizoate sodium, iodipamide meglumine, diatrizoic acid, ethiodized oil, iodipamide, iodixanol, iohexyl, iomeprol, iopamidol, iopanoic acid, iophendylate, iopromide, iothalamate meglumine, iothalamate sodium, iothalamic acid, ioversol, ioxaglate meglumaine, or ioxaglate sodium.

The device including one or more labels configured to bind one or more target components can include one or more contrast agents used for magnetic resonance imaging (MRI) as exemplified by paramagnetic and supramagnetic agents with one or more unpaired electrons and typically including manganese, iron, or gadolinium in their structure. Examples of MRI contrast agents containing iron include, but are not limited to, ferumoxides (magnetite coated with dextran), ferumoxsil (magnetite coated with siloxane), ferumoxytol, ferumoxtran, ferucarbotran (RESOVIST), ferric chloride, ferric ammonium citrate. Examples of MRI contrast agents containing gadolinium include, but are not limited to, gadopentetate dimeglumine (Gd-DTPA; MAGNEVIST), gadobutrol (GADOVIST), gadodiamide (Gd-DTPA-BMA; OMNISCAN), gadoteridol (PROHANCE), Gd-DOTA (DOTAREM), gadofosveset trisodium (VASOVIST), gadoversetamide (OPTIMARK), gadobenate dimeglumine (MULTIHANCE). Examples of MRI contrast agents containing manganese include, but are not limited to, mangafodipir trisodium (TESLASCAN), EVP 1001-1.

Device Including Binding Components for Labels Configured to Bind Target Components A device is disclosed herein that can include sources of one or more labels configured to bind to one or more target components in the blood or lymph of a vertebrate subject. In an aspect, the one or more labels bind directly to the one or more target components, e.g., labels that intercalate directly and potentially non-selectively into cellular compartments such as plasma membrane, organelles, DNA and/or RNA. For example, cell membranes can be readily labeled with a number of fluorescent lipophilic dyes, examples of which include DiI (1,1'-dioctadecyl-3,3,3',3'-tetramethylindocarbocyanine perchlorate), DiO (3,3'-dioctadecyl-oxacarbocyanine perchlorate) and DiA 4-(4-(dihexadecylamino)styryl)-N-methylpyridinium iodide. In an aspect, the one or more labels can bind to a second component that is a binding component configured to selectively bind to one or more target components. Examples of binding components include, but are not limited to, antibodies, antibody fragments, peptides, oligonucleotides, aptamers, protein nucleic acids, proteins, viruses, enzymes, receptors, bacteria, cells, cell fragments, inorganic molecules, organic molecules, artificial binding substrates formed by molecular imprinting or combinations thereof.

The one or more binding components, e.g., one or more antibodies, can be configured to bind to the label and to the target component. Antibodies or antibody fragments for use as one or more binding components include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, chimeric antibodies, non-human antibodies, fully human antibodies, among others. Single chain or multiple chain antigen-recognition sites can be used. Multiple chain antigen-recognition sites can be fused or unfused. Antibodies or fragments' thereof can be generated using standard methods. See, e.g., Harlow & Lane, *Antibodies: A Laboratory Manual*, Cold Spring Harbor Laboratory Press; $1^{st}$ edition 1988, which is incorporated herein by reference. Alternatively, an antibody or fragment thereof directed against one or more target component can be generated, for example, using phage display technology. See, e.g., Kupper, et al. *BMC Biotechnology* 5:4, 2005, which is incorporated herein by reference. An antibody, a fragment thereof, or an artificial antibody, e.g., Affibody® artificial antibodies (Affibody AB, Bromma, Sweden) can be prepared using in silico design (Knappik et al., *J. Mol. Biol.* 296: 57-86, 2000, which is incorporated herein by reference. In an aspect, antibodies directed against one or more target components may be available from a commercial source (from, e.g., Novus Biological, Littleton, Colo.; Sigma-Aldrich, St. Louis, Mo.; United States Biological, Swampscott, Mass.).

The one or more binding components, e.g., one or more aptamers, can be configured to bind to the label and to the target component. The aptamer can be an oligonucleotide RNA- or DNA-based aptamer. Aptamers are artificial oligonucleotides (DNA or RNA) that can bind to a wide variety of entities (e.g., metal ions, small organic molecules, proteins, and cells) with high selectivity, specificity, and affinity. Aptamers can be isolated from a large library of $10^{14}$ to $10^{15}$ random oligonucleotide sequences using an iterative in vitro selection procedure often termed "systematic evolution of ligands by exponential enrichment" (SELEX). See, e.g., Cao, et al., *Current Proteomics* 2:31-40, 2005; Proske, et al., *Appl. Microbiol. Biotechnol.* 69:367-374, 2005; Jayasena *Clin. Chem.* 45:1628-1650, 1999, each of which is incorporated herein by reference. In general, SELEX can be used to generate aptamers against any of a number of target components including, but not limited to, inflammatory mediators, cancer cells, and bacteria. See, e.g., Guthrie, et al., *Methods* 38:324-330, 2006; Shangguan, et al., *Proc. Natl. Acad. Sci. USA.* 103:11838-11843; Chen, et al., *Biochem. Biophys. Res. Commun.* 357:743-748, 2007, each of which is incorporated herein by reference.

The one or more binding components, e.g., one or more peptide-based aptamers, can be configured to bind to the label and to the target component. Peptide aptamers are artificial proteins in which inserted peptides are expressed as part of the primary sequence of a structurally stable protein. See, e.g., Crawford, et al., *Brief. Funct. Genomic Proteomic* 2:72-79, 2003, which is incorporated herein by reference. Peptide aptamers can be generated by screening a target component against yeast two-hybrid libraries, yeast expression libraries, bacterial expression libraries and/or retroviral libraries. Peptide aptamers can have binding affinities comparable to antibodies.

The one or more binding components, e.g., one or more novel peptides, can be configured to bind to the label and to the target component. Novel peptides that bind selective targets can be generated, for example, using phage display methodologies. See, e.g., Spear, et al., *Cancer Gene Ther.* 8:506-511, 2001, which is incorporated herein by reference. In an aspect, the phage express novel peptides on the surface as fusion proteins in association with a phage major or minor coat protein and can be screened for binding interaction with one or more target components.

The one or more binding components, e.g., one or more receptors, can be configured to bind to the label and to the target component. All or part of a receptor can be used as a binding component, e.g., a soluble receptor. In an aspect, the target component can include a soluble ligand. In an aspect, the binding component, e.g., an antibody or aptamer, configured to bind to the label and to the target component can be configured to recognize one or more biomolecules on the surface of the one or more target cells. In an aspect, the binding component, e.g., an antibody or aptamer, configured to bind to the label can be configured to recognize one or more receptor types on the surface of target cells. In an aspect, the target component can include a soluble ligand. Examples of receptors include, but are not limited to, acetylcholine receptors, adenosine receptors, adrenoceptros, GABA receptors, angiotensin receptors, cannabinoid receptors, cholecystokinin receptors, dopamine receptors, glucagon receptors, glucocorticoid receptors, glutamate receptors, histamine receptors, mineralocorticoid receptors, olfactory receptors, opioid receptors, purinergic receptors, secretin receptors, serotonin receptors, somatostatin receptors, steroid hormone receptors, calcium-sensing receptor, hormone receptors, erythropoietin receptor, and natriuretic peptide receptors. Other examples include type I cytokine receptors such as type 1 interleukin receptors, erythropoietin receptor, GM-CSF receptor, G-CSF receptor, growth hormone receptor, oncostatin M receptor, leukemia inhibitory factor receptor; type II cytokine receptors such as type II interleukin receptors, interferon-α/β receptors, interferon-γ receptor; many members of the immunoglobulin superfamily such as interleukin-1 receptor, CSF1, c-kit receptor, interleukin-18 receptor; tumor necrosis factor (TNF) receptor family such as TNF receptor 1 (TNF-R1), TNF receptor 2 (TNF-R2), CD27, CD40, and lymphotoxin β receptor; chemokine receptors including serpentine CCR and CXCR receptors, such as CCR1 and CXCR4, and interleukin-8 receptor; TGF β receptors such as TGF β receptor 1 and TGF β receptor 2. See Ozaki and Leonard, *J. Biol. Chem.* 277:29355-29358, 2002, which is incorporated herein by reference In some instances, the one or more binding components configured to bind to the label and to the target component can include one or more cellular receptors that recognize and/or bind to bacteria. For example, the cellular receptor, CD14 which is normally associated with monocyte/macrophages, is known to bind lipopolysaccharide associated with gram negative bacteria as well as lipoteichoic acid associated with the gram positive bacteria *Bacillus subtilis* (see, e.g., Fan, et al. (1999) *Infect. Immun.* 67: 2964-2968). Other examples of cellular receptors include, but are not limited to, adenylate cyclase (*Bordatella pertussis*), Gal alpha 1-4Gal-containing isoreceptors (*E. coli*), glycoconjugate receptors (enteric bacteria), Lewis(b) blood group antigen receptor (*Heliobacter pylori*), CR3 receptor, protein kinase receptor, galactose N-acetylgalactosamine-inhibitable lectin receptor, and chemokine receptor (Legionella), annexin I (*Leishmania mexicana*), ActA protein (*Listeria monocytogenes*), meningococcal virulence associated Opa receptors (Meningococcus), alpha5beta3 integrin (*Mycobacterium avium*-M), heparin sulphate proteoglycan receptor, CD66 receptor, integrin receptor, membrane cofactor protein, CD46, GM1, GM2, GM3, and CD3 (*Neisseria gonorrhoeae*), KDEL receptor (*Pseudomonas*), epidermal growth factor receptor (*Samonella typhiurium*), alpha5beta1 integrin (Shigella), and nonglycosylated J774 receptor (Streptococci) (see, e.g., U.S. Patent Application 2004/0033584 A1, which is incorporated herein by reference).

The one or more binding components, e.g., one or more lectins, can be configured to bind to the label and to the target component. "Lectin" has been used to define agglutinins which could discriminate among types of red blood cells and cause agglutination. "Lectin" can be used more generally and includes sugar-binding proteins from many sources regardless of their ability to agglutinate cells. Lectins have been found in plants, viruses, microorganisms and animals. Because of the specificity that each lectin has toward a particular carbohydrate structure, even oligosaccharides with identical sugar compositions can be distinguished or separated. Some lectins will bind only to structures with mannose or glucose residues, while others can recognize only galactose residues. Some lectins require that the particular sugar is in a terminal non-reducing position in the oligosaccharide, while others can bind to sugars within the oligosaccharide chain. Some lectins do not discriminate between a and b anomers, while others require not only the correct anomeric structure but a specific sequence of sugars for binding. Examples of lectins include, but are not limited to, algal lectins, e.g., b-prism lectin; animal lectins, e.g., tachylectin-2, C-type lectins, C-type lectin-like, calnexin-calreticulin, capsid protein, chitin-binding protein, ficolins, fucolectin, H-type lectins, I-type lectins, sialoadhesin, siglec-5, siglec-7, micronemal protein, P-type lectins, pentrxin, b-trefoil, galectins, congerins, selenocosmia huwena lectin-I, Hcgp-39, Ym1; bacterial lectins, e.g., *Pseudomonas* PA-IL, *Burkholderia lectins*, chromobacterium CV-IIL, *Pseudomonas* PA IIL, *Ralsonia* RS-ILL, ADP-ribosylating toxin, *Ralstonia* lectin, *Clostridium* hemagglutinin, *botulinum* toxin, tetanus toxin, cyanobacterial lectins, FimH, GafD, PapG, Staphylococcal enterotoxin B, toxin SSL11, toxin SSL5; fungal and yeast lectins, e.g., *Aleuria aurantia* lectin, integrin-like lectin, *Agaricus* lectin, *Sclerotium* lectin, *Xerocomus* lectin, *Laetiporus* lectin, *Marasmius oreades* agglutinin, agrocybe galectin, *coprinus* galectin-2, Ig-like lectins, L-type lectins; plant lectins, e.g., alpha-D-mannose-specific plant lectins, *amaranthus* antimicrobial peptide, hevein, pokeweed lectin, *Urtica dioica* UD, wheat germ WGA-1, WGA-2, WGA-3, artocarpin, artocarpus hirsute AHL, banana lectin, Calsepa, heltuba, jacalin, Maclura pomifera MPA, MornigaM, Parkia lectins, abrin-a, abrus agglutinin, amaranthin, castor bean ricin B, ebulin, mistletoe lectin, TKL-1, cyanovirin-N homolog, and various legume lectins; and viral lectins, e.g., capsid protein, coat protein, fiber knob, hemagglutinin, and tailspike protein. See, e.g., E. Bettler, R. Loris, A. Imberty "3D-Lectin database: A web site for images and structural information on lectins" 3rd Electronic Glycoscience Conference, The interne and World Wide Web, 6-17 Oct. 1997; http://www.cermav.cnrs.fr/lectines/, which is incorporated herein by reference.

The one or more binding components configured to bind to the label can include one or more artificial binding substrates formed by the process of molecular imprinting. In the process of molecular imprinting, a template, e.g., target component, is combined with functional monomers which upon cross-linking form a polymer matrix that surrounds the template. See, e.g., Alexander, et al., *J. Mol. Recognit.* 19:106-180, 2006, which is incorporated herein by reference. Removal of the template leaves a stable cavity in the polymer matrix that is complementary in size and shape to the template. In an aspect, functional monomers of acrylamide and ethylene glycol dimethacrylate can be mixed with one or more target components in the presence of a photoinitiator and ultraviolet irradiation used to cross-link the monomers. The resulting polymer can be crushed or ground into smaller pieces and washed to remove the one or more target components, leaving a particulate matrix material capable of binding one or more target components. Examples of other functional monomers, cross-linkers and initiators can be used to generate an artificial binding substrate are provided. See, e.g., U.S. Pat. No. 7,319,038; Alexander, et al., *J. Mol. Recognit.* 19:106-180, 2006, each of which is incorporated herein by reference. In an aspect, hydrogels can be used for molecular imprinting. See, e.g., Byrne et al., "Molecular imprinting within hydrogels", *Advanced Drug Delivery Reviews,* 54: 149-161, 2002, which is incorporated herein by reference. Other examples of synthetic binders are provided. See, e.g., U.S. Pat. Nos. 6,255,461; 5,804,563; 6,797,522; 6,670,427; and 5,831,012; and U.S. Patent Application 20040018508; and Ye and Haupt, *Anal Bioanal Chem.* 378: 1887-1897, 2004; Peppas and Huang, *Pharm Res.* 19: 578-587 2002, each of which is incorporated herein by reference.

In an aspect, the binding component configured to bind to the label and to the target component can be configured to recognize other biomolecules on the surface of target cells including, but not limited to, various CD (cluster of designation/cluster of differentiation) markers, intergrins, ion channels, ATPases, cell adhesion molecules, integral membrane glycoproteins, immunoglobulins, transporters. The one or more binding components can be configured to recognize components of cell surface biomolecules including amino acid sequence and oligosaccharide modifications.

In an aspect, the binding component configured to bind to the label and to the target component can be configured to recognize a biomolecule associated with a tumor cell. Examples of tumor associated components can include, but are not limited to, BLyS receptor, carcinoembryonic antigen (CA-125), CD25, CD34, CD33 and CD123 (acute myeloid leukemia), CD20 (chronic lymphocytic leukemia), CD19 and CD22 (acute lymphoblastic leukemia), CD30, CD40, CD70, CD133, 57 kD cytokeratin, epithelial specific antigen, epithelial cell adhesion molecule (EpCAM), extracellular matrix glycoprotein tenascin, Fas/CD95, folate receptor, gastrin-releasing peptide-like receptors, hepatocyte specific antigen, human gastric mucin, human milk fat globule, lymphatic endothelial cell marker, matrix metalloproteinase 9, melan A, melanoma marker, mesothelin, mucin glycoproteins (e.g., MUC1, MUC2, MUC4, MUC5AC, MUC6), prostate specific antigen, prostatic acid phosphatase, PTEN, renal cell carcinoma marker, RGD-peptide binding integrins, sialyl Lewis A, six-transmembrane epithelial antigen of the prostate (STEAP), TNF receptor, TRAIL receptor, tyrosinase, villin. Other tumor associated antigens include, but are not limited to, alpha fetoprotein, apolipoprotein D, clusterin, chromogranin A, myeloperoxidase, MyoD1 myoglobin placental alkaline phosphatase c-fos, homeobox genes.

In an aspect, the binding component configured to bind to the label and to the target component can be configured to recognize a biomolecule associated with the surface of a pathogen, e.g., bacteria, a virus, a fungus, or a parasite. The biomolecule can be one or more components of the bacterial outer membrane, cell wall, and/or cytoplasmic membrane. Examples of components associated with the bacterial outer membrane of Gram-negative bacteria include, but are not limited to, lipopolysaccharide and OMP (outer membrane protein) porins, the latter of which are exemplified by OmpC, OmpF and PhoP of *E. coli*. Examples of components associated with the bacterial cell wall of both Gram-positive and Gram-negative bacterial include, but are not limited to, peptidoglycans polymers composed of an alternating sequence of N-acetylglucoamine and N-acetyl-muraminic acid and crosslinked by amino acids and amino acid derivatives. Examples of components associated with the bacterial cytoplasmic membrane include, but are not limited to, the MPA1-C (also called polysaccharide copolymerase, PCP2a) family of proteins, the MPA2 family of proteins, and the ABC bacteriocin exporter accessory protein (BEA) family of proteins. Other examples of components associated with bacteria include, but are not limited to, transporters, e.g., sugar porter (major facilitator superfamily), amino-acid/polyamine/organocation (APC) superfamily, cation diffusion facilitator, resistance-nodulation-division type transporter, SecDF, calcium:cation antiporter, inorganic phosphate transporter, monovalent cation:proton antiporter-1, monovalent cation:proton antiporter-2, potassium transporter, nucleobase:cation symporter-2, formate-nitrite transporter, divalent anion:sodium symporter, ammonium transporter, and multi-antimicrobial extrusion; channels, e.g., major intrinsic protein, chloride channel, and metal ion transporter; and primary active transporters, e.g., P-type ATPase, arsenite-antimonite efflux, Type II secretory pathway (SecY), and sodium-transporting carboxylic acid decarboxylase. A number of other potential components associated with bacteria have been described in Chung, et al., *J. Bacteriology* 183:1012-1021, 2001, which is incorporated herein by reference.

In an aspect, the binding component configured to bind to the label and to the target component can be configured to recognize a biomolecule associated with a blood cell infected with a pathogen. For example, red blood cells infected with *P. falciparum* can be distinguished from normal red blood cells by changes in surface protein expression including expression on the red blood cell surface of the parasite derived protein *P. falciparum* erythrocyte membrane protein (PfEMP1). See, e.g., Horata, et al., *Malaria J.* 8:184, 2009, which is incorporated herein by reference.

Device Including Labels Linked to Binding Components to Elicit a Signal Response The device can include at least one first reservoir that includes one or more labels that bind one or more target components from the blood or lymph of the vertebrate subject to elicit a signal response from the labeled binding component. The one or more labels can include a binding component configured to bind selectively to one or more target components. The one or more labels that bind to one or more target components can be linked to one or more binding components using a variety of methods including, but not limited to, one or more of a chemical cross-link, a streptavidin/biotin interaction (Thermo Fisher Scientific, Rockford, Ill.), his-tagged protein on nickel-NTA resin affinity column (Thermo Fisher Scientific, Rockford, Ill.), a fusion protein construct, a common substrate, or a combination thereof. In an aspect, the label and the binding component are directly associated with one another through chemical cross-linking, non-covalent linking, or synthesis as a single molecule. In another aspect, the label and the binding component are indirectly associated. In this instance, the label and the binding component are separately attached to a mobile substrate such as, for example, a bead or other particle-like substrate capable of being released into the blood or lymph of the vertebrate subject. The particle-like substrate can include a bead, a vesicle, a cell, a carbon nanotube, or other similar structure.

In an aspect, the label can be conjugated to the binding component using one or more of a cross linking agent. In general, any of a number of cross linking agents can be used to conjugate an appropriately derivatized label to an appropriately derivatized or functionalized binding component. For example, a fluorescent dye, e.g., rhodamine, derivatized with succinimidyl ester (from, e.g., Invitrogen, Carlsbad, Calif.) will react efficiently with primary amines of proteins, e.g., antibodies, to generate a stable fluorescent dye-protein conjugate. See, e.g., Hama et al., *Cancer Res.* 67:2791-2799, 2007, which is incorporated herein by reference. As another example, an antibody for use in a label configured to bind to a target component can be conjugated with one or more quantum dots via an amine-thiol linkage using amine-derivatized, poly-ethylene glycol coated quantum dots and the amine-thiol crosslinker SMCC using a commercially available kit (Qdot® Antibody Conjugation Kit, Invitrogen, Carlsbad, Calif.). Similarly, various methods are available for attaching quantum dots to a DNA backbone of an aptamer such as, for example, covalent linkage of amine-modified DNA to carboxylated quantum dots. For example, carboxy quantum dots (from, e.g., Quantum Dot Corporation, Hayward, Calif., USA) can be attached to an aptamer through a C6 amino modifier placed on either the 5 prime or 3 prime end of the aptamer sequence. Magnetic beads derivatized with carboxylic acid, amine groups or tosylactivated for cross-linking to proteins and appropriately derivatized oligonucleotides are also commercially available (from, e.g., Dynal Biotech, Brown Deer, Wis.). Quantum dots, fluorescent dyes, and magnetic particles derivatized for cross-linking to antibodies, aptamers or other biomolecules are available from a number of commercial sources (from, e.g., Invitrogen, Carlsbad, Calif.; Seradyn-Thermo Scientific, Indianapolis, Ind.; Sigma-Aldrich, St. Louis, Mo.).

In an aspect, the derivatized fluorescent dye itself can be used to label target cells. For example, cells can be stably labeled with 5,6-carboxyfluorescein diacetate succinimidyl ester, a derivatized fluorescent dye capable of entering a cell and once inside a cell, binding to primary amines associated with cytoplasmic proteins. See, e.g., Humphreys et al, *Toxicol. Sci.* 73:80-89, 2003, which is incorporated herein by reference.

Examples of cross linking agents for cross linking one or more of a label with one or more of a binding component include, but are not limited to, primary amine/primary amine linkers such as DMS (dimethyl suberimidate), DMP (dimethyl pimelimidate), DSS (disuccinimidyl suberate), DST (disuccinimidyl tartate), Sulfo DST (sulfodisuccinimidyl tartate), DSP (dithiobis(succinimidyl propionate) and sulfhydryl/sulfhydryl linkers such as DPDPB (1,4-di-(3'-[2'pyridyldithio]-propionamido) butane); primary amine/sulfhydryl linkers such as MBS (m-maleimidobenzoyl-N-hydroxysuccinimide ester), Sulfo MBS (m-maleimidobenzoyl-N-hydroxysulfosuccinimide), Sulfo GMBS (N-γ-maleimidobutyryloxysulfosuccinimide ester), EMCS (N-(epsilon-maleimidocaproyloxy)succinimide ester), Sulfo EMCS (N-(epsilon-maleimidocaproyloxy)sulfo succinimide), SMCC (succinimidyl 4-(N-maleimidomethyl) cyclohexane-1-carboxylate), SMPB (succinimidyl 4-(rhomaleimidophenyl)butyrate), Sulfo SIAB (N-sulfosuccinimidyl(4-iodoacetyl)aminobenzoate), cyclohexane-1-carboxylate), and MAL-PEG-NHS (maleimide PEG N-hydroxysuccinimide ester); sulfhydryl/hydroxyl linkers such as PMPI (N-rho-maleimidophenyl)isocyanate; sulfhydryl/carbohydrate linkers such as EMCH (N-(epsilon-maleimidocaproic acid)hydrazide); and amine/carboxyl linkers such as EDC (1-ethyl-3-(3-dimethylaminopropyl)carbodiimide hydrochloride).

In an aspect, the label can be conjugated to the binding component using one or more interactions between biotin and avidin, streptavidin or derivatives thereof. Streptavidin and avidin are multivalent proteins capable of binding multiple biotin subunits with high affinity and as such can be used as linking molecules between one or more biotinylated label and one or more biotinylated binding component. For example, a biotinylated fluorescent label, e.g., biotin-4-fluorescein (from, e.g., Invitrogen, Carlsbad, Calif.) can be linked to a biotinylated antibody through a streptavidin bridge. An antibody or other protein-based binding component can be biotinylated using an amine reactive biotinylation reagent such as, for example, EZ-Link Sulfo-NHS-SS-Biotin (sulfosuccinimidyl 2-(biotinamido)-ethyl-1,3-dithiopropionate; Pierce-Thermo Scientific, Rockford, Ill., USA; see, e.g., Jaiswal, et al. *Nature Biotech.* 21:47-51, 2003, which is incorporated herein by reference). Similarly, a biotinylated label can be linked to a biotinylated oligonucleotide aptamer through a streptavidin bridge. An aptamer or other nucleotide-based binding component can be biotinylated by introducing a biotinylated nucleotide, e.g., biotin-5-deoxycytidine-5-triphosphate (from, e.g., ChemCyte, Inc., San Diego, Calif.) into the aptamer sequence during in vitro transcription. The biotinylated label is reacted with the biotinylated binding component in the presence of streptavidin to generate a label for binding to a target component. Radioactive labels, e.g., iodine-125, can also be biotinylated. See, e.g., Garlick & Giese. *J. Biol. Chem.* 263:210-215, 1988, which is incorporated herein by reference.

Alternatively, the label or the binding component can be modified with streptavidin, avidin, or derivative thereof and directly bound to a biotinylated label or binding component. In an aspect, the label is modified with streptavidin and combined with a biotinylated binding component. For example, streptavidin modified quantum dots (available from, e.g., Quantum Dot Corporation, Hayward, Calif., USA) can be attached to an aptamer through a biotin modification to the 5-prime end of the aptamer sequence. See, e.g., Cady et al. *Mol. Cell. Probes* 21:116-124, 2007, which is incorporated herein by reference. Examples of other streptavidin modified fluorescent dyes are available (from, e.g., PerkinElmer, Waltham, Mass.; Alpha Diagnostic Intl. Inc., San Antonio, Tex.). Streptavidin modified magnetic beads are also commercially available (e.g., Dynabeads® MyOne™ Streptavidin, Dynal Biotech, Brown Deer, Wis.). In another aspect, the binding component can contain all or part of the streptavidin protein for use in binding to a biotin modified label. For example, cDNA sequence encoding all or part of an antibody or other protein/peptide can be genetically modified to contain all or part of the streptavidin gene using standard cloning procedures, resulting in a streptavidin-antibody fusion protein. See, e.g., Koo, et al. *Appl. Environ. Microbiol.* 64:2497-2502, 1998, which is incorporated herein by reference. The streptavidin modified binding component can subsequently be combined with one or more of a biotinylated label to generate label configured to bind one or more target components.

In an aspect, the label, e.g., radioactive label or fluorescent label, can be incorporated into the label at the time of synthesis. For example, radiolabeled nucleotides or radiolabeled amino acids can be incorporated respectively into an oligonucleotide aptamer or protein antibody or other protein-based binding component during synthesis using standard methods. Alternatively, the label can be a fusion protein with a binding component, e.g., antibody, peptide ligand, or receptor, designed to bind to or associate with a target component and a label component including all or part of green fluorescent protein (GFP) derived from *Aequorea victoria* jellyfish or yellow, red and blue fluorescing derivatives thereof. A number of expression constructs for generating recombinant GFP fusion proteins are available from commercial sources (from, e.g., Invitrogen, Carlsbad, Calif.).

In another aspect, the label configured to bind to one or more target components can be a DNA construct encoding a fluorescent protein and inserted into one or more target cells in the blood or lymph of a vertebrate subject. For example, baculovirus expression constructs are available which when introduced into a cell induce expression of specific fluorescent proteins, e.g., Cellular Lights™ fluorescent proteins and Organelle Lights™ fluorescent proteins (from Invitrogen, Carlsbad, Calif.).

Methods have also been described for incorporating the label configured to bind to one or more target components wherein gold nanoparticles can be linked to aptamers for use in reflectance imaging applications, in which the aptamer is derivatized with a 5-prime thiol group and interacted with colloidal gold nanoparticles (from, e.g., Ted Pella, Inc., Redding, Calif.). See, e.g., Javier et al. *Bioconjugate Chem.* 19:1309-1312, 2008, which is incorporated herein by reference.

In an aspect, the detectable label including a binding component may be available from a commercial source. For example, lectins concanavalin A and wheat germ agglutinin are available conjugated to Alexa fluors, Marina Blue, AMCA, Oregon Green, tetramethylrhodamine, Texas Red, fluorescein (from, Invitrogen, Carlsbad, Calif.). Other lectins conjugated to fluorescent dyes are available including *Phaseolus vulgaris* lectin (PHA-L), *Arachis hypogaea* lectin (PNA), *Helix pomatia* agglutinin (HPA), Soybean agglutinin (SBA), and lectins from *Griffonia simplicifolia* (from, Invitrogen, Carlsbad, Calif.). Magnetic beads with an antibody to the human epithelial antigen, EpCAM (epithelial cell adhesion molecule) are commercially available (from, e.g., Dynal Biotech, Brown Deer, Wis.). EpCAM can be used to selectively bind circulating tumor cells of epithelial origin in the blood or lymph of a vertebrate subject. Anti-CA-125 (anti-carcinoembryonic antigen) antibodies can be used to selectively bind circulating tumor cells of ovarian cancer origin in the blood or lymph of a mammalian subject. Anti-CA125 antibodies can be conjugated to rhodamine-X (Invitrogen, Eugene, Oreg.). Anti-FR (anti-folate receptor) antibodies and folate-FITC, folate-Tc99m can be used to selectively bind circulating tumor cells that overexpress folate receptors, e.g., ovarian cancer cells, and circulating tumor cells in the blood or lymph of a mammalian subject. Endocyte, Inc., West Lafayette, Ind. See, e.g., He, et al., *Proc. Natl. Acad. Sci. USA* 104: 11760-11765, 2007, which is incorporated herein by reference.

Device Including Activatable Labels for Labeling Target Components

The device can include at least one first reservoir that includes one or more labels that bind one or more target components from the blood or lymph of the vertebrate subject. The device can include one or more energy sources configured to provide energy to elicit one or more signal responses associated with one or more labeled target components. The one or more labels that bind to one or more target components can be one or more activatable labels configured to controllably emit a measurable signal in response to binding a target component. In an aspect, the one or more activatable labels can emit a measurable signal only when a target component is bound. Alternatively, the one or more activatable labels can emit a first measurable signal in the absence of a bound target component and a second measurable signal in the presence of a bound target component.

In an aspect, the activatable label can be configured such that binding of the target component to the binding component of the label results in a conformational change in the label that can be measured using fluorescence resonance energy transfer (FRET). FRET is a distance-dependent interaction between the electronic excited states of two dye molecules in which excitation is transferred from a donor molecule to an acceptor molecule without emission of a photon. In an aspect, interaction of a donor molecule with an acceptor molecule can lead to a shift in the emission wavelength associated with excitation of the acceptor molecule. In an aspect, interaction of a donor molecule with an acceptor molecule can lead to quenching of the donor emission. The binding component of the activatable label configured to bind one or more target components can include at least one donor molecule and at least one acceptor molecule. In this configuration, binding of one or more target components to the binding component of the activatable label results in a conformational change in the binding component and results in a change in the distance between the donor and acceptor molecules and a change in measurable label, e.g., fluorescence.

A variety of donor and acceptor fluorophore pairs can be considered for FRET including, but not limited to, fluorescein and tetramethylrhodamine; IAEDANS and fluorescein; fluorescein and fluorescein; and BODIPY FL and BODIPY FL. A number of Alexa Fluor (AF) fluorophores (Molecular Probes-Invitrogen, Carlsbad, Calif., USA) can be paired with other AF fluorophores for use in FRET. Some examples include, but are not limited, to AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

The cyanine dyes Cy3, Cy5, Cy5.5 and Cy7, which emit in the red and far red wavelength range (>550 nm), offer a number of advantages for FRET-based detection systems. Their emission range is such that background fluorescence is often reduced and relatively large distances (>100 Å) can be measured as a result of the high extinction coefficients and good quantum yields. For example, Cy3, which emits maximally at 570 nm and Cy5, which emits at 670 nm, can be used as a donor-acceptor pair. When the Cy3 and Cy5 are not proximal to one another, excitation at 540 nm results only in the emission of light by Cy3 at 590 nm. In contrast, when Cy3 and Cy5 are brought into proximity by a conformation change in an aptamer, antibody, or receptor, for example, excitation at 540 nm results in an emission at 680 nm.

Quenching dyes can be used as part of the activatable label to quench the fluorescence of visible light-excited fluorophores. Examples of quenching dyes include, but are not limited, to DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs can be considered for FRET associated with the label including, but not limited to, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

The activatable label can include a binding component that is an RNA or DNA oligonucleotide-based aptamer with one or more fluorescent tags and one or more quenching tags. Upon binding of a target component, the aptamer undergoes a conformational shift such that the distance between the donor fluorophore and the acceptor fluorophore or quencher is altered, leading to a change in measurable fluorescence. Aptamers can be isolated from a large library of $10^{14}$ to $10^{15}$ random oligonucleotide sequences using an iterative in vitro selection procedure often termed "systematic evolution of ligands by exponential enrichment" (SELEX). Aptamers can be generated against virtually any class of molecules including cells (e.g., cancer cells, bacteria, and parasites), proteins (e.g., hormones), and chemicals (e.g., codeine, cocaine). See, e.g., Shangguan, et al., *Proc. Natl. Acad. Sci. USA.* 103: 11838-11843; Chen, et al., *Biochem. Biophys. Res. Commun.* 357:743-748, 2007; Ulrich, et al., *J. Biol. Chem.* 277:20756-20762, 2002; Cao, et al. *Current Proteomics* 2:31-40, 2005; Proske, et al. *Appl. Microbiol. Biotechnol.* 69:367-374, 2005, Win, et al. *Nucleic Acids Res.* 34:5670-5682, 2006, each of which is incorporated herein by reference. For example, an aptamer that selectively binds cocaine can be generated using SELEX as described above and modified to incorporate a fluorophore such as, for example, fluorescein and a quencher such as, for example, 4-[4'-((dimethylamino)phenyl)azo-]benzoic acid (DABCYL). See, e.g., Strojanovic, et al. *J. Am. Chem. Soc.* 123:4928-4931, 2001, which is incorporated herein by reference. In this instance, binding of cocaine to the aptamer induces a conformational change in the aptamer that causes the fluorophore and the quencher to move closer in proximity. As such, the presence of cocaine can be measured as a function of the decrease in or quenching of the fluorescein emission at a wavelength of 518 nm.

Semiconductor quantum dots (QDs) with various excitation/emission wavelength properties can be used to label an aptamer-based binding component. Various methods are available for attaching quantum dots to the DNA backbone of an aptamer such as, for example, covalent linkage of amine-modified DNA to carboxylated quantum dots and linkage of biotinylated DNA to streptavidin modified quantum dots. See, e.g., Cady, et al. *J. Mol. Cell. Probes* 21:116-124, 2007, which is incorporated herein by reference. For example, carboxy quantum dots (from, e.g., Quantum Dot Corporation, Hayward, Calif., USA) can be attached to an aptamer through a C6 amino modifier placed on either the 5 prime or 3 prime end of the aptamer sequence. Alternatively, streptavidin quantum dots (from, e.g., Quantum Dot Corporation, Hayward, Calif., USA) can be attached to an aptamer through a biotin attached to the 5-prime end of the aptamer sequence.

The fluorophores can be attached to various chemical moieties that allow for attachment at various sites within the aptamer. For example, 3'-DABCYL CPG can be used to place the fluorophore DABCYL at the 3 prime terminus of the aptamer whereas 5'-DABCYL phosphoramidite can be used to place DABSYL at the 5 prime terminus of the aptamer (see, e.g., product information at Glen Research, Sterling, Va.). DABCYL deoxythymidine (dT) can be used to place DABCYL within the body of the aptamer sequence. Labeling aptamers with appropriate commercially available fluorophores can be achieved following instructions provided by the respective manufacturer. Alternatively, custom made aptamer-based molecular beacons are available from commercial sources (from, e.g., Biosearch Technologies, Inc., Novato, Calif., USA).

In an aspect, an aptamer can have a label in a region of the molecule known to undergo conformational change upon binding a target component that leads to an increase in fluorescence intensity. An aptamer of this sort can be selected using an in vitro selection process with fluorescently labeled aptamers. See, e.g., Jhaveri, et al. *Nature Biotech.* 18:1293-1297, 2000, which is incorporated herein by reference. A pool of RNA molecules is generated in which the random sequence region (45-60 residues) is skewed such that one of the residues, uridine, for example, is disproportionately underrepresented. The three to four randomly placed uridine residues are substituted with fluorescein-12-UTP, Cascade Blue-7-UTP, Texas Red-5-UTP, and/or Rhodamine Green-5-UTP during in vitro transcription. The labeled pool of RNA molecules are screened against a target component by passing the labeled pool over a column matrix or other matrix to which the target component is attached. Those RNA molecules that bind with high affinity to the target component are screened for their fluorescence signaling properties in response to binding of the target component. For example, the baseline fluorescence intensity is measured for RNA aptamer molecules labeled with fluorescein-12-UTP (excitation maxima 494 nm, emission maxima 521 nm) or Rhodamine Green-5-UTP (excitation maxima 505 nm, emission maxima 533 nm), for example, then re-measured in response to increasing concentrations of the target component. As such, fluorescent aptamers can be selected that exhibit a 100-200% increase in fluorescence intensity in response to target binding. See, e.g., Jhaveri, et al. *Nature Biotech.* 18:1293-1297, 2000, which is incorporated herein by reference.

In an aspect, the label configured to bind to one or more target components can include a binding component that is an antibody with one or more donor fluorophore and one or more acceptor fluorophore or quencher. Upon binding of a target component, the antibody undergoes a conformational shift such that the distance between the donor fluorophore and the acceptor fluorophore or quencher is altered, leading to a change in measurable signal, i.e., fluorescence. The antibody can be designed to emit a shift in emission wavelength, for example, in response to binding a target component. An antibody exhibiting a shift in fluorescent signal in response to binding of a target component, i.e., antigen, can be generated by labeling the antibody with a solvent-sensitive fluorophore, e.g., dansyl chloride (5-dimethylaminonaphthalene-1-sulfonyl chloride). See, e.g., Brennan *J. Fluor.* 9:295-312, 1999, which is incorporated herein by reference. The antibody is labeled such that binding of the target component to the antibody shields the solvent sensitive fluorescent label near the active binding site from the solvent water, resulting in a 3-5 fold increase in fluorescence intensity. See, e.g., Bright, et al. *Anal. Chem.* 62:1065-1069, 1990, which is incorporated herein by reference.

In an aspect, the label configured to bind to one or more target components can include a binding component that is an antibody that signals binding of a target component using FRET and a flexible arm. For example, an antibody can include a donor fluorophore near the binding site of the target component as well as a flexible arm containing an analog of the target component that is labeled with a quencher and recognized by the antibody. See, e.g. U.S. Patent Application 2006/0172318 A1, which is incorporated herein by reference. As the labeled target component analog moves into proximity to the labeled active site, a baseline FRET signal can be measured. A measurable change in the FRET signal is detected when the analog is competitively displaced by the actual target component. The flexible arm can be composed of DNA, RNA, polymers, protein nucleic acid (PNA), peptides, protein or oligosaccharide. For example, an amino functionalized DNA arm can be treated with a bifunctional NHS-ester activated Cy3.5 dye to add a fluorescent tag to the flexible arm. The analog of the target component is modified with a monoamine and interacted with the bifunctional NHS-ester and attached to the DNA flexible arm. See, e.g., U.S. Patent Application 2006/0172318 A1, which is incorporated herein by reference. The flexible arm can be attached directly to the antibody through a thiol-maleimide linkage such that the DNA flexible arm is modified with a thiol group at one end and linked via maleimide to one or more cysteine groups on the antibody. Alternatively, the flexible arm can be attached to a protein, for example, that is adjacent to the antibody or to which the antibody is bound.

Device Including First Reservoir for Storing and Releasing Label

The device can include at least one first reservoir that includes one or more labels that bind one or more target components from the blood or lymph of the vertebrate subject. The device can include at least one first reservoir that stores and controllably releases the one or more labels configured to bind to the one or more target components. In an aspect, the device can include a single first reservoir that stores one or more labels configured to bind to one or more target components. In another aspect, the device can include multiple first reservoirs wherein each multiple first reservoir can store one or more labels that bind to one or more target components. The at least one first reservoir can be an integral part of the device. Alternatively, the at least one first reservoir can be a separate part of the device, located proximal to or at a distance from the main body of the device, but in wired or wireless communication with the main body of the device.

The device can include one or more labels configured to bind to one or more target component so that the one or more labels can be released from the at least one first reservoir by one or more release mechanisms. In an aspect, the one or more labels can be continuously released from at least one first reservoir at a constant rate over time. For example, the release mechanism can use one or more of a slow release, controlled release, or extended release biodegradable composition that dissolves or breaks down over time. Examples of slow release, controlled release, or extended release compositions include, but are not limited to, hydrogels, polymers, gelled and/or cross-linked water swellable polyolefins, polycarbonates, polyesters, polyamides, polyethers, polyepoxides and polyurethanes such as, for example, poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(allyl alcohol). Other suitable polymers include, but are not limited to, cellulose ethers, methyl cellulose ethers, cellulose and hydroxylated cellulose, methyl cellulose and hydroxylated methyl cellulose, gums such as guar, locust, karaya, xanthan gelatin, and derivatives thereof. The rate of dissolution of the composition containing the labels can be monitored using an impedance-based sensor. See, e.g., Johnson et al., in *J. Electrochem Soc.* 152:H6-H11, 2005, which is incorporated herein by reference.

In another aspect, the device can include the one or more labels configured to bind one or more target components, wherein the one or more labels can be controllably released from the at least one first reservoir and can include periods of release followed by periods of non-release. Controlled release from at least one first reservoir can include release mechanisms that reversibly open and close a portion of the first reservoir. The release mechanism can include a variety of different types of release mechanisms, including, for example, a controllable valve. Various examples of micro valves or microelectromechanical systems (MEMS) valves for controlling fluid flow have been described. See, e.g., Luckevich M. *Valve World*, May 2007, pp. 79-83; Givrad T K., et al., *Proceedings of BIOMed* 2008, 3$^{rd}$ Frontiers in Biomedical Devices Conference. Jun. 18-20, 2008, Irvine, Calif., USA; U.S. Pat. Nos. 6,612,535; 7,124,773, each of which is incorporated herein by reference.

In an aspect, the device can include the at least one first reservoir covered with a material that can be controllably removed or punctured to release one or more labels. The cover material can be responsive to a directly applied stimulus (e.g., an applied voltage or potential) or to a change in the local environment of the device (e.g., local pH change), or any of a number of other stimuli including, but not limited to, heat, light (e.g., laser), and magnetic field. See, e.g., U.S. Pat. No. 6,808,522; Grayson, R. et al., *Proceedings of IEEE* 92:6-21, 2004, each of which is incorporated herein by reference. As an example, the at least one first reservoir can be an array of microreservoirs on a microchip in which each aliquot of one or more labels are contained in its own reservoir and capped by an environmentally sensitive material. In an aspect, the microreservoirs can be capped with a gold membrane which is weakened and ruptured by electrochemical dissolution in response to application of an anode voltage to the membrane in the presence of chloride ions, resulting in release of contents of the microreservoir as described in U.S. Pat. No. 5,797,898 and in Prescott, et al., *Nat. Biotech.*, 24:437-438, 2006, each of which is incorporated herein by reference. Alternatively, the microreservoirs can be capped by a temperature sensitive material which can be ruptured in response to selective application of heat to one or more of the reservoirs as described in U.S. Pat. No. 6,669,683, which is incorporated herein by reference. Wireless induction of a voltage or thermal trigger, for example, to a given reservoir of a microarray of reservoirs by a vertebrate subject would enable on-demand release of one or more labels or reactive components from the reservoirs.

In some instances, the device can include the at least one first reservoir wherein the at least one first reservoir can incorporate a natural and/or synthetic stimulus-responsive hydrogel or polymer which changes confirmation rapidly and reversibly in response to environmental stimuli, for example, temperature, pH, ionic strength, electrical potential, light, magnetic field or ultrasound. See, e.g., Stubbe, et al., *Pharmaceutical Res.*, 21:1732-1740, 2004, which is incorporated herein by reference. Examples of polymers are described in U.S. Pat. Nos. 5,830,207; 6,720,402; and 7,033,571, each of which is incorporated herein by reference. In some instances, the one or more labels can be dissolved or dispersed in the hydrogel or polymer. Alternatively, a hydrogel and/or other stimulus-responsive polymer can be incorporated into the release mechanism. For example, a hydrogel or other polymer or other smart material can be used as an environmentally sensitive actuator to control flow of an agent out of an implantable device as described in U.S. Pat. Nos. 6,416,495; 6,571,125; and 6,755,621, each of which is incorporated herein by reference. As such, the at least one first reservoir can incorporate a hydrogel or other polymer that modulates delivery of a one or more labels in response to a trigger from the sensor-informed controller.

In some instances, the one or more labels configured to bind one or more target components can be released from the at least one first reservoir as a predetermined dosage. For example, the one or more labels can be administered using continuous infusion. Alternatively, the release of one or more labels from the at least one first reservoir can be linked to a timing mechanism associated with the device. For example, the timing mechanism can instruct release of one or more labels at a given time of day, a given time of week, a given time of month, and/or a given time of year. The timing mechanism can be linked to input from the one or more sensors, releasing one or more labels at one or more predetermined time following detection of one or more target components.

The release of one or more labels from the first reservoir can be programmable, having on/off and/or variable delivery rates based on either external or internal control. External control can be mediated by manual manipulation of a hand-operated pulsative pump with one-way valves associated with a device implanted near the surface of the skin, for example. Alternatively, external control can be mediated by remote control through an electromagnetic wireless signal such as, for example, infrared or radio waves that are able to trigger an electrical stimulus within the implanted device. Examples of remote control drug delivery devices are described in U.S. Pat. Nos. 5,928,195; 6,454,759; and 6,551,235, each of which is incorporated herein by reference. As such, one or more label can be delivered by continuous infusion in response to an "on" trigger and stopped in response to an "off" trigger, for example. Alternatively, one or more label can be delivered as a microbolus, for example, in response to an "on" trigger as described in U.S. Pat. No. 6,554,822, which is incorporated herein by reference. External control can be initiated by a caregiver. Alternatively, a subject can initiate delivery of one or more label. As such, the system can have a built in mechanism to limit the number of allowable doses by a vertebrate subject and/or caregiver in a given time frame as described, for example, in U.S. Pat. No. 6,796,956, which is incorporated herein by reference.

Device Including Energy Sources for Eliciting One or More Signal Responses

The device can include one or more energy sources configured to provide energy to elicit one or more signal responses associated with one or more labeled target components. In an aspect, the one or more energy sources can be configured to elicit one or more signal responses including, but not limited to, electromagnetic signal responses, for example, optical signal responses (e.g., visible light signal responses, infrared signal responses, ultraviolet signal responses, and/or fluorescent signal responses), radiofrequency signal responses, and/or magnetic signal responses. In another aspect, the one or more energy sources can be configured to elicit one or more signal responses including a scattering response and/or an absorptive response from the one or more target components. In an aspect, the one or more signal responses can include, but are not limited to, acoustic signal responses, including, but not limited to, ultrasonic signal responses. One or more signal responses can include, but are not limited to, thermal signal responses, and/or color signal responses. Characteristics of the energy appropriate for generating one or more signal responses are known in the art and/or described herein.

Electromagnetic energy can include, but is not limited to, radio waves, microwaves, terahertz radiation, infrared radiation, visible light, X-rays, and gamma rays. In an aspect, one or more of these frequencies can be explicitly excluded from the general category of electromagnetic energy (e.g. electromagnetic energy sources, but not including X-ray energy sources). Electromagnetic energy, (or radiation) with a wavelength between approximately 400 nm and 700 nm is detected by the human eye and perceived as visible light. Optical light can also include near infrared (longer than 700 nm) and ultraviolet (shorter than 400 nm).

Electromagnetic or optical energy is made up of photons and can include single photon electromagnetic energy, two photon electromagnetic energy, multiple wavelength electromagnetic energy, and extended-spectrum electromagnetic energy. In an aspect, the electromagnetic energy is generated by two photons having the same wavelength. In an aspect, the electromagnetic energy is generated by two photons having a different wavelength. Electromagnetic energy generated by two photons is optionally focused at a depth within a vessel lumen and/or a reservoir, optionally at one or more depths. "Two-photon" energy generation can include excitation of a fluorophore by two photons in a quantum event, resulting in the emission of a fluorescence photon, optionally at a higher energy than either of the two excitatory photons, optionally using a femtosecond laser. In an aspect, two photon electromagnetic energy is coupled through a virtual energy level and/or coupled through an intermediate energy level. "Extended-spectrum" can include a range of possible electromagnetic radiation wavelengths within the full spectrum of possible wavelengths, optionally from extremely long to extremely short.

Electromagnetic energy can be used to induce fluorescence, which includes production of light (emission) following excitation by electromagnetic energy. In an aspect, fluorescence can be emitted from one or more labels bound to one or more target components in response to an excitation energy. In an aspect, inherent fluorescence, e.g., autofluorescence, can be emitted from a target component in response to an excitation energy. In some instances, fluorescence from a label and inherent autofluorescence can be used in combination to generate signal responses associated with one or more labeled target components.

Electromagnetic energy sources can be configured to emit energy as a continuous beam or as a train of short pulses. In the continuous wave mode of operation, the output is relatively consistent with respect to time. In the pulsed mode of operation, the output varies with respect to time, optionally having alternating "on" and "off" periods. In illustrative examples, one or more energy sources can be configured to emit continuous energy to excite fluorophore-based labels to emit fluorescence. In an aspect, the one or more electromagnetic energy sources include one or more lasers having one or more of a continuous or pulsed mode of action. One or more pulsed lasers can include, but are not limited to, Q-switched lasers, mode locking lasers, and pulsed-pumping lasers. Mode locked lasers emit extremely short pulses on the order of tens of picoseconds down to less than 10 femtoseconds, the pulses optionally separated by the time that a pulse takes to complete one round trip in the resonator cavity. Due to the Fourier limit, a pulse of such short temporal length can have a spectrum which contains a wide range of wavelengths.

In an aspect, the energy, optionally electromagnetic energy, can be defined spatially and/or directionally. In an aspect, the electromagnetic energy can be spatially limited, optionally spatially focused and/or spatially collimated. The electromagnetic energy optionally contacts less than an entire possible area, or an entire possible target, and/or is limited to a certain depth within at least one lumen, and/or a reservoir.

In an aspect, the energy, optionally electromagnetic energy, can be directionally limited, directionally varied, and/or directionally variable. In an aspect, the energy can be provided only in a single direction, for example 90 degrees from the horizontal axis of a device, or toward a lumen wall, a bypass wall, and/or a reservoir wall. In an aspect, the energy can be provided over a range of directions for example, through movement of the energy source, through movement of the entire device, and/or through illumination from a variety of energy sources in the device.

In an aspect, the one or more energy sources can be an acoustic energy source configured to induce a signal response. The one or more acoustic energy source can elicit one or more of a signal response using ultrasound imaging. As such, a sound wave can be sent through a piece of quartz or glass coated with a thin layer of piezoelectric material that resonates at a specific frequency, for example, 1 GHz, and through a lens to scan a cell or cells. See, e.g., Ouellette. *The Industrial Physicist* Jun./Jul. 14-17, 2004, which is incorporated herein by reference. The sound waves are reflected back up through the lens and piezoelectric material which serve as detector and amplifier. The reflected sound waves are recorded electronically and can be used directly to compare cellular profiles. Alternatively, the recorded sound waves can be converted into an image.

The resolution of acoustic imaging is dependent upon the frequency of sound used for imaging. Standard ultrasound imaging uses sound waves ranging in frequency from 3-10 MHz, but does not provide cellular detail. Higher frequency ultrasound in the range of 20-100 MHz can be used to detect changes in cellular structures in tissues and cells, although individual cells are still not easily resolved. For example, cells undergoing mitosis and cells undergoing apoptosis in response to a chemotherapeutic agent, for example, exhibit increased backscattered signal relative to normal cells. See, e.g., Baddour et al. *Ultrasonics Symposium IEEE* 2:1639-1644, 2002, which is incorporated herein by reference. Cellular resolution can be attained using sound waves ranging in frequency from 100 MHz to 2 GHz, comparable to the range used for acoustic microscopy. See, e.g., Schenk et al. *J. Histochem. Cytochem.* 36:1341-1351, 1988, which is incorporated herein by reference. The latter corresponds to wavelengths of 15 to 0.75 microns in water, the medium through which ultrasound and acoustic imaging are done.

Photoacoustic imaging, in which ultrasound detection is combined with optical stimulation, can also be used as one or more energy sources to elicit one or more signal responses associated with one or more labeled target components. See, e.g. Wygant et al. *IEEE Ultrasonics Symposium* 1921-1924, 2005, which is incorporated herein by reference. In this process, the optical absorption properties of a material are imaged by detecting the ultrasound emitted when a cell is illuminated with a laser. The emitted ultrasound is due to the brief thermal expansions that occur when the laser energy is absorbed by the cell. Those regions that are more optically absorbent will generate a stronger acoustic signal. Laser pulse widths, for example, of 10 ns and wavelengths between 600 nm and 1000 nm can be used for photoacoustic imaging of cells. A single mechanically scanned piezoelectric transducer or a capacitive micromachined ultrasonic transducer array, for example, can be used to detect the laser generated ultrasound. See, e.g. Wygant et al. *IEEE Ultrasonics Symposium* 1921-1924, 2005, which is incorporated herein by reference.

Photoacoustic imaging can also be used to detect flowing cells in vivo. A cell or cells can be irradiated with one or several focused electromagnetic energy operating at different wavelengths ranging, for example, from 415 to 2300 nm. An ultrasound transducer can be used to record light-induced acoustic waves. See, e.g. Zharov et al. SPIE Newsroom 10.1117/2.1200609.0391, 2006, which is incorporated herein by reference.

Electromagnetic energy and/or acoustic energy configured to induce a signal response in a target can be selected, optionally manually, remotely, programmably, wirelessly, and/or using feedback information. Frequencies that induce a signal response in one or more targets are known in the art and/or discussed herein. In an aspect, selection of excitation energy can be performed in advance, or as a result of information received, optionally including feedback information, optionally from one or more sensors or provided by one or more external sources.

In an aspect, the at least one energy source can be an electrical energy source configured to induce a signal response. The one or more electrical energy sources can elicit one or more of a signal response that is a change in electrical impedance. The change in electrical impedance can be used to assess the relative size of one or more target component. For example, a portion of the lumen can include two or more electrodes between which an electric current flows. A target component, e.g., target cell, passing through the electric current displaces its own volume of conducting fluid (i.e., plasma), momentarily increasing the impedance and inducing a current fluctuation that can be converted into a voltage pulse. The amplitude of the pulse is directly proportional to the volume of the cell that produced it. As such, the device can be configured to detect changes in electrical impedance to generate volume information that can be compared with preset algorithms defining, for example, the volume of normal blood cells, pathological blood cells, and/or cells foreign to the circulation such as pathogen or circulating tumor cells.

Target components of the blood or lymph can be differentiated based on a volume using electrical impedance as described herein and/or commonly practiced using a Coulter counter. For example, platelets range in volume from 2 to 20 femtoliters (fL) whereas red blood cells range in volume from 70-90 fL. Neutrophils and eosinophils range in volume from 160 to 450 fL while monocytes range in volume from 90 to 160 fL. By comparison, bacteria may be as small as 1 fL whereas a circulating tumor cell may be as large as 2000 fL. A MEMS resembling a miniaturized Coulter counter can be incorporated into the device described herein and can be constructed using thin platinum electrodes with a sensing zone of, for example, 20-100 microns. See, e.g., Zheng et al. *Proceedings of* 2006 *International Conference on Microtechnologies in Medicine and Biology, IEEE*, Okinawa, Japan, 9-12 May, 2006; Gao et al. *Proceedings of the 25$^{th}$ Annual International Conference of the IEEE EMBS,* Cancun, Mexico, Sep. 17-21, 2003, each of which is incorporated herein by reference.

Energy sources include, but are not limited to, light-emitting diodes (LED), infrared LED, laser diodes (infrared or near infrared), laser source (Argon-, HeNe-, GaAlAs-, Nd:YAG-type lasers) directed heat source, electromagnetic energy source, The electromagnetic energy source can be one or more laser diode placed in or proximal to the lumen of the blood vessel and capable of producing energy sufficient to excite the fluorescently-labeled metastatic tumor cells. The one or more laser diode can produce energy in the 750-850 nm range that is configured, if needed, to penetrate the blood vessel wall. Near infrared light at 800 nm can at least partially penetrate through 7 millimeters of vertebrate tissue. See, e.g., Fischer, et al., Conference on Lasers and Electro-Optics Europe; CLEO/Europe, 2005; Publication date Jun. 17, 2005, pp. 641, which is incorporated herein by reference. Optionally, wavelengths in a wider range such as 720-904 nm can be used. Laser diodes (3-9 millimeters in diameter) emitting in the far red and near infrared wavelengths are commercially available (from, e.g., JDS Uniphase Corporation, Milpitas, Calif.). Alternatively, the energy source can be one or more far red or near infrared LED chip available in sub-millimeter dimensions (from, e.g., Marubeni America Corporation, Santa Clara, Calif.). The wavelength used by the device depends on the absorbance/emission properties of the label and the tissue penetration depth that is required. Other examples of light or energy sources include, but are not limited to, Argon-, HeNe-, GaAlAs-, Nd:YAG-type lasers.

Device Including Sensors Configured to Detect Signal Responses

The device can include one or more sensors configured to detect one or more signal responses associated with the one or more labeled target components. One or more imaging sensors can include, but are not limited to, one or more electromagnetic energy sensors and/or one or more acoustic sensors, e.g. ultrasonic sensors. One or more electromagnetic energy sensors can include, but are not limited to, one or more photodetectors, one or more radiofrequency antennae, one or more magnetic energy sensors, one or more thermal sensors, and/or one or more electrical energy sensors. One or more electromagnetic energy sensors can include one or more optical sensors including, but not limited to, sensors configured to detect near IR, UV, fluorescence, and/or visual light.

One or more imaging sensors can include, but are not limited to, photodiodes, photoresistors, charged-coupled devices (CCD) and/or complementary metal oxide semiconductor (CMOS) cameras. One or more imaging sensors can include, but are not limited to, one or more piezo transducers, one or more MEMS devices, one or more cavity resonators, one or more magneto resistive sensors, one or more magnetic field sensors, and/or one or more thermal sensors. An example of an implantable CMOS imaging sensor for use in imaging a vertebrate subject in vivo is described in Tamura, et al. *J. Neurosci. Methods* 173:114-120, 2008, which is incorporated herein by reference.

In an aspect, the one or more sensors can be configured to detect one or more signal responses associated with one or more labeled target components that are one or more labeled cells in the blood or lymph of a vertebrate subject. A labeled target component that is a labeled cell can include, for example, a bacterium, a protozoan, a platelet, a red blood cell, a lymphocyte, a monocyte, a neutrophil, an eosinophil, a circulating tumor cell, or a combination there of. A signal response associated with one or more labeled cell can be detected using any of a number of imaging or optical methods including, but not limited to, light scattering, electrical impedance, infrared spectroscopy, acoustic imaging, thermal imaging, photothermal imaging, dark field, visible light absorption and refraction, and autofluorescence. See, e.g., U.S. Patent Application 2009/0093728; Doornbos et al. *Cytometry* 14:589-594, 1993; Gao et al. Proceedings of the 25$^{th}$ Annual International Conference of the IEEE EMBS, Cancun, Mexico, Sep. 17-21, 2003; Oberreuter et al. *Int. J. Syst. Evol. Microbiol.* 52:91-100, 2002; Baddour et al. Ultrasonics Symposium IEEE 2:1639-1644, 2002; Zharov et al. *J. Cell. Biochem.* 97:916-932, 2006; Zharov et al. *J. Biomed. Opt.* 11:054034-1-4, 2006; Koenig et al. *J. Fluoresc.* 4:17-40, 1994; each of which is incorporated herein by reference. For example, red blood cells infected with the parasite *Plasmodium falciparum* can be differentiated from other cells in the blood using differential light scatter at 10 degrees (complexity) and polarized light scatter at 90 degrees (lobularity) based on the pigmentation of the parasite. See, e.g., Mendelow et al. *Br. J. Haematology* 104:499-503, 1999, which is incorporated herein by reference.

In some instances, one or more target cells in the blood or lymph of a vertebrate subject can be recognized based on a spectral analysis of the target cells. Alternatively, the one or more target cells can be recognized based on pattern and image recognition or signal recognition analysis. Various methods have been described for image and shape analysis of cells and subcellular components of cells. See, e.g., U.S. Pat. Nos. 5,107,422; 5,790,691; 6,956,961 B2; 7,151,847 B2; U.S. Patent Applications 2005/0251347 A1; 2006/0039593 A1; Fei-Fei et al. *IEEE Transactions on Pattern Analysis and Machine Intelligence* 28:594-611, 2006; Martin et al. *IEEE Transactions on Pattern Analysis and Machine Intelligence* 26:530-549, 2004; Olson et al. *Proc. Natl. Acad. Sci. USA* 77:1516-1520, 1980; Schneider, et al *Biorheology* 32:237-238, 1995; each of which is incorporated herein by reference. For example, a Texture Analyzing System can be used to distinguish various cells in the blood and/or lymph of a vertebrate subject based on the granularity of the cell or cells. See, e.g., Bins et al. *Cytometry* 1:321-324, 1981, which is incorporated herein by reference. The imaged components of the cells are measured with a gray scale with 33 intervals ranging from black (level 0) to white (level 99) and a histogram is generated. Mature white blood cells (neutrophils, eosinophils, basophils and lymphocytes) have a dense nuclear structure and therefore low counts. In contrast, monocytes have a looser, less dense nuclear structure and high counts. The cytoplasm of eosinophils and neutrophils is very granular and is reflected in the combination of high positive and low negative counts. Smaller values are seen in the cytoplasm of lymphocytes, monocytes and basophils. Similarly, granulometries can be used to identify red blood cells infected with the malarial parasite. See, e.g., Dempster & DiRuberto *Circuits and Systems,* 2001, ISCAS 2001, The 2001 IEEE International Symposium 5: 291-294, May 6-9, 2001, which is incorporated herein by reference.

In an aspect, one or more sensors can be configured to capture one or more signal responses including, but not limited to, electromagnetic signal responses including, but not limited to, optical signal responses (e.g. visible light signal responses, infrared signal responses, ultraviolet signal responses, and/or fluorescent signal responses, among others), radiofrequency signal responses, and/or magnetic signal responses. One or more signal responses can include, but are not limited to, acoustic signal responses, including, but not limited to, ultrasonic signal responses. One or more signal responses can include, but are not limited to, thermal signal responses, and/or color signal responses. In an aspect, one or more sensors are configured to capture one or more signal responses at one or more wavelengths. In an aspect, one or more signal responses described herein and/or known in the art may be specifically excluded from an embodiment, e.g. signal responses not including fluorescent signal responses.

In an aspect, one or more signal responses can include, but are not limited to, actual images of cells or particles within the vessel lumen. In an aspect, one or more signal responses include image information such as cell or particle shape, cell or particle outline, and/or cell or particle periphery, among others. In an aspect, one or more signal responses include image information such as intracellular shapes, intracellular outlines, and/or intracellular peripheries, among others. In an aspect, one or more sensors can be configured to capture light scattering. In an aspect, one or more sensors can be configured to capture fluid and/or cell or particle velocity.

One or more electromagnetic energy sensors can be configured to measure the absorption, emission, fluorescence, or phosphorescence of one or more labeled target components. Such electromagnetic properties can be inherent properties of all or a portion of one or more target components (e.g. autofluorescence), or can be associated with one or more labels added or introduced to the body, surface, lumen, interior, and/or fluid and configured to bind to one or more targets. One or more target components can include, but are not limited to, one or more cells.

In an aspect, one or more sensors can be configured to detect a fluorescent response at a single wavelength of electromagnetic energy, at two wavelengths of electromagnetic energy, at multiple wavelengths of electromagnetic energy, or over extended-spectrum electromagnetic energy. In an aspect, one or more sensors can be configured to detect excitation energy.

In an aspect, one or more sensors can be configured to detect a cumulative (optionally fluorescent) response over a time interval. In an aspect, one or more sensors can be configured to detect a (optionally fluorescent) response at a specific time interval and/or at a specific time. In an aspect, one or more sensors are configured to detect a time-dependent (optionally fluorescent) response. In illustrative examples, the cumulative response is determined over milliseconds, seconds, and/or minutes following excitation. In an aspect, the response is detected over millisecond, second, and/or minute time intervals following excitation. In an, aspect, the response is detected approximately femtoseconds, picoseconds, nanoseconds, milliseconds, seconds, and/or minutes after excitation.

In an aspect, one or more sensors can be configured to be calibrated optionally at least partially based an expected baseline signal response, e.g. normal signal response, for the fluid, tissue, cells, and/or lumen. "Normal signal response" can include the detected intrinsic signal response of one or more fluid, tissue, cells, and/or lumen as determined by researchers and/or medical or veterinary professionals for subjects of a certain age or ethnicity who do not have pathological conditions (e.g. control subjects). Normal signal response can include the intrinsic detected signal response of fluid, tissue, cells, and/or lumen of a vertebrate subject prior to a pathological condition and/or of a comparable location not affected by the pathological condition.

In an aspect, the device can include one or more sensors that can be configured to detect a condition of interest including, but not limited to, a temperature, a pressure, a fluid flow, an optical absorption, optical emission, fluorescence, or phosphorescence, an index of refraction at least one wavelength, an electrical resistivity, a density or sound speed, a pH, an osmolality, the presence of an embolism, the presence or absence of an object, for example, a blood clot, a thrombus, an embolus, a plaque, a lipid, a gas bubble, an aggregate, a cell, a specific type of cell, a cellular component or fragment, a collection of cell, a gamete, a pathogen, or a parasite, and/or the presence or absence of a substance, for example, a biological marker, an antibody, an antigen, a peptide, a polypeptide, a protein, a complex, a nucleic acid, a cell and/or a cell of a particular type, a cellular component, an organelle, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, and/or a pollutant.

In an aspect, the one or more sensors can be radioactivity sensors configured to detect radioactivity associated with a radioactive label bound to one or more target components. Examples of methods for detecting radioactivity include, but are not limited to, gas-filled tube detectors, e.g., Geiger counters; scintillation crystal detectors; and solid-state semiconductor detectors. In an aspect, the one or more radioactivity sensors are one or more of a scintillation crystal detector made from a material that fluoresces or emits light when hit by radiation particles. The fluorescence or light can be measured using one or more of a light capture device, e.g., a photomultiplier or photodiode. In an aspect, the one or more radioactivity sensors are one or more of a microdosimeter. A microdosimeter for wireless measurement of radioactivity in vivo has been described and is configured to detect ionizing radiation using a parallel plate capacitor to form a passive LC resonator. See, e.g., Son & Ziaie. *IEEE Trans. Biomed Eng.* 55:1772-1775, 2008, which is incorporated herein by reference.

In an aspect, the one or more sensors can be one or more magnetic sensors capable of detecting a target component labeled with a magnetic particle. Examples of MEMS magnetic sensors are described in Lee, et al. Magnetics Conference, 2006. INTERMAG 2006. IEEE International; Erye et al., "MEMS Magnetic Sensor in Standard CMOS", in *Science Closure and Enabling Technologies for Constellation Class Mission*, ed. V. Anelopoulos and P. V. Panetta, pp. 99-102, UC Berkeley, Calif., 1998, each of each of which is incorporated herein by reference.

Device Including Additional Sensors

The device can include one or more additional sensors configured to sense target components directly and/or to sense disease-associated physiological parameters. For example, the device can include one or more physiological sensors configured to detect one or more of a body temperature, pH, pressure, edema, oxygen level, or toxin level. One or more physiological sensors can include, but are not limited to, one or more chemical and/or biological molecule sensors, e.g. blood chemistry, chemical concentration, biosensors; one or more pH sensors; one or more time sensors, e.g. timers, clocks; and/or one or more temperature sensors. One or more physiological detectors can include, but are not limited to, blood pressure detectors, pulse detectors, peristaltic action sensors, pressure sensors, flow sensors, viscosity sensors, and/or shear sensors.

The device including one or more sensors can be configured to measure various parameters including, but not limited to, the electrical resistivity of the fluid, the density or sound speed of the fluid, the pH, the osmolality, or the index of refraction of the fluid at least one wavelength. The selection of a suitable sensor for a particular application or use site is considered to be within the capability of a person having skill in the art. One or more of these and/or other sensing capabilities can be present in a single sensor or an array of sensors; sensing capabilities are not limited to a particular number or type of sensors.

One or more biosensors can be configured to detect materials including, but not limited to, a biological marker, an antibody, an antigen, a peptide, a polypeptide, a protein, a complex, a nucleic acid, a cell and, in some cases, a cell of a particular type, e.g., by methods used in flow cytometry. One or more biosensors can be configured to detect materials including, but not limited to, a cellular component, an organelle, a gamete, a pathogen, a lipid, a lipoprotein, an alcohol, an acid, an ion, an immunomodulator, a sterol, a carbohydrate, a polysaccharide, a glycoprotein, a metal, an electrolyte, a metabolite, an organic compound, an organophosphate, a drug, a therapeutic, a gas, a pollutant, or a tag. A biosensor can include an antibody or other binding molecule such as a receptor or ligand.

One or more sensors can include a gas sensor such as an acoustic wave, chemiresistant, or piezoelectric sensors, or an electronic nose. One or more sensors are optionally small in size, for example a sensor or array that is a chemical sensor (Snow, *Science* 307: 1942-1945, 2005), a gas sensor (Hagleitner, et al., *Nature* 414: 293-296, 2001.), an electronic nose, and/or a nuclear magnetic resonance imager (Yusa (2005), Nature 434:1001-1005). Additional examples of sensors are provided in The Biomedical Engineering Handbook, Second Edition, Volume I, J. D. Bronzino, Ed., Copyright 2000, CRC Press LLC, pp. V-1-51-9, and U.S. Pat. No. 6,802,811), each of which is incorporated herein by reference.

The device can include one or more sensors for qualitatively and/or quantitatively measuring one or more target components in the blood of a vertebrate subject. The one or more sensors can include, but are not limited to, one or more of a biosensor, a chemical sensor, a physical sensor, an optical sensor, or a combination thereof. The one or more sensors can include one or more target recognition elements that recognize one or more target components. The interaction of one or more target components with one or more sensors results in one or more detectable signals sent to the controller.

In another aspect, the device including one or more sensors can include one or more target recognition elements or labels that recognize one or more target components. The target recognition elements or labels are configured to specifically bind one or more target components and can include, but are not limited to, antibodies, antibody fragments, peptides, oligonucleotides, DNA, RNA, aptamers, protein nucleic acids, proteins, viruses, enzymes, receptors, bacteria, cells, cell fragments, inorganic molecules, organic molecules, or combinations thereof. The one or more target recognition elements or labels can be associated with one or more substrate integrated into the one or more sensors. Binding of a target component to a specific target recognition element or label activates the sensor.

In an aspect, the one or more sensors can use Förster or fluorescence resonance energy transfer (FRET) to sense one or more target components in the blood or lymph of a vertebrate subject. FRET is a distance-dependent interaction between the electronic excited states of two dye molecules in which excitation is transferred from a donor molecule to an acceptor molecule without emission of a photon. For use in a sensor, the one or more target recognition elements or labels associated with the one or more sensors can include at least one donor molecule and at least one acceptor molecule. Binding of a target component to the target recognition element or label can result in a conformation change in the target recognition element or label, leading to changes in the distance between the donor and acceptor molecules and changes in measurable fluorescence.

A variety of donor and acceptor fluorophore pairs can be considered for FRET associated with the target recognition element or label including, but not limited to, fluorescein and tetramethylrhodamine; IAEDANS and fluorescein; fluorescein and fluorescein; and BODIPY FL and BODIPY FL, and various Alexa Fluor pairings as described herein. The cyanine dyes Cy3, Cy5, Cy5.5 and Cy7, which emit in the red and far red wavelength range (>550 nm) as well as semiconductor quantum dots can also be used for FRET-based detection systems. Quenching dyes can also be used to quench the fluorescence of visible light-excited fluorophores, examples of which include DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs can be considered for FRET associated with the target recognition element including, but not limited to, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

The device including one or more sensors can sense the target components in the blood or lymph of a vertebrate subject using the technique of surface plasmon resonance (for planar surfaces) or localized surface plasmon resonance (for nanoparticles). Surface plasmon resonance involves detecting changes in the refractive index on a sensor surface in response to changes in molecules bound on the sensor surface. In an aspect, the surface of the sensor is a glass support or other solid support coated with a thin film of metal, for example, gold. In an aspect, the sensor surface includes a matrix to which is immobilized one or more target recognition elements that recognize one or more target components. The target recognition elements or labels can be antibodies or fragments thereof, oligonucleotide or peptide based aptamers, receptors or ligands, artificial binding substrates formed by molecular imprinting, or any other examples of molecules and/or substrates that bind cells. As blood or lymph from the vertebrate subject passes by the sensor surface, a target component can interact with a target recognition element or label on the sensor surface. The sensor is illuminated by monochromatic light. Resonance occurs at a specific angle of incident light. The resonance angle depends on the refractive index in the vicinity of the surface, which is dependent upon the concentration of target components on the surface. An example of instrumentation that uses surface plasmon resonance is the BIACORE system (Biacore, Inc. —GE Healthcare, Piscataway, N.J.) which includes a sensor microchip, a laser light source emitting polarized light, an automated fluid handling system, and a diode array position sensitive detector. See, e.g., Raghavan & Bjorkman *Structure* 3:331-333, 1995, which is incorporated herein by reference.

The device including one or more sensors for sensing target components can include one or more label-free optical biosensors that incorporate other optical methodologies, e.g., interferometers, waveguides, fiber gratings, ring resonators, and photonic crystals. See, e.g., Fan, et al., *Anal. Chim. Acta* 620:8-26, 2008, which is incorporated herein by reference.

The device including one or more sensors for sensing target components can include one or more microcantilevers. A microcantilever can act as a biological sensor by detecting changes in cantilever bending or vibrational frequency in response to binding of one or more target components to the surface of the sensor. In an aspect the sensor can be bound to a microcantilever or a microbead as in an immunoaffinity binding array. In another aspect, a biochip can be formed that uses microcantilever bi-material formed from gold and silicon, as sensing elements. See, e.g. Vashist *J. Nanotech Online* 3:DO: 10.2240/azojono0115, 2007, which is incorporated herein by reference. The gold component of the microcantilever can be coated with one or more target recognition elements or labels which upon binding one or more target components cause the microcantilever to deflect. Aptamers or antibodies specific for one or more target components can be used to coat microcantilevers. See, e.g., U.S. Pat. No. 7,097, 662, which is incorporated herein by reference. The one or more sensor can incorporate one or more methods for microcantilever deflection detection including, but not limited to, piezoresistive deflection, optical deflection, capacitive deflection, interferometry deflection, optical diffraction grating deflection, and charge coupled device. In an aspect, the one or more microcantilever can be a nanocantilever with nanoscale components. The one or more microcantilevers and/or nanocantilevers can be arranged into arrays. Both microcantilevers and nanocantilevers can find utility in microelectomechnical systems (MEMS) and/or nanoelectomechnical systems (NEMS).

The device including one or more sensors for sensing target components can include a field effect transistor (FET) based biosensor. In an aspect, a change in electrical signal is used to detect interaction of one or more target components with one or more target recognition elements of the sensor. See, e.g., U.S. Pat. No. 7,303,875, which is incorporated herein by reference.

The device including one or more sensors for sensing one or more target components can incorporate electrochemical impedance spectroscopy. Electrochemical impedance spectroscopy can be used to measure impedance across a natural and/or artificial lipid bilayer. The sensor can incorporate an artificial bilayer that is tethered to the surface of a solid electrode. One or more receptor can be embedded into the lipid bilayer. The one or more receptors can be ion channels that open and close in response to binding of a specific analyte. The open and closed states can be quantitatively measured as changes in impedance across the lipid bilayer. See, e.g., Yang, et al., IEEE SENSORS 2006, EXCO, Daegu, Korea/Oct. 22-25, 2006, which is incorporated herein by reference.

The device including one or more sensors can include cells with binding elements which when bound to target components induce a measurable or detectable change in the cells. The cells can emit a fluorescent signal in response to interacting with one or target components. For example, a bioluminescent bioreporter integrated circuit can be used in which binding of a ligand to a cell induces expression of reporter polypeptide linked to a luminescent response. See, e.g., U.S. Pat. No. 6,673,596; Durick & Negulescu *Biosens. Bioelectron.* 16:587-592, 2001; each of which is incorporated herein by reference. Alternatively, the one or more cells can emit an electrical signal in response to interacting with one or more target components. In an aspect, an implantable biosensor can be used which is composed of genetically-modified cells that respond to target binding by emitting a measurable electrical signal. See U.S. Patent Application 2006/0234369 A1; which is incorporated herein by reference.

The target recognition elements or labels recognized by the one or more sensors can detect one or more target components described herein and broadly including, but not limited to, non-cellular target components such as sugars, lipids, vitamins, minerals, non-protein hormones, proteins, serum proteins, acute phase proteins associated with disease, coagulation or complement related proteins, markers of cellular activation, soluble inflammatory mediators, legal drugs, illicit drugs, and environmental toxins; and cellular target components such as blood cells (e.g., red blood cells, platelets, lymphocytes, monocytes, neutrophils, eosinophils, basophils), viruses (e.g., human immunodeficiency virus (HIV) and the hepatitis B, hepatitis C, and hepatitis D viruses), bacteria (e.g., *Staphylococcus, Streptococcus, Pseudomonas, Haemophilus, Listeria, Esherichia coli*), fungi, (e.g., *Candida albicans, Candida glabrata, Aspergillus, T. glabrata, Candida tropicalis, C. krusei,* and *C. parapsilosis*) parasites (e.g., *Trypanosoma cruzi, Trypanosoma brucei, Leishmania, Plasmodium, Babesia microti, Toxoplasma gondii*) and cancer cells (e.g., metastatic tumor cells, hematopoietic cancer cells).

The one or more target recognition elements or labels can be configured to recognize one or more biomolecules on the surface of the one or more target cells. In an aspect, the one or more target recognition elements, e.g., antibody, aptamer, ligand, or ligand mimetic, can be configured to recognize one or more receptor types on the surface of target cells. Examples of receptors include, but are not limited to, acetylcholine receptors, adenosine receptors, adrenoceptors, GABA receptors, angiotensin receptors, cannabinoid receptors, cholecystokinin receptors, dopamine receptors, glucagon receptors, glucocorticoid receptors, glutamate receptors, histamine receptors, mineralocorticoid receptors, olfactory receptors, opioid receptors, purinergic receptors, secretin receptors, serotonin receptors, somatostatin receptors, steroid hormone receptors, calcium-sensing receptor, hormone receptors, erythropoietin receptor, and natriuretic peptide receptors. Other examples include type I cytokine receptors (e.g., type I interleukin receptors, erythropoietin receptor, GM-CSF receptor, G-CSF receptor, growth hormone receptor, oncostatin M receptor, leukemia inhibitory factor receptor); type II cytokine receptors (e.g., type II interleukin receptors, interferon-α/β receptors, interferon-γ receptor); members of the immunoglobulin superfamily (e.g., interleukin-1 receptor, CSF1, c-kit receptor, interleukin-18 receptor); tumor necrosis factor (TNF) receptor family (e.g., TNF receptor 1 (TNF-R1), TNF receptor 2 (TNF-R2), CD27, CD40, and lymphotoxin β receptor); chemokine receptors including serpentine CCR and CXCR receptors (e.g., CCR1 and CXCR4, and interleukin-8 receptor); TGF β receptors. See Ozaki and Leonard, *J. Biol. Chem.* 277:29355-29358, 2002, which is incorporated herein by reference.

In an aspect, the one or more target recognition elements or labels, e.g., antibody, aptamer, ligand, or ligand mimetic, can be configured to recognize other biomolecules on the surface of target cells including, but not limited to, various CD (cluster of designation/cluster of differentiation) markers, intergrins, ion channels, ATPases, cell adhesion molecules, integral membrane glycoproteins, immunoglobulins, transporters. The one or more target recognition elements can be configured to recognize components of cell surface biomolecules including amino acid sequence and oligosaccharide modifications.

In an aspect, the target recognition element or label, e.g., antibody, aptamer, ligand, or ligand mimetic, can be configured to recognize a biomolecule associated with a tumor cell. Examples of tumor associated components can include, but are not limited to, BLyS receptor, carcinoembryonic antigen (CA-125), CD25, CD34, CD33 and CD123 (acute myeloid leukemia), CD20 (chronic lymphocytic leukemia), CD19 and CD22 (acute lymphoblastic leukemia), CD30, CD40, CD70, CD133, 57 kD cytokeratin, epithelial specific antigen, extracellular matrix glycoprotein tenascin, Fas/CD95, gastrin-releasing peptide-like receptors, hepatocyte specific antigen, human gastric mucin, human milk fat globule, lymphatic endothelial cell marker, matrix metalloproteinase 9, melan A, melanoma marker, mesothelin, mucin glycoproteins (e.g., MUC1, MUC2, MUC4, MUC5AC, MUC6), prostate specific antigen, prostatic acid phosphatase, PTEN, renal cell carcinoma marker, RGD-peptide binding integrins, sialyl Lewis A, six-transmembrane epithelial antigen of the prostate (STEAP), TNF receptor, TRAIL receptor, tyrosinase, villin. Other tumor associated antigens include, but are not limited to, alpha fetoprotein, apolipoprotein D, clusterin, chromogranin A, myeloperoxidase, MyoD1 myoglobin placental alkaline phosphatase c-fos, homeobox genes.

In an aspect, the target recognition element or label, e.g., antibody, aptamer, ligand, or ligand mimetic, can be configured to recognize a biomolecule associated with the surface of a pathogen, e.g., bacteria, a virus, a fungus, or a parasite. The biomolecule can be one or more components of the bacterial outer membrane, cell wall, and/or cytoplasmic membrane. Examples of components associated with the bacterial outer membrane of Gram-negative bacteria include, but are not limited to, lipopolysaccharide and OMP (outer membrane protein) porins, the latter of which are exemplified by OmpC, OmpF and PhoP of $E. coli$. Examples of components associated with the bacterial cell wall of both Gram-positive and Gram-negative bacterial include, but are not limited to, peptidoglycans polymers composed of an alternating sequence of N-acetylglucoamine and N-acetyl-muraminic acid and crosslinked by amino acids and amino acid derivatives. Examples of components associated with the bacterial cytoplasmic membrane include, but are not limited to, the MPA1-C (also called polysaccharide copolymerase, PCP2a) family of proteins, the MPA2 family of proteins, and the ABC bacteriocin exporter accessory protein (BEA) family of proteins. Other examples of components associated with bacteria include, but are not limited to, transporters, e.g., sugar porter (major facilitator superfamily), amino-acid/polyamine/organocation (APC) superfamily, cation diffusion facilitator, resistance-nodulation-division type transporter, SecDF, calcium:cation antiporter, inorganic phosphate transporter, monovalent cation:proton antiporter-1, monovalent cation:proton antiporter-2, potassium transporter, nucleobase:cation symporter-2, formate-nitrite transporter, divalent anion:sodium symporter, ammonium transporter, and multi-antimicrobial extrusion; channels, e.g., major intrinsic protein, chloride channel, and metal ion transporter; and primary active transporters, e.g., P-type ATPase, arsenite-antimonite efflux, Type II secretory pathway (SecY), and sodium-transporting carboxylic acid decarboxylase. A number of other potential components associated with bacteria have been described in Chung, et al., *J. Bacteriology* 183:1012-1021, 2001, which is incorporated herein by reference.

In an aspect, the target recognition element or label can be configured to recognize a biomolecule associated with a blood cell infected with a pathogen. For example, red blood cells infected with *P. falciparum* can be distinguished from normal red blood cells by changes in surface protein expression including expression on the red blood cell surface of the parasite derived protein *P. falciparum* erythrocyte membrane protein (PfEMP1). See, e.g., Horata, et al., *Malaria J.* 8:184, 2009, which is incorporated herein by reference.

Device Including One or More Reactive Components

A device is disclosed herein that includes at least one second reservoir configured to include one or more reactive components responsive to the sensor, wherein the one or more second reservoirs are located in communication with, or located within, the at least one lumen and include the one or more reactive components configured to modulate a physiological effect of the one or more target components in the one or more of blood or lymph of a vertebrate subject. The one or more reactive components, e.g., reactive chemical, components, reactive biologic components or reactive physical components, include, but are not limited to, one or more of a denaturing agent, a degradative agent, a cell-disrupting agent, a modulator, an apoptotic agent, a cytotoxic agent, cytostatic agent, a chemotherapeutic agent, an antibody toxin, or a combination thereof. The one or more reactive chemical components or reactive biologic components configured to modulate a physiological effect of the one or more target components can be any of a number of chemical types or biologic types including, but not limited to, a protein, a peptide, a small molecule, a chemical, a toxin, an aptamer, or an inhibitory RNA, DNA, or other nucleic acid. The one or more reactive components can be incorporated into or released within one or more second reservoirs associated with the device. Alternatively, the one or more reactive components can be diffusible components released from a reservoir of the device into the blood of the vertebrate subject. The one or more reactive components can further include one or more reactive physical components including, but not limited to, one or more of polymers, imprinted polymers, or charged polymers. In an aspect, the one or more reactive physical components can include a charged plastic polymer surface configured to bind cells, tumor cells, emboli, misfolded proteins, aggregated proteins, autoimmune antibodies, infectious agents, or infected cells.

In an aspect, the reactive biologic component can be a recombinant protein or peptide. The recombinant protein or peptide can be generated exogenously and incorporated into one or more second reservoirs of the device. In an aspect, the recombinant protein or peptide can be generated by one or more cells incorporated into the device. The one or more cells can be genetically modified to synthesize and secrete the one or more reactive biologic components. Cells that can be used for this purpose include, but are not limited to, mammalian cells, enucleated cells (e.g., erythrocytes), plants cells, insect cells, bacteria, or yeast. DNA sequences corresponding to one or more reactive biologic components are cloned into an appropriate cell type using standard procedures with appropriate expression vectors and transfection protocols. The genetically modified cells are encapsulated in one or more compartments of the device and secrete the one or more reactive biologic components into the blood or lymph of a vertebrate subject. The genetically modified cells are kept separate from the circulation of the vertebrate subject using a size-limiting biocompatible mesh or membrane filter, for example, that allows passage of the cytotoxic, cytostatic, apoptotic, and/or chemotherapeutic agent, but not the larger cells.

In an aspect, the one or more reactive chemical components or reactive biologic components can be released from synthetic vesicles or particles. Examples include any of a number of drug delivery vehicles including, but not limited to, phospholipid vesicles, liposomes, nanoparticles, polymers, or hydrogels. The release of the one or more reactive chemical component or reactive biologic component can be triggered by binding of a specific target to the synthetic vesicle or particle. For example, one or more DNA aptamers can be incorporated into hydrogel and designed to bind one or more specific targets and release the contents of the hydrogel as described herein.

The device can include one or more reservoirs that store one or more reactive components. The one or more reservoirs of the device can be configured to controllably release one or more reactive components. Each reservoir can contain one or more reactive components. Release of the reactive component from a reservoir is controlled by the controller component of the device. In an aspect, the reactive components can be housed in multiple reservoirs associated with the device. For example, the device can include one or more microchips each with multiple reservoirs sealed with removable caps to enable controlled release of one or more a denaturing agent, a degradative agent, a cell-disrupting agent, a modulator, an apoptotic agent, a cytotoxic agent, cytostatic agent, a chemotherapeutic agent, an antibody toxin, reactive physical components, or a combination thereof. See, e.g., U.S. Pat. No. 7,413,846; Maloney & Santini, Proceedings 26$^{th}$ Annual International Conference IEEE EMBS, San Francisco, Calif., USA, Sep. 1-5, 2004, which is incorporated herein by reference.

Binding agents remove one or more target components from the blood. The device can include one or more reactive components that are binding agents configured to remove one or more labeled target components from the blood or lymph of a vertebrate subject. The one or more binding agents can be used alone to selectively or non-selectively bind and sequester one or more target components or target cells from the blood or lymph of the vertebrate subject. Alternatively, the one or more binding agents can be used to capture one or more labeled target components in combination with a treatment including one or more additional reactive components, e.g., a second binding agent, a cell-disrupting agent, a cytotoxic agent, a cytostatic agent, an apoptotic agent, a chemotherapeutic agent, an antibody-toxin agent, or a combination thereof. Following binding of the one or more labeled target components to the one or more binding agents in at least one lumen, one or more additional reactive components can be provided to modulate a physiological effect of the one or more target components.

The one or more binding agents can be configured to non-selectively bind one or more labeled target components. For example, the binding agents can constitute all or part of one or more components of extracellular matrix, e.g., fibronectin, vitronectin, collagen, and laminin to which cells expressing integrins and other cell surface components will non-selectively bind. Alternatively, the binding agents can constitute all or part of one or more components of basal lamina, e.g., collagen, heparan sulfate proteoglycan, laminin, integrins, or dystroglycans, to which cells expressing cell adhesion molecules and other cell surface components will non-selectively bind. In an aspect, the binding agent can be one or more of a commercially available cell adhesion product (e.g., BD MATRIGEL™ from BD Biosciences, San Jose, Calif.). In an aspect, the one or more binding agent can be a surface substrate that non-selectively binds target cells, which include, but are not limited to, glass or plastic.

The one or more binding agents can include absorbent material that non-selectively binds one or more labeled target component. The absorbent material can include, but is not limited to, silica, activated charcoal, nonionic or uncharged resins or polymers, ionic or charged resins or polymers, anion exchange resins or polymers, cation exchange resins or polymers, neutral exchange resins or polymers, immobilized polymyxin B, immobilized monoclonal antibodies, immobilized inflammatory mediator receptors, immobilized specific antagonists, cellulose, cellulose derivatives, synthetic materials, polysulfone, polyacrylonitrile, polymethylmethacrylate, polyvinyl-alcohol, polyamide, polycarbonate, polystyrene-derivative fibers, and any combination thereof. Specific examples of absorbent materials that have been used in animal and clinical studies for non-specific binding of inflammatory mediators, for example, include, but are not limited to, polystyrene-divinylbenzene copolymer beads with biocompatible polyvinylpyrrolidone coating (CYTOSORB, MedaSorb Corporation, NJ, USA) and 2-methacryloyloxyethyl phosphorylcholine (MPCF-X; see, e.g., Nakada, et al., *Transfus. Apher. Sci.* 35:253-264, 2006, which is incorporated herein by reference.

In an aspect, the one or more binding agents can include one or more biomolecules that non-specifically bind immunoglobulins, including, but not limited to, anti-immunoglobulin antibodies, Protein A and Protein G. In an aspect, the binding agent can be avidin or streptavidin for binding biotinylated target components. Alternatively, the binding agent can be biotin for binding avidin or streptavidin labeled target components.

The one or more binding agents can be configured to selectively bind one or more labeled target component. A selective binding agent of one or more target cells can include, but is not limited to, antibodies, antibody fragments, peptides, oligonucleotides, DNA, RNA, aptamers, protein nucleic acids proteins, receptors, receptor ligands, lectins, viruses, enzymes, receptors, bacteria, cells, cell fragments, inorganic molecules, organic molecules, an artificial binding substrate formed by molecular imprinting, or other examples of biomolecules and/or substrates that bind cells. The reactive components can include one or more of an adhesion molecule, a binding mimetic, a polymer, a lectin, integrin, or selectin.

The one or more binding agents can include one or more antibodies that bind one or more labeled target components. Antibodies, or fragments thereof, for use as one or more binding agents labeled target components can include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, chimeric antibodies, non-human antibodies, fully human antibodies, among others. Single chain or multiple chain antigen-recognition sites can be used. Multiple chain antigen-recognition sites can be fused or unfused. Antibodies or fragments thereof can be generated using standard methods. See, e.g., Harlow & Lane, *Antibodies: A Laboratory Manual*, Cold Spring Harbor Laboratory Press; 1$^{st}$ edition 1988, which is incorporated herein by reference. Alternatively, an antibody or fragment thereof directed against one or more target component can be generated, for example, using phage display technology. See, e.g., Kupper, et al. *BMC Biotechnology* 5:4, 2005, which is incorporated herein by reference. An antibody, a fragment thereof, or an artificial antibody, e.g., Affibody® artificial antibodies (Affibody AB, Bromma, Sweden) can be prepared using in silico design (Knappik et al., *J. Mol. Biol.* 296: 57-86, 2000, which is incorporated herein by reference. In an aspect, antibodies directed against one or more target component may be available from a commercial source (from, e.g., Novus Biological, Littleton, Colo.; Sigma-Aldrich, St. Louis, Mo.; United States Biological, Swampscott, Mass.).

The one or more binding agents can include one or more aptamers that bind one or more labeled target components. The aptamer can be an oligonucleotide RNA- or DNA-based aptamer. Aptamers are artificial oligonucleotides (DNA or RNA) which can bind to a wide variety of entities (e.g., metal ions, small organic molecules, proteins, and cells) with high selectivity, specificity, and affinity. Aptamers can be isolated from a large library of $10^{14}$ to $10^{15}$ random oligonucleotide sequences using an iterative in vitro selection procedure often termed "systematic evolution of ligands by exponential enrichment" (SELEX). See, e.g., Cao, et al., *Current Proteomics* 2:31-40, 2005; Proske, et al., *Appl. Microbiol. Biotechnol.* 69:367-374, 2005; Jayasena *Clin. Chem.* 45:1628-1650, 1999, each of which is incorporated herein by reference.

In an aspect, the one or more binding agents can include one or more aptamers that are peptide based aptamers. Peptide aptamers are artificial proteins in which inserted peptides are expressed as part of the primary sequence of a structurally stable protein. See, e.g., Crawford, et al., *Brief Funct. Genomic Proteomic* 2:72-79, 2003, which is incorporated herein by reference.

The one or more binging agents can include one or more peptide receptor ligands that bind receptors associated with one or more target cells. Examples of peptide receptor ligands have been described herein and generally include, but are not limited to, neuropeptides, cytokines, chemokines, growth factors, and other peptide hormones including atrial natriuretic factor, insulin, glucagon, angiotensin, prolactin, oxyocin, and others. In an aspect, the one or more binding agents can include one or more novel peptides. Novel peptides that bind selective targets can be generated using phage display methodologies. See, e.g., Spear, et al., *Cancer Gene Ther.* 8:506-511, 2001, which is incorporated herein by reference.

The one or more binding agents can include one or more artificial binding substrates for one or more labeled target component formed by the process of molecular imprinting. In the process of molecular imprinting, a template is combined with functional monomers which upon cross-linking form a polymer matrix that surrounds the template, the process and materials of which have been described herein. See, e.g., Alexander, et al., *J. Mol. Recognit.* 19:106-180, 2006; U.S. Pat. No. 7,319,038; Byrne et al., *Advanced Drug Delivery Reviews,* 54: 149-161, 2002; U.S. Pat. Nos. 6,255,461; 5,804, 563; 6,797,522; 6,670,427; and 5,831,012; U.S. Patent Application 20040018508; Ye & Haupt, *Anal Bioanal Chem.* 378: 1887-1897, 2004; Peppas & Huang, *Pharm Res.* 19: 578-587 2002, each of which is incorporated herein by reference.

Reactive components can include denaturing agents that modulate a physiological effect of the one or more target components. The device including one or more reactive chemical components can include one or more denaturing agents. Denaturing includes changing one or more inherent characteristics or properties of a cell, including cell constituents, protein, lipid, or nucleic acid, to thereby negatively affect the cell and the cellular components. Denaturing can include reducing a cell, protein, lipid, or nucleic acid constituents to smaller components. Denaturing can further include destroying cells, including cell constituents, protein, lipid, or nucleic acid. Modulating a physiological effect of the one or more target components can occur by the process of denaturation in which the secondary, tertiary or quaternary structure of the one or more target components can be altered by denaturing agents. Examples of denaturing agents include, but are not limited to, acids such as acetic acid, trichloroacetic acid (TCA), sulfosalicyclic acid, picric acid; solvents such as methanol, ethanol, and acetone; cross-linking agents such as formaldehyde and gluteraldehyde; chaotropic agents such as urea, guanidinium chloride, and lithium perchlorate; and disulfide bond reducers such as 2-mercaptoethanol, dithithreitol, TCEP, anionic detergents, or cationic detergents. In an aspect, acids can be used to denature a protein molecule by exposing the protein molecule to a pH below its isoelectric point. Under these conditions, the protein molecule will lose its negative charge and retain only positive charges. The like positive charges can repel one another and in areas of large charge density, the intramolecular repulsion can be sufficient enough to cause unfolding of the protein. The one or more denaturing agents can be incorporated into or released within one or more second reservoirs of the device. Alternatively, the one or more denaturing agents can be released by the device as diffusible agents into the blood or lymph.

Reactive components can include degradative agents that modulate a physiological effect of the one or more target components. Modulating a physiological effect of the one or more target components can occur by the one or more degradative agents that act by breaking peptide bonds within the primary amino acid sequence of the one or more target components. The one or more degradative agents can include any of a number of agents designed to cleave one or more peptide bonds of the primary amino acid sequence of one or more target components. The one or more degradative agents can include any of a number of agents designed to cleave nucleic acids, lipids, or proteins associated with cells or particles of the target component. Examples of degradative agents, include, but are not limited to, proteases, strong acids, strong bases, free radicals, natural or synthetic proteasomes, or photoactivatable agents. The one or more degradative agents can be incorporated into or released within one or more second reservoirs of the device. Alternatively, the one or more degradative agents can be released by the device as diffusible agents into the blood.

The device including one or more degradative agents can include one or more proteases. Examples of proteases include, but are not limited to, serine proteases, e.g., as trypsin, chymotrypsin, elastase, dipeptidyl peptidase IV, and subtilisin; cysteine proteases, e.g., papain, cathepsins, caspases, calpains; aspartic acid proteases, e.g., pepsin, renin, and HIV-proteases; metalloproteases, e.g. carboxypeptidases, aminopeptidases, and matrix metalloproteases, e.g. MMP1 through MMP28. The one or more proteases can be free in solution. Alternatively, the one or more proteases can be bound to a substrate. In an aspect, trypsin can be bound to glass beads. See, e.g., Lee, et al., *J. Dairy Sci.,* 58:473-476, 1974, which is incorporated herein by reference. Alternatively, trypsin and other proteases can be bound to an agarose matrix. Sources of immobilized proteases including trypsin and pepsin are available from commercial sources (Pierce Chemicals, Rockford, Ill.; Applied Biosystems, Foster City, Calif.).

The device including one or more degradative agents can include a natural or synthetic complex of proteases. In an aspect, the one or more target components can be subject to degradation using proteasomes. A proteasome is a naturally occurring large protein complex that contains multiple subunits. The complex includes several protease activities, for example, chymotrypsin-like activity, trypsin-like activity, glutamic acid protease activity, and threonine protease activity. Proteasome complexes can be purified from fractionated cells using ultracentrifugation through a 10-40% glycerol gradient. See, e.g., Pervan, et al., *Mol. Cancer Res.* 3:381-390, 2005, which is incorporated herein by reference. Proteasomes can be isolated using a commercially available isolation kit. (Proteasome Isolation Kit, Human 539176-1KIT, Calbiochem (EMD Chemicals, Inc.; Gibbstown, N.J.).

The device including one or more degradative agents can include an agent that selectively targets one or more target component for degradation. In an aspect, the one or more target components can be covalently tagged with ubiquitin for selective destruction by proteasomes. Ubiquitin is a small and highly conserved protein. An isopeptide bond links the terminal carboxyl of ubiquitin to the s-amino group of a lysine residue of a protein targeted for degradation. The joining of ubiquitin to the targeted protein is ATP-dependent. Three enzymes are involved, designated E1, E2 and E3. Initially, the terminal carboxyl group of ubiquitin is joined in an ATP-dependent thioester bond to a cysteine residue on ubiquitin-activating enzyme (E1). The ubiquitin is then transferred to a sulfhydryl group on a ubiquitin-conjugating enzyme (E2). A ubiquitin-protein ligase (E3) then promotes transfer of ubiquitin from E2 to the $\epsilon$-amino group of a lysine residue of a protein recognized by that E3, forming an isopeptide bond. There are distinct ubiquitin ligases with differing substrate specificity. In addition, some proteins have specific sequences termed a "destruction box" that is a domain recognized by a corresponding ubiquitin ligase. In general, E1, E2, and E3 can be isolated from natural sources or generated using standard molecular biology techniques and used to ubiquinate proteins in vitro. See, e.g., Chen, et al., *EMBO Rep.* 2: 933-938, 2001, which is incorporated herein by reference. In an aspect, the E2 ligase can be genetically engineered in such a manner as to recognize a specific substrate. See, e.g., Colas, et al., *PNAS* 97:13720-13725, 2000, which is incorporated herein by reference. The device including the one or more degradative agents can include one or more genetically engineered E2 ligase enzymes capable of adding ubiquitin to and facilitating degradation of the one or more target components in the blood of the vertebrate subject.

In an aspect, the ubiquitin can be indirectly associated with the one or more target components. In an aspect, the ubiquitin can be linked to an antibody or aptamer structural component of the label. Binding of the ubiquitin-labeled antibody or aptamer to one or more target components can mark the protein conjugate for degradation by proteasomes.

The device including one or more degradative agents can include a strong acid. Acid hydrolysis can result in degradation of the one or more target components. In an aspect, strong acids such as hydrochloric acid or sulfuric acid can be used to break the carbon-nitrogen peptide bond. Degradation of one or more target components by acid hydrolysis can be optionally performed in combination with elevated temperature, a nitrogen atmosphere and/or microwave energy.

The device including one or more degradative agents can include one or more free radical reactive oxygen species. Examples of reactive oxygen species include, but are not limited to, singlet molecular oxygen, superoxide ion, hydrogen peroxide, hypochlorite ion, hydroxyl radical. Reactive oxygen species can react directly with proteins, targeting peptide bonds or amino acid side chains. See, e.g., Davies, *Biochem. Biophys. Res. Commun.* 305:761-770, 2003, which is incorporated herein by reference. A number of the reactions mediated by reactive oxygen species lead to introduction of carbonyl groups into the protein which in turn can result in inactivation of the protein by cleavage of the peptide bound to yield lower-molecular weight products, cross-linking of proteins to yield higher-molecular weight products, or loss of catalytic function or structural function by distorting secondary and tertiary structure, or combination thereof. Reactive oxygen species can induce a amidation, diamide, glutamate oxidation and/or proline oxidation which can lead to cleavage of peptide bonds. Reactive oxygen species can be formed by the interaction of biological molecules with components including, but not limited to, ionizing radiation, as a byproduct of cellular respiration, and dedicated enzymes such as NADPH oxidase and myeloperoxidase.

In an aspect, the device including one or more degradative agents can include reactive oxygen species that are singlet oxygen species. Singlet oxygen can cause damage to both the side-chains and backbone of amino acids, peptides, and proteins. See, e.g., Davies, *Biochem. Biophys. Res. Commun.* 305:761-770, 2003, which is incorporated herein by reference. Singlet oxygen species can react with tryptophan, tyrosine, histidine, methionine and/or cysteine and cystine residues within a polypeptide and can cause increased susceptibility to proteolytic enzymes, an increased extent/susceptibility to unfolding, changes in conformation, an increase in hydrophobicity, and changes in binding of co-factor and metal ions. In particular, the interaction of tyrosine with singlet oxygen species can lead to fragmentation or cleavage of the polypeptide. See, e.g., Davies, *Biochem. Biophys. Res. Commun.* 305: 761-770, 2003, which is incorporated herein by reference.

The device including one or more degradative agents can include one or more singlet oxygen species generated by a photosensitizer, a chemical which upon exposure to a given wavelength of light emits singlet oxygen species. Examples of photosensitizers include, but are not limited to, porphyrin derivatives such as porfimer sodium, which is excited by red light at 630 nm; chlorins and bacteriochlorins such as bonellin (maximum absorbance 625 nm), mono-L-aspartyl chlorine e6 (max abs 654), m-tetrahydroxyphenyl chlorine (mTHPC, max abs 652 nm), and tin etiopurpurin (SnET2, maximum absorbance 660 nm); benzoporphyrin derivatives such as veteroporfin (also labeled BPD-MA, maximum absorbance 690 nm), 5-aminolaevulinic acid (ALA, porphoryin precursor to PpIX (maximum absorbance 635 nm)); texaphyrins such as lutetium texaphyrin (Lu-Tex, maximum absorbance 732), Phthalocyanines and naphthalocyanines (maximum absorbance 670-780 nm); and cationic photosensitizers such as rhodamine 123 and methylene blue. See, e.g., Prasad (2003) *Introduction to Biophotonics*, John Wiley & Sons, Inc. Hoboken, N.J. Tunable quantum dots (QDs), especially those absorbing in the wavelength range of 600 to 800 nm, also emit singlet oxygen species in response to light and can be useful as photosensitizers. See, e.g., Samia, et al. (2006) *Photochem. Photobiol.* 82:617-625, which is incorporated herein by reference.

Reactive components can include target component-disrupting agents that modulate a physiological effect of the one or more target components. The device including one or more reactive components can include one or more target component- or target cell-disrupting agents. Examples of target component- or target cell-disrupting agents include, but are not limited to, alcohols and other organic solvents such as methanol, ethanol, isopropanol, and acetone; cross-linking aldehydes such as formaldehyde and gluteraldehyde; oxidizing agents such as sodium hypochlorite, calcium hypochlorite, chloramine, chlorine dioxide, hydrogen peroxide, iodine, ozone, acidic electrolyzed water, peracetic acid, performic acid, potassium permanganate, potassium peroxymonosulfate; acids such as acetic acid, trichloroacetic acid (TCA), sulfosalicyclic acid, picric acid; phenolics such as phenol, O-phenylphenol, chloroxylenol, hexachlorophene, thymol; chaotropic agents such as urea, guanidinium chloride, and lithium perchlorate; and disulfide bond reducers such as 2-mercaptoethanol, dithiothreitol; and quaternary ammonium compounds. For example, organic solvents such as methanol, ethanol or acetone can disrupt a target component or target cell by solubilizing the lipids in the plasma membrane and allowing the soluble contents of the cell to be released. In an aspect, the one or more target component- or target cell-disrupting agents are incorporated into or released within one or more second reservoirs of the device. In an aspect, the one or more target component- or target cell-disrupting agents are released by the device as diffusible agents into the blood.

Modulating a physiological effect of the one or more target component or target cells can occur by the one or more target component- or target cell-disrupting agents breaking peptide bonds within the primary amino acid sequence of proteins and peptides associated with one or more target components or target cells. In an aspect, the device including one or more target component- or target cell-disrupting agents can include one or more proteases. Examples of proteases include, but are not limited to, serine proteases, e.g., as trypsin, chymotrypsin, elastase, dipeptidyl peptidase IV, and subtilisin; cysteine proteases, e.g., papain, cathepsins, caspases, calpains; aspartic acid proteases, e.g., pepsin, renin, and HIV-proteases; metalloproteases, e.g. carboxypeptidases, aminopeptidases, and matrix metalloproteases, e.g. MMP1 through MMP28. In an aspect, the one or more proteases are free in solution. In an aspect, the one or more proteases are bound to a substrate.

The device including one or more target component- or target cell-disrupting agents can include one or more free radical reactive oxygen species. Examples of reactive oxygen species include, but are not limited to, singlet molecular oxygen, superoxide ion, hydrogen peroxide, hypochlorite ion, hydroxyl radical. Reactive oxygen species can react directly with proteins associated with the one or more target cells, targeting peptide bonds or amino acid side chains. In an aspect, the device including one or more target component- or target cell-disrupting agents can include reactive oxygen species that are singlet oxygen species. Singlet oxygen can cause damage to both the side-chains and backbone of amino acids, peptides, and proteins. See, e.g., Davies, *Biochem. Biophys. Res. Commun.* 305: 761-770, 2003, which is incorporated herein by reference. The target component- or target cell-disrupting agents can include one or more singlet oxygen species generated by a photosensitizer. Examples of photosensitizers various classes of photosensitizers have been described herein. A number of cell types including cancer cells and bacterial pathogens are at least partially inactivated in response to treatment with photosensitizers such as phthalocyanines, phenothiazines, and porphyrins. See, e.g., Miller, et al., *Toxicol. Appl. Pharmacol.* 224:290-299, 2007; Jori, et al., *Lasers Surg. Med.* 38:468-481, 2006; Keefe, et al., *Lasers Surg. Med.* 31:289-293, 2002, each of which is incorporated herein by reference.

Modulating a physiological effect of the one or more target components. The device can include one or more reactive components that can modulate a physiological effect of the one or more target components in the blood of a vertebrate subject. The one or more modulators are reactive components that can be incorporated into or released within one or more second reservoirs of the device. Alternatively, the one or more modulators can be released by the device as diffusible agents into the blood. A modulator can alter, modify, reduce or eliminate the activity of one or more target components by preventing the binding of one or more target components to their respective cognates. Alternatively, a modulator can alter, modify, reduce or eliminate the activity of one or more target components by inhibiting the enzymatic activity, e.g., phosphorylation activity, of the one or more target components. Alternatively, the one or more modulators can indirectly alter, modify or eliminate the activity of one or more target components by attenuating the gene expression of one or more target components. In an aspect, the one or more modulators can indirectly alter or eliminate the activity of one or more target components by increasing the expression of endogenous antagonists of the one or more target components.

In general, the one or more modulator can be a protein, a peptide, a small molecule, an aptamer, or an inhibitory RNA, DNA, or nucleic acid. Modulators are contemplated that either directly or indirectly antagonize the activity of one or more target components and/or attenuate expression of one or more target components.

In an aspect, the one or more modulator can be designed to block the activity or binding properties of one or more target components that is an inflammatory mediator. Examples of modulators of inflammatory mediator activity and binding include, but are not limited to, antibodies, e.g., infliximab, adalimumab, basiliximab efalizumab; soluble receptors, e.g., etanercept, abatacept, alefacept; corticosteroids, e.g., hydrocortisone, cortisone, prednisone, prednisolone, methylprednisolone, meprednisone, triamcinolone, paramethsone, fluprednisolone, betametasone, and dexamethasone; nonsteroidal anti-inflammatory drugs (NSAIDS), e.g., selective cycloxygenase (COX) inhibitors exemplified by celecoxib, etoricoxib, meloxicam, and valdecoxib and non-selective COX inhibitors exemplified by diclofenac, difluisal, etodolac, fenoprofen, fluripofen, ibuprofen, indomethacin, ketoprofen, ketorolac, nabumetone, naproxen, oxaprozin, piroxicam, sulindac, tenoxica, tiaprofen, tolmetin, azapropazone, and carprofen; and, e.g., methotrexate, azathioprine, pennicillamine, hydroxychloroquine, chloroquine, cyclophosphamide, cyclosporine, mycophenolate mofetil, gold, and sulfasalazine.

Reactive chemical components can include cytotoxic, cytostatic, apoptotic, and/or chemotherapeutic agents that modulate a physiological effect of the one or more target cell components. The device including one or more reactive chemical component, reactive biologic components, or reactive physical components can include one or more of a cytotoxic, a cytostatic, an apoptotic, and/or a chemotherapeutic agent. Reactive chemical components, reactive biologic components, or reactive physical components that are cytotoxic, cytostatic, apoptotic, and/or chemotherapeutic agents are contemplated that either directly or indirectly inactivate or kill one or more target cells. Examples of cytotoxic, cytostatic, apoptotic, and/or chemotherapeutic agents include, but are not limited to, vinca alkaloids (e.g., vinblastine, vincristine, vinflunine, vindesine, vinorelbine); taxanes (e.g., docetaxel, larotaxel, ortataxel, paclitaxel, tesetaxel); epothilones (e.g., ixabepilone); dihydrofolate reductase inhibitors (e.g., aminopterin, methotrexate, pemetrexed); thymidylate synthase inhibitors (e.g., raltitrexed); adenosine deaminase inhibitor (e.g., pentostatin); halogenated/ribonucleotide reductase inhibitors (e.g., cladribine, clofarabine, fludarabine); thiopurine (e.g., thioguanine, mercaptopurine); thymidylate synthase inhibitors (e.g., fluorouracil, capecitabine, tegafur, carmofur, floxuridine); DNA polymerase inhibitors (e.g., cytarabine); ribonucleotide reductase inhibitor (e.g., gemcitabine, hydroxyurea); hypomethylating agent (e.g., azacitidine, decitabine); camptotheca (e.g., camptothecin, topotecan, irinotecan, rubitecan, belotecan); podophyllum (e.g., etoposie, teniposide); anthracyclines (e.g., aclarubicin, daunorubicin, doxorubicin, epirubicin, idarubicin, amrubicin, pirarubicin, valrubicin, zorubicin); anthracenediones (e.g., mitoxantrone, pixantrone); nitrogen mustards (e.g., mechlorethamine, cyclophosphamide, chlorambucil, bendamustine, uramustine, estramustine); nitrosureas (e.g., carmustine, lomustine, fotemustine, nimustine, ranimustine, streptozocin); aziridines (e.g., carboquone, thioTEPA, triziquone, triethylenemelamine); platinum (e.g., carboplatin, cisplatin, nedaplatin, oxaliplatin, triplatin, tetranitrate, satraplatin); hydrazines (e.g., procarbazine); triazenes (e.g., dacarbazine, temozolomide, altretamine, mitobronitol); *streptomyces* (actinomycin, bleomycin, mitomycin, plicamycin); aminolevulinic acid/methyl aminolevulinate; efaproxiral; porphyrin derivatives (porfimer sodium, talaporfin, temoporfin, verteporfin); farnesyltransferase inhibitors, cyclin-dependent kinase inhibitors, proteasome inhibitors, phosphodiesterase inhibitors, IMP dehydrogenase inhibitors, lipooxygenase inhibitors, PARP inhibitors, endothelin receptor antagonists (e.g., atrasentan); retinoid X receptor (e.g., bexarotine); sex steroid (e.g., testolactone); amsacrine, trabectedin, alitretinoin, tretinoin, arsenic trioxide, celecoxib, demecolcine, elesclomol, elsamitrucin, etoglucid, lonidamine, lucanthone, mitoguazone, mitotane, oblimersen, temsirolimus, vorinostat. The cytotoxic agent can be a biological agent, a peptide, a protein, an enzyme, a receptor and/or an antibody. Examples of biological agents currently used to treat cancer include, but are not limited to, cytokines such as interferon-α, interferon-γ, and interleukin-2, an enzyme such as asparaginase, and monoclonal antibodies such as alemtuzumab, bevacizumab, cetuximab, gemtuzumab, rituximab, and trastuzumab.

The device including one or more reactive chemical components, reactive biologic components, or reactive physical components that include one or more cytotoxic, cytostatic, apoptotic, and/or chemotherapeutic agents can include one or more of an antibacterial drug. Examples of antibacterial drugs include, but are not limited to, beta-lactam compounds (e.g., penicillin, methicillin, nafcillin, oxacillin, cloxacillin, dicloxacilin, ampicillin, ticarcillin, amoxicillin, carbenicillin, and piperacillin); cephalosporins and cephamycins (e.g., cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxine, ceftriaxone, cefixime, cefpodoxime, proxetil, cefdinir, cefditoren, pivoxil, ceftibuten, moxalactam, and cefepime); other beta-lactam drugs (e.g., aztreonam, clavulanic acid, sulbactam, tazobactam, ertapenem, imipenem, and meropenem); other cell wall membrane active agents (e.g., vancomycin, teicoplanin, daptomycin, fosfomycin, bacitracin, and cycloserine); tetracyclines (e.g., tetracycline, chlortetracycline, oxytetracycline, demeclocycline, methacycline, doxycycline, minocycline, and tigecycline); macrolides (e.g., erythromycin, clarithromycin, azithromycin, and telithromycin); aminoglycosides (e.g., streptomycin, neomycin, kanamycin, amikacin, gentamicin, tobramycin, sisomicin, and netilmicin); sulfonamides (e.g., sulfacytine, sulfisoxazole, silfamethizole, sulfadiazine, sulfamethoxazole, sulfapyridine, and sulfadoxine); fluoroquinolones (e.g., ciprofloxacin, gatifloxacin, gemifloxacin; levofloxacin, lomefloxacin, moxifloxacin, norfloxacin, and ofloxacin); antimycobacteria drugs (e.g., isoniazid, rifampin, rifabutin, rifapentine, pyrazinamide, ethambutol, ethionamide, capreomycin, clofazimine, and dapsone); and miscellaneous antimicrobials (e.g., colistimethate sodium, methenamine hippurate, methenamine mandelate, metronidazole, mupirocin, nitrofurantoin, polymyxin B, clindamycin, choramphenicol, quinupristin-dalfopristin, linezolid, spectrinomycin, trimethoprim, pyrimethamine, and trimethoprim-sulfamethoxazole).

The device including one or more reactive chemical components, reactive biologic components, or reactive physical components that include one or more cytotoxic, cytostatic, apoptotic, and/or chemotherapeutic agents can include one or more of an antifungal agent. Examples of antifungal agents include, but are not limited to, anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

The device including one or more reactive chemical components, reactive biologic components, or reactive physical components that include one or more cytotoxic, cytostatic, apoptotic, and/or chemotherapeutic agents can include one or more of an anti-parasite agent. Examples of anti-parasite agents include, but are not limited to, antimalaria drugs (e.g., chloroquine, amodiaquine, quinine, quinidine, mefloquine, primaquine, sulfadoxine-pyrimethamine, atovaquone-proguanil, chlorproguanil-dapsone, proguanil, doxycycline, halofantrine, lumefantrine, and artemisinins); treatments for amebiasis (e.g., metronidazole, iodoquinol, paromomycin, diloxanide furoate, pentamidine, sodium stibogluconate, emetine, and dehydroemetine); and other anti-parasite agents (e.g., pentamidine, nitazoxanide, suramin, melarsoprol, eflornithine, nifurtimox, clindamycin, albendazole, and tinidazole).

The device including one or more reactive chemical components, reactive biologic components, or reactive physical components that include one or more cytotoxic, cytostatic, apoptotic, and/or chemotherapeutic agents can include one or more of an antiviral agent. Examples of antiviral agents include, but are not limited to, nucleoside analogs used to treat herpes simplex virus (HSV) and varicella-zoster virus (VZV) (e.g., valacyclovir, famciclovir, penciclovir, and trifluridine); nucleoside analogs used to treat cytomegalovirus (CMV) (e.g., ganciclovir, valganciclovir, and cidofovir); nucleoside and nonnucleoside reverse transcriptase inhibitors used to treat HIV (e.g., abacavir, didanosine, emtricitabine, lamivudine, stavudine, tenofovir, zalcitabine, zidovudine, delavirdine, efavirenz, and nevirapine); protease inhibitors used to treat HIV (e.g., atazanavir, darunavir, fosamprenavir, indinavir, lopinavir, nelfinavir, ritonavir, saquinavir, and tipranavir); and drugs used to treat hepatitis (e.g., interferon alfa, adefovir dipivoxil, entecavir, and ribavirin).

Two or More Reactive Components Combined to Modulate a Physiological Effect of the One or More Target Components. The device can include two or more reactive components that have been combined to modulate a physiological effect of the one or more target components. The two or more combined reactive components can be one or more binding agent combined with one or more of a denaturing agent, a degradative agent, a cell-disrupting agent, a modulator, an apoptotic agent, a cytotoxic agent, cytostatic agent, a chemotherapeutic agent, an antibody toxin or a combination thereof.

In an aspect, the device can include the two or more reactive components incorporated into a single biomolecule. For example, the first reactive component can be a binding agent, e.g., an antibody, that includes a second reactive component that is a degradative activity. Certain antibodies are capable of cleaving the amide bond of peptide bonds. See, e.g., Janda, et al., *Science* 241:1188-1191, 1988; Lacroix-Desmazes, et al., *J. Immunol.* 177: 1355-1363, 2006; Ponomarenko, et al., *Proc. Natl. Acad. Sci. USA,* 103: 281-286, 2006; and U.S. Pat. No. 6,387,674, each of which is incorporated herein by reference. Alternatively, the first reactive component can be a binding agent, e.g., an antibody, and can include a second reactive component that is a reactive oxygen species. The one or more target components can bind to one or more binding agents that are catalytic antibodies capable of generating the reactive oxygen species $H_2O_2$ in response to UV radiation. See, e.g., Wentworth, et al., *Science* 293: 1806-1811, 2001; Wentworth, *Science* 296: 2247-2249, 2002; Wentworth, et al., *Proc. Natl. Acad. Sci. USA,* 97: 10930-10935, 2000, each of which is incorporated herein by reference. One or more antibodies or other binding agents can be generated for both binding and degradation of one or more labels.

In an aspect, the first reactive component can be a binding agent, e.g., an antibody, that can include a second reactive component that is a cellular toxin. For example, the first reactive component can be an antibody that binds a cellular target component and the second reactive component can be a photosensitizer which is activated upon exposure to electromagnetic energy. See, e.g., Serebrovskaya, et al., *Proc. Natl. Acad. Sci. USA.* 106:9221-9225, 2009, which is incorporated herein by reference. In another example, the first reactive component can be an antibody directed against a cancer cell or other cellular target component and the second reactive component can be an auristatin, a cytotoxic inhibitor of tubulin polymerization. See, e.g., Ma, et al., *Clin. Cancer Res.* 12:2591-2596, 2006, which is incorporated herein by reference.

In an aspect, the two or more reactive components of the device can be incorporated into a single biomolecule and can include a first component that is a binding agent, e.g., an aptamer, and a second component that is a degradative agent, e.g., a protease. For example, one or more proteases can be conjugated or chemically linked to one or more oligonucleotide-based aptamers. The oligonucleotide-based aptamers are designed to bind to the target component. Upon binding to the oligonucleotide-based aptamers, the one or more target components are brought into proximity to the one or more proteases resulting in proteolytic degradation of the one or more target components. Proteases can be linked to oligonucleotide-based aptamers using any of a number of methods for conjugating a polypeptide to an oligonucleotide. In an aspect, a polypeptide protease can be conjugated to an oligonucleotide-based aptamer using a streptavidin-biotin bridge by introducing a biotinylated oligonucleotide into the aptamer sequence and linking it to a biotinylated protease through a streptavidin bridge. Alternatively, the polypeptide protease can be conjugated to the oligonucleotide-based aptamer using a thiol-maleimide linkage in which a carbon with an attached thiol group is placed on the aptamer and reacts with a maleimide group added to the C terminus of the protease. See, e.g., Nitin, et al., *Nucleic Acids Res.* 32:e58, 2004, which is incorporated herein by reference. A number of modified nucleotides are commercially available for use in synthesizing oligonucleotide aptamers with amines or other side chains for cross-linking (TriLink Biotechnologies, San Diego, Calif.; Sigma Aldrich, St. Louis, Mo.).

In an aspect, the first reactive component can be a binding agent linked to a second reactive component and encapsulated in a tunable vesicle. For example, the second reactive component, e.g., a denaturing and/or degradative agent, can be encapsulated in a tunable hydrogel. The binding of one or more target components to the label is illuminated by the energy source and leads to release of the denaturing and/or degradative agent from the hydrogel. In an aspect, target-responsive hydrogels can be generated in which the contents of the hydrogel are selectively released in response to binding a specific target. The hydrogel can incorporate one or more binding agents that are antibodies. The hydrogel can release its contents in response to an antibody-antigen interaction. See, e.g., Miyata, et al., *Proc. Natl. Acad. Sci. USA* 103: 1190-1193, 2006, which is incorporated herein by reference. In an aspect, the target-responsive hydrogel can incorporate one or more binding agents that are oligonucleotide-based aptamers and release its contents in response to an aptamer-ligand interaction. See Yang, et al., *J. Am. Chem. Soc.* 130: 6320-6321, 2008, which is incorporated herein by reference. In the latter case, two or more distinct aptamers configured to partially overlap during hybridization can be copolymerized into a polyacrylamide hydrogel. At least one of the two or more aptamers binds to a specific target, e.g., target component. When the target component binds to the aptamer, the number of nucleotide bases available for hybridization between the overlapping aptamers is reduced, causing them to separate. Separation of the overlapping aptamers allows the hydrogel to dissolute and release its contents. A target responsive hydrogel can be generated which incorporates aptamers that specifically recognize one or more target components. The hydrogel itself can be loaded with one or more proteases or other reactive components that are configured to modulate a physiological effect of the target components. The contents of the hydrogel are released upon binding of the one or more target components to the aptamers associated with the hydrogel. In an aspect, hydrogels can be used for molecular imprinting. See, e.g., Byrne et al., "Molecular imprinting within hydrogels," *Advanced Drug Delivery Reviews,* 54: 149-161, 2002, which is incorporated herein by reference.

Device Including Substrates for Reactive Components

The device can include one or more reactive components including binding agents, denaturing agents, degradative agents, modulators, or combinations thereof, wherein the one or more reactive components can be free in solution within one or more second reservoirs of the device. Alternatively, the one or more reactive components can be immobilized on a solid substrate within the one or more second reservoirs or within the lumen of the device. The solid substrate can be a matrix, e.g., a bead or a filter, added to one or more second reservoirs of the device. Examples of applicable solid substrates include, but are not limited to, beads, particles, membranes, semi-permeable membranes, capillary, or microarrays. The solid substrate can be comprised of an inorganic material, e.g., glass, alumina, silica, silicon, zirconia, graphite, magnetite, semiconductors, or combinations thereof. Alternatively, the solid substrate can be comprised of an organic material, e.g., polysaccharides including agarose, dextran, cellulose, chitosan, and polyacrylamide, polyacrylate, polystyrene, polyvinyl alcohol, or combinations thereof. Alternatively, the one or more specific binding agents or one or more reactive components can be associated with a solid substrate that are cells, e.g., mammalian cells, enucleated erythrocytes, bacteria, or viral particles or vesicles such as liposomes or other micellular vesicles.

In an aspect, the one or more reactive components, either free in solution or bound to a solid substrate, can be prevented from leaving the one or more second reservoirs of the device either due to size exclusion using a filter or mesh or due to physical attachment to the device. In a detailed aspect, one or more labeled target components present in the blood can bind to the one or more reactive components and be sequestered for inactivation as the blood passes through the device.

The one or more reactive components can be bound to the solid substrate either directly or indirectly. For example, the one or more reactive components can be coupled to the solid substrate by covalent chemical bonds between particular functional groups on the specific binding agent (e.g., primary amines, sulfhydryls, carboxylic acids, hydroxyls, and aldehydes) and reactive groups on the solid substrate. A variety of activating compounds and schemes for directly bonding ligands to solid substrates are known. Some examples include, but are not limited to, cyanogen bromide, cyanuric chloride, epichlorohydrin, divinyl sulphone, p-toluene-sulphonyl chloride, 1,1'-carbonyldiimidazole, sodium metaperiodate, 2-fluoro-1-methylpyridiniumtoluene-4-sulphonate, glycidoxypropyl-trimethoxysilane and 2,2,2-trifluoroethanesulphonyl chloride. For example, cyanogen bromide in base reacts with hydroxyl (OH) groups on agarose solid substrate to form cyanate esters or imidocarbonates. These groups readily react with primary amines under mild conditions resulting in a covalent coupling of the ligand to the agarose solid substrate. Reactive imidocarbonates can also be formed on carbon nanotubes, for example, through reactive carboxyl groups generated by treatment of the nanotubes with oxidizing agents. See, e.g., Bianco, et al., in *Nanomaterials for Medical Diagnosis and Therapy.* pp. 85-142. Nanotechnologies for the Live Sciences Vol. 10 Edited by Challa S. S. R. Kumar, WILEY-VCH Verlag GmbH & Co. KGaA, Weinheim, 2007, which is incorporated herein by reference. Functionalization of silicon chips with carboxyl groups can be subsequently used to immobilize proteins in the presence of N-ethyl-N'-(3-dimethylaminopropyl)carbodiimide hydrochloride (EDC) and N-hydroxysuccinimide ester (NHS). See, e.g., Hu, et al., *Rapid Commun. Mass Spectrom.* 21:1277-1281, 2007, which is incorporated herein by reference.

The one or more reactive components can have linking or spacer groups bound to the C-terminus which when present can be used to bind the specific binding agent to the solid substrate indirectly. When present the linking group can be a polymer or a monomer. A linking group can be a chain of from 1-10 amino acids. Other examples of linking groups include, but are not limited to, polyethylene glycol, polypropylene glycol, polyesters, polypeptides, polyethers, polysaccharides, glycidoxyalkyl, alkoxyalkyl, alkyl, glycidoxypropyl, ethyl, propyl, phenyl and methacryl; and silicon containing linking groups such as diethyl(triethoxysilylpropyl)malonate; 3-mercaptopropyltrimethoxysilane; 3-aminopropyltrimethoxysilane; N-[(3-trimethoxysilyl)propyl]ethylenediaminetriacetic acid; p-(chloromethyl)phenyltrimethoxysilane; vinyltriethoxysilane; 3-bromopropyltriethoxysilane; and 3-glycidoxypropyltrimethoxysilane.

In general, any of a number of homobifunctional, heterofunctional, and/or photoreactive cross linking agents can be used to conjugate one or more reactive components to an appropriately derivatized substrate. Examples of homobifunctional cross linkers include, but are not limited to, primary amine/primary amine linkers such as BSOCES ((bis(2-[succinimidooxy-carbonyloxy]ethyl)sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2'pyridyldithio]-propionamido) butane). Examples of heterofunctional cross linkers include, but are not limited to, primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-gamma-maleimidobutyryl-oxysuccinimide ester), Sulfo GMBS (N-γ-maleimidobutyryloxysulfosuccinimide ester), EMCS(N-(epsilon-maleimidocaproyloxy)succinimide ester), Sulfo EMCS(N-(epsilon-maleimidocaproyloxy)sulfo succinimide), SIAB (N-succinimidyl(4-iodoacetyl)aminobenzoate), SMCC (succinimidyl 4-(N-maleimidomethyl)cyclohexane-1-carboxylate), SMPB (succinimidyl 4-(rhomaleimidophenyl)butyrate), Sulfo SIAB (N-sulfosuccinimidyl(4-iodoacetyl)aminobenzoate), Sulfo SMCC (sulfosuccinimidyl 4-(N-maleimidomethyl)cyclohexane-1-carboxylate), Sulfo SMPB (sulfosuccinimidyl 4-(rho-maleimidophenyl)butyrate), and MAL-PEG-NHS (maleimide PEG N-hydroxysuccinimide ester); sulfhydryl/hydroxyl linkers such as PMPI (N-rho-maleimidophenyl)isocyanate; sulfhydryl/carbohydrate linkers such as EMCH(N-(epsilon-maleimidocaproic acid) hydrazide); and amine/carboxyl linkers such as EDC (1-ethyl-3-(3-dimethylaminopropyl)carbodiimide hydrochloride).

In an aspect, the one or more reactive components can be linked to a solid substrate through non-covalent interactions. Examples of non-covalent interactions include, but are not limited to, protein-protein interactions such as those between avidin/streptavidin and biotin, protein A and immunoglobulins, protein G and immunoglobulins, or secondary antibodies with primary antibodies. For example, the one or more reactive components can be modified with biotin using standard methods and bound to a solid substrate derivatized with streptavidin. One or more reactive components can be modified with streptavidin and bound to a solid substrate derivatized with biotin. A single chain antibody can incorporate streptavidin as part of a fusion protein to facilitate attachment of the antibody to the solid substrate via a biotin-streptavidin linkage. See, e.g., Koo, et al. *Appl. Environ. Microbiol.* 64:2497-2502, 1999. Solid substrates such as beads or other particulate substrates derivatized with protein A, protein G, streptavidin, avidin, biotin, secondary antibodies are available from commercial sources (from, e.g., Pierce-Thermo Scientific, Rockford, Ill., Sigma-Aldrich, St. Louis, Mo.). In an aspect, the one or more reactive components can bind to the solid substrate through a non-covalent interaction and be cross-linked to the solid substrate using a cross-linking agent.

In an aspect, the one or more reactive components can be associated with cells as a solid substrate, e.g., mammalian cells, enucleated erythrocytes, bacteria, or viral particles, or vesicles such as liposomes or other micellular vesicles. Cells and vesicles can be modified with one or more reactive components using many of the same methods as provided herein. One or more reactive components can be bound to cells or vesicles using one or more homobifunctional or heterofunctional cross-linkers through primary amines and carboxyl groups. Alternatively, cells can be modified with one or more reactive components using a biotin-streptavidin bridge. For example, one or more reactive components can be biotinylated and linked to a non-specifically biotinylated cell surface through a streptavidin bridge. An antibody, aptamer, or receptor can be biotinylated using standard procedures. The surface membrane proteins of a cell can be biotinylated using an amine reactive biotinylation reagent such as, for example, EZ-Link Sulfo-NHS-SS-Biotin (sulfosuccinimidyl 2-(biotinamido)-ethyl-1,3-dithiopropionate; Pierce-Thermo Scientific, Rockford, Ill., USA; see, e.g., Jaiswal, et al. *Nature Biotech.* 21:47-51, 2003; U.S. Pat. No. 6,946,127).

In an aspect, the one or more reactive components can be associated with lipid or micellular vesicles. In an aspect, the one or more reactive components can be antibodies attached to a liposome. Antibodies can be added to liposomes using cross-linking agents and protein A. See, e.g., Renneisen, et al., *J. Bio. Chem.*, 265:16337-16342, 1990, which is incorporated herein by reference. The liposomes are formed from dry lipid in the presence of an aqueous solution, e.g., a buffer of appropriate pH followed by extrusion through a high pressure device fitted with a polycarbonate filter with the desired pore size to form liposomes of a specific size range. The liposomes are modified with N-succinimidyl 3-(2-pyridyldithio)propionate-modified protein A. The one or more antibodies are linked to the liposomes through selective binding to the protein A. Alternatively, thiolated antibodies can be covalently linked to liposomes prepared with 4-(p-maleimidophenyl)butyrylphosphatidyl-ethanolamine. See, e.g., Heath, et al., *PNAS* 80:1377-1381, 1983, which is incorporated herein by reference.

In an aspect, the one or more reactive components can be expressed on the surface of a cell. The one or more reactive components can be naturally expressed on the surface of a cell, such as a receptor of a specific inflammatory mediator on a specific cell type. Alternatively, the one or more reactive components can be expressed on the surface of a cell using genetic manipulation. For example, cells can be genetically manipulated to express a receptor that binds one or more structural elements of the target component. In one example, cells can be genetically manipulated to express one or more specific antibodies on the cell surface. Methods have been provided for cell surface expression of single chain Fv antibody fragments (scFv) fused to membrane-associated proteins. See, e.g., Ho, et al., *Proc. Natl. Acad. Sci. USA* 103: 9637-9642, 2006; Francisco, et al., *Proc. Natl. Acad. Sci. USA* 90:10444-10448, 1993; U.S. Pat. Appl. No. 2006/0083716, each of which is incorporated herein by reference. In a detailed aspect, the cDNA sequence encoding all or part of an antibody recognizing a structural element of the target component is fused in an expression construct in frame with a membrane-associated protein and expressed in an appropriate cell type.

Device Including Controller in Communication with and Responsive to a Sensor

The device can include at least one controller in communication with the one or more sensors, and in communication with the at least one controllable flow barrier to the at least one lumen, wherein the controller is configured to control flow of the one or more of blood or lymph through the at least one lumen. The one or more sensors can transmit data to the controller regarding the one or more signal responses associated with the one or more labeled target components in the blood or lymph of the vertebrate subject. The controller can be integrated into the device. Alternatively, the controller can be a separate component of the device that receives and transmits data and/or commands either with or without wires. For example, an implanted device can send data regarding the sensed signal responses of one or more target components to an external controller through a wireless signal.

The controller can compare the input data regarding the physiological effect of the one or more target components in the blood or lymph of the vertebrate subject with stored data. The controller itself can include the stored data. Alternatively, the controller can have access to one or more remote databases that include the stored data. The stored data can be data regarding the normal levels of one or more target components in normal or healthy subjects without a disease or condition. The stored data can be data regarding normal parameters, e.g, size, granularity, autofluorescence, scattering properties of one or more target components in normal or healthy subjects. The stored data can include data regarding the baseline level of one or more target components in a vertebrate subject prior to the onset of a disease or condition. The stored data can include data regarding the level of one or more target components in a vertebrate subject at one or more previous time points. The controller assesses the most recently obtained input data with the stored data and is configured to controllably initiate steps to release an amount of one or more labels from the at least one first reservoir.

The device including the controller can also be in communication with and configured to be informed by one or more sensors. In response to input data, the controller can cause the device to controllably divert all or part of the blood or lymph of a vertebrate subject through the controllable flow barrier into at least one lumen. Access to at least one lumen can be controlled by a flow-modulating element or controllable flow barrier. A flow-modulating element can be a gate, a valve, a louver, a splitter or flow divider, a filter, a baffle, a channel restriction, a retractable iris, or other structure that controllably limits access of the blood flow to at least one lumen. The controller can send a signal to the flow-modulating element indicating whether or not all or part of the flow of blood should be diverted into at least one lumen.

The device including the controller can also be in communication with and configured to be informed by one or more sensors to control access to or release of one or more reactive components from one or more second reservoirs. In response to input data, the controller can controllably initiate release or activation of one or more reactive components designed to modulate a physiological effect of the one or more target components, e.g., to inactivate, ablate, alter, arrest, disrupt, destroy, inactivate, or ablate the one or more target components. The one or more reactive components are controllably released or activated in the one or more second reservoirs of the device. In an aspect, the controller can release one or more reactive components to modulate the activity of one or more target components. Alternatively, the controller can send data regarding the levels of one or more target components in the blood of the vertebrate subject to the subject, to one or more third party individuals such as a physician or other caregiver, to a computing device, or to a combination thereof. The subject and/or caregiver or computing device can choose to initiate steps to inactivate, ablate, alter, arrest, disrupt, destroy, inactivate, or ablate the one or more target components by releasing or activating one or more reactive components.

The controller can also include one or more algorithms that provide computational models of a disease or condition. For example, a computational model of a disease or condition can include information regarding, for example, a variety of interrelated signaling pathways involved in the disease process. The computational model can inform decisions made by the controller. Examples of computational models related to inflammatory disease, cancer and pathogen infection have been described. See, e.g., U.S. Pat. No. 7,415,359 B2; U.S. Patent Applications 2007/0083333 A1, 2008/0201122 A1; Vodovotz, et al., *Curr. Opin. Crit. Care.* 10:383-390, 2004; Zenker, et al., *PLoS Comput. Biol.* 3(11):e204, 2007; Li, et al., *PLoS ONE* 3(7):e2789, 2008; Vodovotz, et al., *PLoS Comput. Biol.* 4:e1000014, 2008; An, *Theoretical Biology Medical Modeling* 5:11, 2008; Lee, et al., *Proc. Natl. Acad. Sci. USA.* 104:13086-13091, 2007; Zhou, et al., *HIV Medicine.* 6:216-223, 2005, each of which is incorporated herein by reference.

Device for Controlling Levels of One or More Target Components to a Target Level A device is disclosed herein that includes a sensor configured to detect one or more signal response associated with one or more labeled target components in the blood or lymph of a vertebrate subject. The device is configured to modulate a physiological effect of the one or more target components to control levels of the one or more target components to a target value. The target value can be a desired concentration of one or more target components in the blood or lymph, or the target value can be a desired range of concentrations of one or more target components in the blood or lymph. Alternatively, the target value can be a desired ratio of concentrations of two or more target components in the blood or lymph. The desired ratio can be determined by a least squares fit of the concentrations of the two or more target components. The target value of a target component can be a desired concentration and/or concentration range and/or ratio of concentrations that is a specific value or range of values such as, for example, a value or range of values observed in a normal subject. Alternatively, the target value of a target component can be a desired concentration and/or concentration range and/or ratio of concentrations that is at least 20%, at least 40%, at least 60%, at least 80%, or at least 100% below or above the current level of the target component in the blood or lymph of a vertebrate subject.

The target value of one or more target components can be a desired concentration and/or concentration range that is below that observed in the blood or lymph of a vertebrate subject experiencing a disease, disorder, or infection. For example, a number of target components, e.g., inflammatory mediators, are elevated in the blood of subjects diagnosed with systemic immune response syndrome (SIRS) and sepsis. See, e.g., Ueda, et al., *Am. J. Respir. Crit. Care Med.* 160:132-

136, 1999; Kurt, et al., *Mediators Inflamm.* 2007:31397, 2007; Kellum, et al., *Arch. Intern. Med.* 167:1655-1663, 2007; Wang, et al., *Crit. Care* 12:R106, 2008; each of which is incorporated herein by reference. As an example, the levels of TNF-α, IL-6, and IL-8 in normal subjects is reported as less than 5 pg/ml, less than 10 pg/ml, and less than 10 pg/ml, respectively. In individuals with septic shock, the serum levels of TNF-α, IL-6, and IL-8 are significantly elevated to mean values of 138+/−22 pg/ml, 27,255+/−7,895 pg/ml, and 2,491+/−673 pg/ml, respectively. See Ueda, et al., *Am. J. Respir. Crit. Care Med.* 160:132-136, 1999; which is incorporated herein by reference.

The relative levels of one or more target components in the blood or lymph of the vertebrate subject can be correlated with prognosis and survival. For example, sepsis non-survivors have proportionally higher levels of inflammatory mediators relative to sepsis survivors and normal controls. In one study, high levels of both IL-10 (mean of 45 pg/ml) and IL-6 (mean of 735 pg/ml) at hospital admission were associated with increased mortality as compared with low initial levels of IL-10 (mean of 7.4 pg/ml) and IL-6 (mean of 15 pg/ml). In another example, elevated serum levels of IL-6 were correlated with sepsis symptom scores and poor outcome. These data suggest that modulating the levels of one or more inflammatory mediators to a desired target value in the blood can alter the course of the disease. See, e.g., Kellum, et al., *Arch. Intern. Med.* 167:1655-1663, 2007; Presterl, et al., *Am. J. Respir. Crit. Care Med.* 156:825-832, 1997; each of which is incorporated herein by reference.

The relative levels of one or more target components in the blood of the vertebrate subject can be correlated with a chronic disease. For example, subjects with rheumatoid arthritis have increased levels of various inflammatory mediators relative to normal subjects including IL-6 (15.8 pg/ml versus 4.0 pg/ml), TNF-α (10 pg/ml versus 3.2 pg/ml), IL-1β (129.8 pg/ml versus 57.3 pg/ml), IL-8 (9.3 pg/ml versus 2.6 pg/ml), IL-10 (15.5 pg/ml versus 4.6 pg/ml), and IL-12 (20.2 pg/ml versus 6.2 pg/ml). Psoriatic arthritis is also characterized by increased levels of circulating inflammatory mediators with statistically significant increases in the serum levels of various inflammatory mediators in subjects diagnosed with psoriatic arthritis versus normal. See, e.g., Nowlan, et al., *Rheumatology* 45:31-37, 2006; Mittal & Joshi, *J. Indian Rheumatol. Assoc.* 10:59-60, 2002; Szodoray, et al., *Rheumatology* 46:417-425, 2007, each of which is incorporated herein by reference.

The target value of one or more cellular target components can be a desired concentration or concentration range of target cells that is below that observed in the blood or lymph of a vertebrate subject experiencing a disease or condition. For example, elevated levels of red blood cells are associated with exposure to carbon monoxide, long-term lung disease, kidney disease, some cancers, certain forms of heart disease, liver disease. Elevated levels of platelets are associated with bleeding, iron deficiency, some diseases like cancer, or bone marrow problems. Elevated levels of neutrophils, eosinophils, and/or lymphocytes are associated with infection, malignancy and autoimmune diseases. The desired concentration or concentration range can be the concentration or concentration range observed in a normal individual. For example, the normal range of white blood cells in men and nonpregnant women ranges from 4.5 to $11 \times 10^9$ cells per liter while in pregnant women, the white blood cell counts range from 5.9 to $25.7 \times 10^9$ cells per liter depending upon whether the vertebrate subject is in the first, second or third trimester or postpartum. Similarly, normal red blood cell counts range from 4.7 to $6.1 \times 10^{12}$ in men, 4.2 to $5.4 \times 10^{12}$ in women, 4.0 to $5.5 \times 10^{12}$ in children and 4.8 to $7.1 \times 10^{12}$ in newborns. Normal platelet counts range from 150 to $450 \times 10^9$ for children and 150 to $400 \times 10^9$ for adults. See, e.g., Rea, WebMD. Complete Blood Count (CBC) at www.webmd.com/a-to-z-guides/complete-blood-count-cbc. Last updated Sep. 12, 2008; accessed Oct. 5, 2009; incorporated herein by reference.

The target value can be a percentage range of cells in the blood. For example, of the total white blood cells in a normal subject, neutrophils range from 50% to 62%, band neutrophils range from 3% to 6%, lymphocytes range from 25% to 40%, monocytes range from 3% to 7%, eosinophils range from 0% to 3%, and basophils range from 0% to 1%.

The target value can be a desired ratio of concentrations of two or more target components in the blood or lymph as determined by a least squares fit of the concentration values of the two or more target components. In this instance, the levels of one or more target components can be altered to modulate the overall ratio of two or more target components. For example, levels of neutrophils relative to leukocytes is reportedly is correlated with cardiovascular risk in that increased neutrophils and/or decreased leukocytes are associated with diabetes, coronary artery disease, unstable angina, and increased risk of myocardial infarction. See, e.g., Horne, et al., *J. Am. Coll. Cardiol.* 45:1638-1643, 2005, which is incorporated herein by reference.

In some pathological states such as cancer or infection, the ideal target value of one or more target components can be zero. In the instance where a target value of zero is not attainable, the target value can be a value that reduces the symptoms and/or the disease progression. In malaria infected individuals, for example, the degree of parasitemia is correlated with the severity of the disease. The number of parasites per microliter of blood is used to assess parasitemia. For example, a vertebrate subject can just be showing signs of symptoms at 100 parasites per microliter (0.002% parasitemia), severe malaria at 100,000 to 250,000 parasites per microliter (2-5% parasitemia), and near death at 500,000 parasites per microliter (10% parasitemia). Reducing parasitemia can reduce symptoms and disease severity.

Similarly, the target value of one or more target component, e.g., a toxin or illicit drug, can be zero. In the instance where a target value of zero is not attainable, the target value can be a value that reduces toxicity. For example, elevated levels of lead in the blood in adults can damage the nervous, hematologic, reproductive, renal, cardiovascular, and gastrointestinal systems. The majority of cases of lead poisoning are workplace related. The U.S. Department of Health and Human Services recommends that blood levels of lead among adults be reduced to <25 ug/dL. The highest blood levels of lead acceptable by standards of the U.S. Occupational Safety Health Administration is 40 ug/dL. The geometric mean blood levels of lead of all adults in the U.S. is <3 ug/dL. MMWR 58(14):365-369, 2009, which is incorporated herein by reference.

PROPHETIC EXAMPLES

Example 1

Device Including Sensor for Detecting One or More Target Circulating Tumor Cells and for Binding and Altering Circulating Tumor Cells for Treatment of a Neoplastic Disease or Condition An implantable device is described for treating a neoplastic disease, e.g. metastatic breast cancer, associated with the presence of circulating tumor cells in the peripheral blood of a subject. The components of the implantable device are incorporated into a stent inserted into a femoral artery of the subject. The implantable device includes two reservoirs: a first reservoir containing a flourescein-labeled aptamer that can bind a circulating tumor cell in the peripheral blood of a subject and emit a fluorescent signal in response to the binding; and a second reservoir containing a chemotherapeutic agent, e.g., doxorubicin. The implantable device further includes an optical sensor consisting of a set of light emitting diodes (LEDs) emitting light at a specific wavelength to elicit a signal response associated with the fluorescently labeled circulating tumor cells, and a metal-oxide-semiconductor (CMOS) sensor to detect a signal response associated with the fluorescently labeled circulating tumor cells. The optical sensor is connected to a controller configured to control release of a chemotherapeutic agent from the second reservoir positioned downstream from the optical sensor. The implantable device also includes a transmitter for transmitting data to an external receiver regarding the sensed levels of circulating tumor cells.

The first reservoir of the device contains a fluorescein-containing fluorescent label conjugated to an oligonucleotide aptamer binding component. The aptamer selectively binds to the epithelial cell-cell adhesion molecule (EpCAM) expressed on circulating metastatic tumor cells of epithelial cell origin. Fluorescein has a maximal absorbance at a wavelength of 494 nm and maximal emission at a wavelength of 521 nm (from, e.g., Molecular Probe—Invitrogen, Carlsbad, Calif.). Fluorescein is conjugated to a binding component, e.g., an aptamer. Aptamers directed against EpCAM are isolated from a large library of $10^{14}$ to $10^{15}$ random oligonucleotide sequences using an iterative in vitro selection procedure termed "systematic evolution of ligands by exponential enrichment" (SELEX). See, e.g., Cao, et al., *Current Proteomics* 2:31-40, 2005; Proske, et al., *Appl. Microbiol. Biotechnol.* 69:367-374, 2005; Jayasena *Clin. Chem.* 45:1628-1650, 1999, which are incorporated herein by reference. The 3-prime end of the EpCAM-specific aptamer is modified with an amino group during chemical synthesis using a 3'-amino-modifier C7-CPG (from, Glen Research, Sterling, Va.). Fluorescein is conjugated to the amine-modified aptamer using a fluorescein-reactive dye containing a succinimidyl ester moiety that reacts efficiently with primary amines (e.g., 5-carboxyfluorescein, succinimidyl ester, from Molecular Probes—Invitrogen, Carlsbad, Calif.).

The fluorescein-labeled aptamer is further modified with a quenching molecule to create a FRET (fluorescence resonance energy transfer) pair that will only fluoresce in response to binding a target circulating tumor cell. An appropriate quencher to pair with fluorescein is DABCYL acid (4-(dimethylaminoazo)benzene-4-carboxylic acid). DABCYL is added to the 5-prime end of the fluorescein-labeled aptamer during chemical synthesis using 5'-DABCYL phosphoramidite (6-(N-4'-carboxy-4-(dimethylamino) azobenzene)-aminohexyl-1-O-(2-cyanoethyl)-(N,N-diisopropyl)-phosphoramidite; from, e.g., Glen Research, Sterling, Va.). The aptamer is configured such that in the absence of binding a circulating metastatic tumor cell, fluorescein and DABCYL attached to the aptamer are in close proximity and little to no fluorescence is detected upon excitation. In response to binding a circulating tumor cell, a conformational change occurs in the aptamer, separating fluorescein and DABCYL and allowing fluorescence associated with fluorescein to be detected.

The fluorescein/DABCYL labeled EpCAM aptamer is incorporated into the first reservoir of the device and is released at constant rate over time into the peripheral blood. In this example, the EpCAM aptamer is formulated with poly (DL-lactide-co-glycolide) (PLGA) into nanoparticles and coated onto some fraction of the stent surface. See, e.g., Nakano, et al., *J. Am. Coll. Cardiol. Intv.*, 2:277-283, 2009, which is incorporated herein by reference. Briefly, the fluorescein/DABCYL labeled EpCAM aptamer is encapsulated into cationic PLGA nanopartices using an emulsion solvent diffusion method. Electrodeposition is used to coat the stent with the PLGA nanoparticles containing the fluorescein/DABCYL labeled EpCAM aptamer. See, e.g., Htay &, Lui, *Vasc. Health Risk Management*, 1:263-276, 2005, which is incorporated herein by reference. While release of fluorescein/DABCYL labeled EpCAM into the circulation occurs upstream of the optical sensor, it is anticipated that interaction of the labeled aptamer with a circulating tumor cell will occur elsewhere in the circulation, but this interaction is ultimately detected when the labeled circulating tumor cell passes through the implantable device.

Fluorescence associated with the fluorescein/DABCYL EpCAM aptamer bound to a circulating metastatic tumor cell is detected using an optical sensor. The optical sensor consists of a one-chip sensing device designed for real time in vivo imaging and including a complementary metal-oxide semiconductor (CMOS) sensor, a blue-light emitting diode, and a color filter. See, e.g., Tamura, et al. *J. Neurosci. Methods* 173:114-120, 2008; Ng, et al., *J. Neurosci. Methods* 156:23-30, 2006, which are incorporated herein by reference. The one-chip sensing device including the CMOS sensor is incorporated into the stent. See, e.g., U.S. Patent Application 2009/0298704, which is incorporated herein by reference. In response to sensing fluorescence associated with a circulating tumor cell a signal is sent to the second reservoir to initiate release of a chemotherapeutic agent. In addition, a signal indicating detection of each circulating tumor cell is sent wirelessly to an external receiver. See, e.g., U.S. Patent Application 2009/0043183, which is incorporated herein by reference. The external receiver is incorporated into a patch worn by the subject. The data recorded in the patch is periodically analyzed by the subject's physician to monitor the number of circulating tumor cells detected over a given time frame, including days and weeks.

The optical sensor is wired to the second reservoir containing a chemotherapeutic agent, e.g., doxorubicin. In response to detecting a fluorescent circulating tumor cell, the optical sensor sends a signal to the second reservoir to trigger release of the doxorubicin. The second reservoir is a microfabricated array of micro-reservoirs incorporated into the stent. Each micro-reservoir contains a measured bolus of doxorubicin. Each micro-reservoir is sealed by a voltage sensitive metal foil responsive to an electrical signal. See, e.g., Grayson, et al., *Proc. IEEE*, 92:6-21, 2004; which is incorporated herein by reference. Electrical signals from the optical sensor trigger disintegration of the metal foil and release of the enclosed bolus of doxorubicin.

The subject's physician may choose to add additional medications to the subject's treatment regimen depending upon the number of circulating metastatic tumor cells detected in the subject's circulation. Additional medications can include additional chemotherapy and/or radiation therapy. The implantable device can continue to be used before and after these additional treatment options to monitor for the presence of circulating metastatic tumor cells and assess efficacy of the treatment regimen.

Example 2

Figure 4:
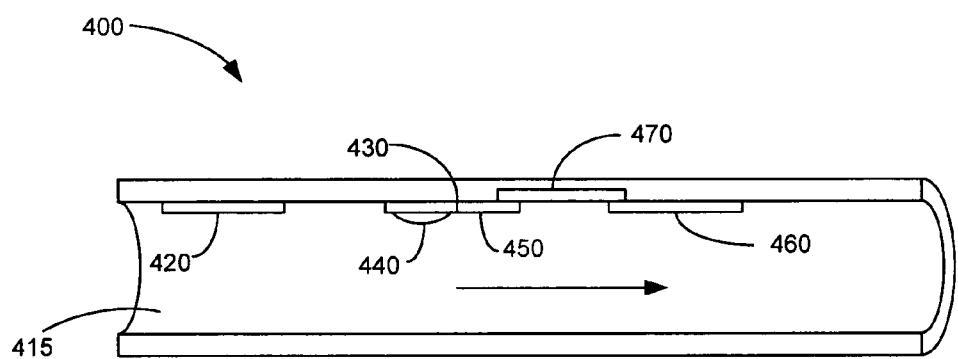
FIG. 4 depicts a diagrammatic view of an aspect of an embodiment of a device.

Device Including Sensor for Detecting One or More Target Circulating Tumor Cells and for Binding and Altering Circulating Tumor Cells for Treatment of a Neoplastic Disease or Condition Referring to FIG. 4, depicted is a partial diagrammatic cross-sectional view of an illustrative embodiment of an implantable device 400 for treating a neoplastic disease including a stent 410 including a lumen 415 configured for fluid flow; a first reservoir 420 containing a source of fluorescent label configured to bind circulating tumor cells in the peripheral blood of a subject; an optical sensor 430 including a light emitting diode 440 configured to provide energy to elicit a signal response associated with fluorescently labeled circulating tumor cells and a CMOS sensor 450 configured to detect signal responses associated with fluorescently-labeled circulating tumor cells; and a second reservoir 460 in communication with the optical sensor 430 through a wired connection 470 and containing a chemotherapeutic agent configured to cause apoptosis or necrosis of the circulating metastatic tumor cell.

Example 3

Device Including Source for Labeling and Imaging Target Inflammatory Mediators and for Ablating Inflammatory Mediators for Treatment of an Inflammatory Condition or Disease An implantable device is described for controlling elevated levels of eosinophils in a subject experiencing an inflammatory condition, e.g., asthma, by selectively sensing and controllably binding and inducing apoptosis of the eosinophils. The components of the implantable device are incorporated into an artificial multi-lumen bypass graft surgically placed in a large artery, e.g., the coronary artery, of the subject. The components of the implantable device include a first reservoir containing a fluorescent label to bind and emit a fluorescent signal in response to binding eosinophils in the blood of a subject; an optical sensor including a set of light emitting diodes (LEDs) emitting light at a specific wavelength to elicit a signal response associated with the fluorescently labeled eosinophils; a metal-oxide-semiconductor (CMOS) sensor to detect a signal response associated with elevated levels of fluorescently labeled eosinophils; a controller operationally linked to the optical sensor and configured to control flow of the peripheral blood through the artificial multi-lumen bypass graft in response to detecting elevated levels of fluorescently-labeled eosinophils in the blood; and a second reservoir including an apoptotic agent to selectively bind to and inactivate the fluorescently-labeled eosinophils using an apoptotic agent. The implantable device also includes a transmitter for transmitting data to an external receiver regarding the sensed levels of eosinophils in the blood of the subject.

The implantable device is incorporated into an artificial multi-lumen bypass graft. The artificial multi-lumen bypass graft is constructed of a biocompatible synthetic material, e.g., polyurethane, as described by Rashid, et al., *FASEB J.*, 22:2084-2089, 2008, which is incorporated herein by reference. The artificial multi-lumen bypass graft includes one main flow path and one side flow path branching from the main flow path. The first reservoir containing the fluorescent label and the optical sensor are incorporated into the main flow path and upstream of the diversion point with the side flow path. Access to the side flow path is controlled by a valve. The valve opens and closes in response to signals sent from the optical sensor regarding the sensed level of eosinophils. The side flow path is a multi-lumen catheter composed of fluoropolymer (from Zeus, Orangeburg, S.C.) through which the subject's blood is diverted. The multi-lumen portion of the artificial graft constitutes the second reservoir of the device and is configured to provide the blood components including the fluorescently labeled eosinophils ample surface area and exposure to an apoptotic agent.

The first reservoir of the device contains a Dapoxyl® fluorescent label conjugated to an antibody binding component. The antibody selectively binds to the IL-5 receptor expressed on the surface of eosinophils. Dapoxyl® (benzenesulfonic acid, 4-[5-[4-(dimethylamino)phenyl]-2-oxazolyl) has an excitation maxima at a wavelength of 370 nm and an emission maxima at a wavelength of 580 nm and is a solvent-sensitive fluorophore that does not fluoresce well when exposed to an aqueous environment, e.g., blood (from, e.g., Molecular Probe—Invitrogen, Carlsbad, Calif.). Antibodies directed against the IL-5 receptor are available from commercial sources (from, e.g., Sigma-Aldrich, St. Louis, Mo.). A target responsive Dapoxyl®-antibody conjugate is constructed by combining the IL-5 receptor antibody with the IL-5 receptor and the complex is non-selectively labeled with Dapoxyl® near the active site of the antibody. The IL-5 receptor antigen is removed, leaving Dapoxyl® labeled antibody with poor fluorescence in aqueous environments. Interaction of the IL-5 receptor antigen with the Dapoxyl®-labeled antibody protects the label near the active site from the aqueous environment and results in a large blue shift in the emission wavelength as well as an increase in fluorescence intensity. See, e.g., Brennan, *J. Fluor.* 9: 298-312, 1999, which is incorporated herein by reference.

The Dapoxyl®-labeled IL-5 receptor antibody is incorporated into the first reservoir of the device and is released at constant rate over time into the peripheral blood. The first reservoir includes an infusion pump attached to the exterior of the artificial multi-lumen bypass graft with flow access to the internal lumen of the main flow path. The infusion pump injects the labeled IL-5 receptor antibody into the blood flowing through the main flow path of the device. The SynchroMed II® implantable infusion pump (from Medtronic, Minneapolis, Minn.) is an example of an implantable infusion pump.

Fluorescence associated with the Dapoxyl®-labeled IL-5 receptor antibody bound to eosinophils is detected using an optical sensor. The optical sensor is positioned in the main flow path of the artificial multi-lumen bypass graft and upstream of the diversion point with the side flow path. The optical sensor consists of a sensing device designed for real time in vivo imaging and including a complementary metal-oxide semiconductor (CMOS) sensor, an ultraviolet emitting diode, and a color filter appropriate for capturing fluorescence associated with Dapoxyl® excitation. See, e.g., Tamura, et al. *J. Neurosci. Methods* 173: 114-120, 2008; Ng, et al., *J. Neurosci. Methods* 156: 23-30, 2006, which are incorporated herein by reference. The CMOS sensor is configured to count the number of fluorescence "events" over a period of time. Each fluorescence event represents an eosinophil passing by the CMOS sensor. When the rate of fluorescence events exceeds a threshold value indicative of excessive eosinophils in circulation, the sensor sends a signal to the valve controlling access to the side flow path. A signal is also sent wirelessly to an external receiver indicating the presence of excessive eosinophils in the subject's blood. See, e.g., U.S. Patent Application 2009/0043183, which is incorporated herein by reference. The data transmitted to the external receiver is periodically analyzed by the subject's physician to monitor the number of eosinophils detected over a given time frame, including days and weeks.

In response to reaching a threshold of fluorescence events, the controller associate with the CMOS sensor sends a signal to open the valve and at least a portion of the peripheral blood flowing through the artificial multi-lumen bypass graft is diverted into the multi-lumens of the side flow path. The multi-lumens of the side path are coated with 6'-sulfated sialyl-Lewis X, a carbohydrate structure that binds to Siglec-8, an immunoglobulin-like protein selectively expressed on the surface of eosinophils. The interaction of Siglec-8 with 6'-sulfated sialyl-Lewis X initiates caspase- and mitochondria-mediated apoptosis of the eosinophils. See, e.g., Nutku-Bilir, et al., *Am. J. Respir. Cell. Mol. Biol.*, 38: 121-124, which is incorporated herein by reference. Other cells in the blood lacking Siglec-8 are not affected by the presence of 6'-sulfated sialyl-Lewis X and pass through the side flow path and downstream to the main flow path.

The controller is configured to adjust access to the side flow path to achieve a target value of the fluorescently labeled eosinophils in the peripheral blood of the subject. The controller calculates the level of eosinophils in the peripheral blood based on input from the optical sensor, e.g., fluorescence events, and compares these data with target values, e.g., desired concentrations of eosinophils. The number of eosinophils in a normal human subject ranges from about 40 cells to about 400 cells per microliter of blood. More than 500 cells per microliter of blood is considered eosinophilia in adults. In some instances, the target value for eosinophils is that observed in a normal subject not experiencing an inflammatory disease. In other instances, the target value for eosinophils may represent a reduction of at least 20%, at least 40%, at least 60%, at least 80%, or at least 100% relative to the current level of eosinophils in the peripheral blood of the subject.

Example 4

Device Including Source for Labeling and Imaging Target Inflammatory Mediators and for Ablating Inflammatory Mediators for Treatment of an Inflammatory Condition or Disease Referring to FIG. 5A, depicted is a partial diagrammatic view of an illustrative embodiment of an implantable device 500 for modulating the levels of eosinophils in a subject including an artificial multi-lumen bypass graft 510 configured for fluid flow. The artificial multi-lumen bypass graft 510 is constructed of a biocompatible synthetic material, e.g., polyurethane, as described by Rashid, et al., *FASEB J.*, 22: 2084-2089, 2008, which is incorporated herein by reference. The artificial multi-lumen bypass graft 510 includes a lumen including a main flow path 520 and a side flow path 530 branching from the main flow path 520. The side flow path 530 is separated from the main flow path 520 by a valve 540. The artificial multi-lumen bypass graft 510 further includes a first reservoir 550 with an access port 560 to the main flow path 520 and containing a fluorescent label; a light emitting diode 570 configured to provide energy to elicit a signal response associated with fluorescently-labeled eosinophils; and a CMOS sensor 580 configured to detect signal responses associated with fluorescently-labeled eosinophils. Valve 540 controls access to side flow path 530 and opens or closes in response to signals sent from CMOS sensor 580 regarding the sensed level of fluorescently-labeled eosinophils. The side flow path 530 is a multi-lumen catheter composed of fluoropolymer (from Zeus, Orangeburg, S.C.) through which the subject's blood is diverted. Referring to FIG. 5B, depicted is a cross-section A through side flow path 530 of FIG. 5A. Side flow path 530 contains multiple parallel lumens 590. Each of the multiple parallel lumens 590 constitutes a second reservoir of the implantable device 500. The multiple parallel lumens 590 are configured to provide the blood components including the fluorescently labeled eosinophils ample surface area and exposure to an apoptotic agent, e.g., 6'-sulfated sialyl-Lewis X, to destroy the fluorescently labeled eosinophils.

Each recited range includes all combinations and sub-combinations of ranges, as well as specific numerals contained therein.

All publications and patent applications cited in this specification are herein incorporated by reference to the extent not inconsistent with the description herein and for all purposes as if each individual publication or patent application were specifically and individually indicated to be incorporated by reference for all purposes.

The state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Optical aspects of implementations will typically employ optically-oriented hardware, software, and/or firmware.

In a general sense the various aspects described herein which can be implemented, individually and/or collectively, by a wide range of hardware, software, firmware, or any combination thereof can be viewed as being composed of various types of "electrical circuitry." "Electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the description accompanying them are used as examples for the sake of conceptual clarity and that various configuration modifications using the disclosure provided herein are within the skill of those in the art. Consequently, the specific examples set forth and the accompanying description are intended to be representative of their more general classes. In general, use of any specific example herein is also intended to be representative of its class, and the non-inclusion of such specific components (e.g., steps), devices, and objects herein should not be taken as indicating that limitation is desired.

With respect to the use of substantially any plural or singular terms herein, the reader can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable or physically interacting components or wirelessly interactable or wirelessly interacting components or logically interacting or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an"; the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An implantable device comprising:
   a body defining at least one lumen configured for fluid flow;
   at least one first reservoir in communication with the at least one lumen;
   one or more energy sources configured to provide energy to elicit one or more signal responses associated with one or more labels that bind to one or more target components in one or more of blood fluid or lymph fluid of the vertebrate subject;
   one or more sensors configured to detect the one or more signal responses associated with one or more labeled target components; and
   one or more reactive components in communication with the at least one lumen and for release responsive to the one or more sensors, wherein the one or more reactive components are configured to modulate a physiological effect of the one or more target components in the one or more of blood fluid or lymph fluid of the vertebrate subject.

2. The device of claim 1, wherein the at least one first reservoir includes the one or more labels.

3. The device of claim 1, wherein at least one of the at least one first reservoir includes a first gated mechanism responsive to the one or more sensors and configured to release the one or more labels into the one or more of blood fluid or lymph fluid of the vertebrate subject.

4. The device of claim 1, wherein at least one of the at least one first reservoir includes a first gated mechanism responsive to the one or more sensors and configured to expose the one or more labels to the one or more of blood fluid or lymph fluid of the vertebrate subject.

5. The device of claim 1, wherein at least one of the at least one first reservoir is disposed within the at least one lumen.

6. The device of claim 1, wherein the one or more signal responses further include one or more signal responses associated with an interior of the at least one lumen.

7. The device of claim 1, wherein the one or more signal responses are associated with an interior of the one or more of a blood vessel or a lymph vessel of the vertebrate subject.

8. The device of claim 1, wherein the one or more labeled target components include one or more of circulating cells or circulating emboli.

9. The device of claim 1, wherein the one or more labeled target components include one or more of tumor cells, emboli, misfolded proteins, aggregated proteins, autoimmune antibodies, infectious agents, or infected cells.

10. The device of claim 1, wherein the one or more labeled target components include one or more labeled target cells.

11. The device of claim 1, wherein the one or more labeled target components include an intracellular target component.

12. The device of claim 10, wherein the one or more sensors are configured to detect the labeled target cell prior to obtaining a high resolution image of the labeled target cell.

13. The device of claim 12, wherein the one or more sensors are configured to correlate the target cell image and the detected label.

14. The device of claim 1, wherein the one or more sensor is external to the at least one lumen.

15. The device of claim 1, wherein the one or more sensor is internal to the at least one lumen.

16. The device of claim 1, wherein the device includes a single unit.

17. The device of claim 1, wherein the device includes two or more separate units.

18. The device of claim 1, wherein the device is configured to report to an outside source or to a computing device, and wherein the device is configured to report the detected one or more signal responses associated with the one or more labeled target components.

19. The device of claim 1, further including two or more parallel lumen configured to receive the one or more target components.

20. The device of claim 19, wherein a diameter of each of the two or more parallel lumen is approximately less than two cell diameters.

21. The device of claim 1, wherein the one or more reactive components alters, arrests, disrupts, destroys, inactivates or ablates the one or more target components.

22. The device of claim 1, wherein the one or more reactive components are configured within at least one second reservoir.

23. The device of claim 22, wherein the at least one second reservoir includes a second gated mechanism responsive to the one or more sensors and configured to release the one or more reactive components.

24. The device of claim 22, wherein the at least one second reservoir includes a second gated mechanism responsive to the one or more sensors and configured to expose the one or more reactive components.

25. The device of claim 1, wherein the one or more reactive components include one or more reactive chemical components.

26. The device of claim 25, wherein the one or more reactive chemical components include one or more of a denaturing agent, degradative agent, or binding agent.

27. The device of claim 25, wherein the one or more reactive chemical components are configured to bind to the at least one lumen or are configured to be released into the at least one lumen.

28. The device of claim 1, wherein the one or more reactive components include one or more reactive biologic components.

29. The device of claim 28, wherein the one or more reactive biologic components include one or more phagocytic cell types.

30. The device of claim 28, wherein the one or more second reservoirs include a source for producing the one or more reactive biologic components.

31. The device of claim 28, wherein the one or more reactive biologic components include a protein, lipid micelle, liposome, polymer, a catalytic antibody, or a combination thereof.

32. The device of claim 1, wherein the one or more reactive components include one or more reactive physical components.

33. The device of claim 32, wherein the one or more reactive physical components include one or more of polymers, imprinted polymers, or charged polymers.

34. The device of claim 1, further including at least one controllable flow barrier to the at least one lumen.

35. The device of claim 34, further including at least one controller in communication with the one or more sensors, and in communication with the at least one controllable flow barrier to the at least one lumen, wherein the controller is configured to control flow of the one or more of blood fluid or lymph fluid through the at least one lumen.

36. The device of claim 35, wherein at least one of the at least one first reservoir and at least one second reservoir is responsive to the at least one controller.

37. The device of claim 35, wherein the one or more energy sources are responsive to the at least one controller.

38. The device of claim 35, wherein the at least one controller is configured to control flow of the one or more of blood fluid or lymph fluid based on the one or more signal responses associated with the one or more labeled target components.

39. The device of claim 35, wherein the at least one controller is configured to control flow of the one or more of blood fluid or lymph fluid based on the label on the one or more target components.

40. The device of claim 35, wherein the at least one controller is configured to control flow of the one or more of blood fluid or lymph fluid and to control the presence of the one or more reactive chemical components in the one or more second reservoirs based on the label on the one or more target components.

41. The device of claim 1, further including at least one controller in communication with the one or more sensors, and in communication with the one or more energy sources, wherein the at least one controller is configured to control the one or more energy sources configured to provide energy to elicit one or more signal responses.

42. The device of claim 1, further including at least one controller in communication with the one or more sensors, wherein the at least one controller is configured to control release of the one or more reactive components configured to modulate the physiological effect of the one or more target components.

43. The device of claim 1, further including at least one programmable controller in communication with the at least one first reservoir.

44. The device of claim 1, wherein at least one controller and the one or more sensors are configured to control levels of the one or more target components to substantially attain a target level of the one or more target components in the one or more of blood fluid or lymph fluid of the vertebrate subject.

45. The device of claim 44, wherein the one or more sensors and the at least one controller are configured to control levels of the detected one or more target components to limit a deviation from the target level.

46. The device of claim 44, wherein the target level includes a desired concentration of the one or more target components in the one or more of blood fluid or lymph fluid.

47. The device of claim 44, wherein the target level includes a desired ratio of concentrations of two or more target components in the one or more of blood fluid or lymph fluid.

48. The device of claim 1, wherein the one or more sensors include a biosensor, chemical sensor, physical sensor, or optical sensor.

49. The device of claim 48, wherein the one or more sensors include one or more of a recognition-based substrate, an aptamer-based substrate, an antibody-based substrate, surface plasmon resonance, genetically modified cells, or genetically modified cells with receptor-linked signaling.

50. The device of claim 1, wherein the one or more sensors are configured to target the device to a site having an elevated level of the target components.

51. The device of claim 26, wherein the one or more binding agents are on a matrix adapted to the at least one second reservoirs, wherein the one or more binding agents are configured to sequester at least one of the one or more target components from the one or more of blood fluid or lymph fluid.

52. The device of claim 51, wherein the one or more binding agents include one or more of antibodies, receptors, or cognates configured to bind to at least one of the one or more target components.

53. The device of claim 1, wherein the device is intracorporeal.

54. The device of claim 1, wherein the device is at least partially extracorporeal.

* * * * *